US006413768B1

(12) United States Patent
Galen

(10) Patent No.: US 6,413,768 B1
(45) Date of Patent: Jul. 2, 2002

(54) EXPRESSION PLASMIDS

(75) Inventor: James E. Galen, Owings Mills, MD (US)

(73) Assignee: University of Maryland, Baltimore, MD (US)

( * ) Notice: Subject to any disclaimer, the term of this patent is extended or adjusted under 35 U.S.C. 154(b) by 0 days.

(21) Appl. No.: 09/204,117

(22) Filed: Dec. 2, 1998

(51) Int. Cl.⁷ .............................................. C12N 15/63
(52) U.S. Cl. .................. 435/320.1; 536/24.1; 530/300; 530/350; 530/403
(58) Field of Search ..................... 435/320.1; 536/24.1; 530/300, 350, 403

(56) References Cited

U.S. PATENT DOCUMENTS

| | | | |
|---|---|---|---|
| 4,735,801 A | | 4/1988 | Stocker |
| 4,760,022 A | * | 7/1988 | Molin et al. |
| 4,764,370 A | | 8/1988 | Fields et al. |
| 4,806,471 A | * | 2/1989 | Molin et al. |
| 5,093,252 A | * | 3/1992 | Kuhstoss et al. |
| 5,459,072 A | | 10/1995 | McKay et al. |
| 5,527,529 A | | 6/1996 | Dougan et al. |
| 5,545,541 A | | 8/1996 | Molin et al. |
| 5,643,771 A | | 7/1997 | Stocker |
| 5,672,345 A | | 9/1997 | Curtiss, III |
| 5,674,703 A | | 10/1997 | Woo et al. |
| 5,695,983 A | | 12/1997 | Miller et al. |
| 5,763,270 A | | 6/1998 | Eastman et al. |
| 5,770,214 A | | 6/1998 | Dougan et al. |
| 5,804,194 A | | 9/1998 | Dougan et al. |
| 5,824,538 A | | 10/1998 | Branstrom et al. |
| 5,851,519 A | | 12/1998 | Dougan et al. |
| 5,853,718 A | | 12/1998 | Molin et al. |
| 5,922,583 A | | 7/1999 | Mosey |
| 5,985,285 A | * | 11/1999 | Titball et al. |

FOREIGN PATENT DOCUMENTS

WO    WO 92/15689    *    9/1992

OTHER PUBLICATIONS

Kenn Gerdes et al. Unique type of plasmid maintenance function: postsegregational killing of plasmid–free cells vol. 83 pp. 3116–3120 May 1986.*
Gerdes et al. Mechanism of post–segregational killing by the hok/sok system of plasmid R1: sok antisense RNA regulates formation of a hok mRNA species correlated with killing of plasmid–free cells Molecular Microbiology 1990 4(11) 1818.*
Jensen et al., "Programmed cell death in bacteria: proteic plasmid stabilization system", Molecular Microbiology, 1995, 17 (2), pp. 205–210.
Pecota et al., "Combining the hok/sok par DE, and pnd Postsegregational Killer Loci To Enhance Plasmid Stability", Applied and Environmental Microbiology, May 1997, 63, (5), pp. 1917–1924.

Gerdes et al., "Effects of Genes Exerting Growth Inhibition and Plasmid Stability on Plasmid Maintenance", Journal of Bacteriology, Oct. 1987, 169 (10), pp. 4646–4650.
Gerdes et al., "Antisense RNA–Regulated Programmed Cell Death", Annu. Rev. Genet., 1997, pp. 1–31.
Gultyaev et al., "Programmed Cell Death by hok/sok of Plasmid R1: Coupled Nucleotide Covariations Reveal a Phylogenetically Conserved Folding Pathway in the hok Family of mRNAs", J. Mol. Biol., 1997, 273, pp. 26–37.
Franch et al., "Programmed Cell Death by hok/sok of Plasmid R–1: Processing at the hok mRNA 3–end Triggers Structural Rearrangements that Allow Translation and Antisense RNA Binding", J. Mol. Biol., 1997, 273, pp. 38–51.
Nikolaj Dam Mikkelsen and Kenn Gerdes, "Sok antisense RNA from plasmid R1 is functionally inactivated by Rnase E and polyadenylated by poly (A) polymerase I", Molecular Microbiology, 1997, 26 (2), pp. 311–320.
Thomas Franch and Kenn Gerdes, "Programmed cell death in bacteria: translational repression by mRNA end–pairing", Molecular Microbiology, 1996, 21 (5), pp. 1049–1060.
Kenn Gerdes and Soren Molin, "Partitioning of Plasmid R1 Structural and Functional Analysis of the par A Locus", J. Mol. Biol., 1986, 190, pp. 269–279.
Gerdes et al., "Plasmid Stabilization by Post–Segregational Killing", Genetic Engineering, 1997, 19, pp. 49–61.
Gerdes et al., "Stable Inheritance of Plasmid R1 Requires Two Different Loci", Journal of Bacteriology, Jan. 1985, 161 (1), pp. 292–298.
Kuowei Wu and Thomas K. Wood, "Evaluation of the hok/sok Killer Locus for Enhanced Plasmid Stability", Biotechnology and Bioengineering, 1994, 44, pp. 912–921.
Thomas K. Wood and Steven W. Peretti, "Effect of Chemicall–Induced, Cloned–Gene Expression on Protein Synthesis in *E. coli*", Biotechnology and Bioengineering, 1991, 38, pp. 397–412.
Kenn Gerdes, "The PARB (Hok/Sok) Locus of Plasmid R1: A General Purpose Plasmid Stabilization System", Biotechnology, Dec. 1998, 6, pp. 1402–1405.
Bravo et al., ."Identification of components of a new stability system of plasmid R1, ParD, that is close to the origin or replication of this plasmid", Mol Gen Genet, 1987, pp. 101–110.

(List continued on next page.)

*Primary Examiner*—Remy Yucel
(74) *Attorney, Agent, or Firm*—Knobbe, Martens, Olson & Bear LLP

(57) ABSTRACT

The present invention relates generally to a Plasmid Maintenance System for the stabilization of expression plasmids encoding foreign antigens, and methods for making and using the Plasmid Maintenance System. The invention optimizes the maintenance of expression plasmids at two independent levels by: (1) removing sole dependence on balanced lethal maintenance systems; and (2) incorporating a plasmid partition system to prevent random segregation of expression vector plasmids, thereby enhancing their inheritance and stability. The Plasmid Maintenance System may be employed within a plasmid which has been recombinantly engineered to express a variety of expression products.

13 Claims, 22 Drawing Sheets

OTHER PUBLICATIONS

Figure 1B:
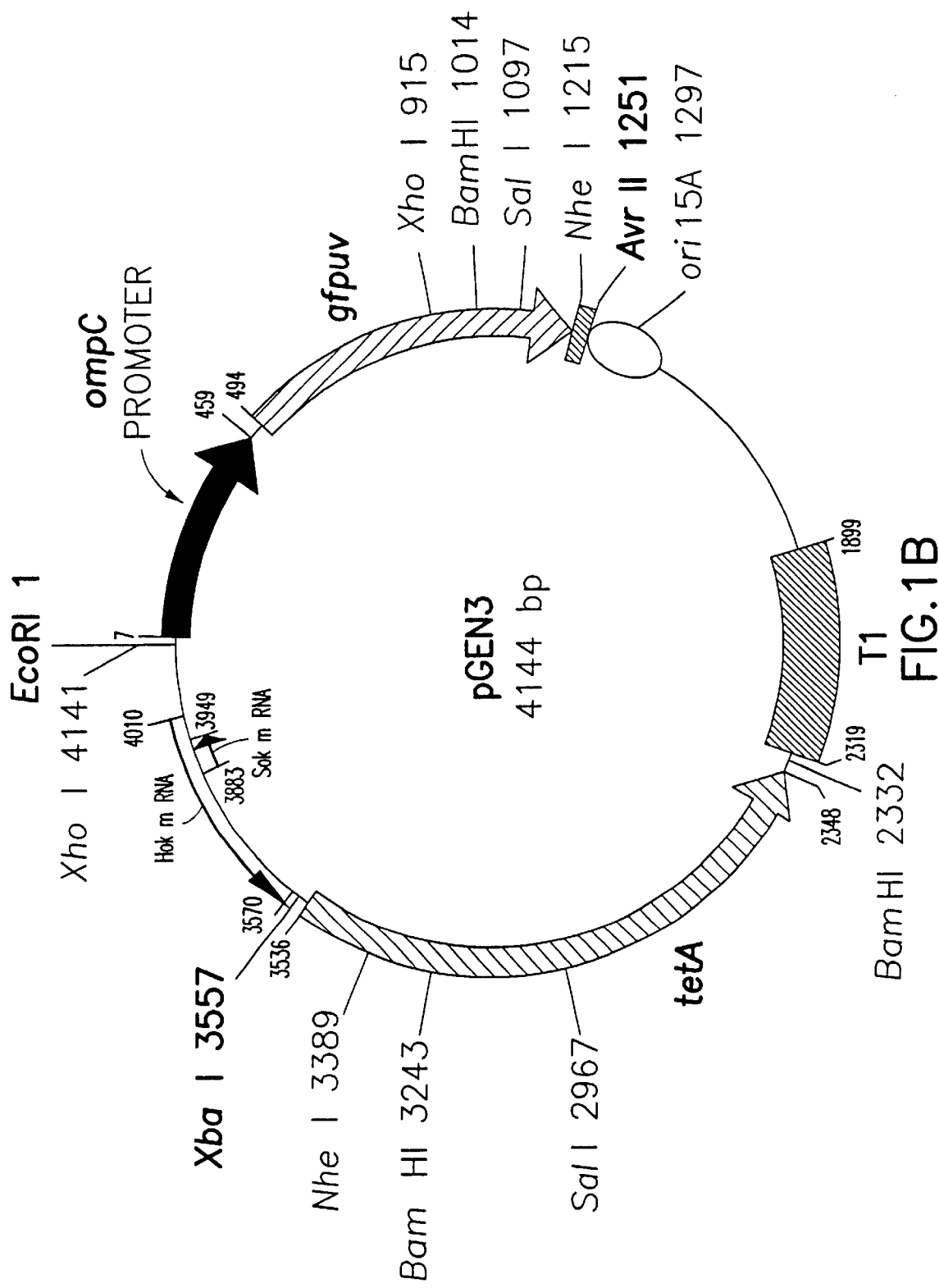

Ruiz–Echevarria et al., "The kis genes of the parD maintenance system of plasmid R1 form an operon that is auto-regulated at the level of transcription by the co-ordinated action of the Kis and Kid proteins", Molecular Microbiology, 1997 5 (11), pp. 2685–2693.

Ruiz–Echevarria et al., "Translational coupling and limited degradation of a polycistronic messenger modulate differential gene expression in the parD stability system of plasmid R1", Gen. Genet, 1995, 248, pp. 599–609.

Ruiz–Echevarria et al., "Kid, a Small Protein of the parD Stability System of Plasmid R1, is an Inhibitor of DNA Replication Acting at the Initiation of DNA Synthesis", J. Mol. Biol., 1995, 247, pp. 568 571.

Bravo et al., "Killing of Escherichia coli cells modulated by components of the stability system ParD of plasmid R1", Mol Gen Genet, 1988, 215, pp. 146–151.

Nordstrom et al., "Control of Replication of Bacterial Plasmids: Genetics, Molecular Biology, and Physiology of the Plasmid R1 System", Academic Press Inc., 1984, pp. 71–91.

Kurt Nordstrom and E. Gerhart H. Wagner, "Kinetic aspects of control of plasmid replication by antisense RNA", Biosci, Jul. 1994, pp. 294–300.

Kim Pedersen and Kenn Gerdes, "Multiple hok genes on the chromosome of Escherichia coli", Molecular Microbiology, 1999, 32 (50), pp. 1090–1102.

J. Dolfing et al., "Proposed New Nomenclature for SLT (VT) Family", ASM News, 62, (3), 1996, pp. 117–119.

Takeda et al.; "Bacterial Toxins and Virulence Factors in Disease", Handbook of Natural Toxins, 8, pp. 313–327, 1995.

Acheson et al., "Nomenclature of enterotoxins", The Lancet, 351, Apr. 4, 1998, pp. 1003.

Yaeta ENDO et al., "Site of action of a Vero toxin (VT2) from Escherichia coli O157:H7 and of Shiga toxin on eukaryotic ribosomes RNA N–glycosidase activity of the toxins", Eur. J. Biochem, 1988, 171, pp. 45–50.

Gerdes et al., "Unique type of plasmid maintenance function: Postsegragational killing of plasmid–free cells", Proc. Natl. Acad. Sci. USA, May 1986, 83, pp. 3116–3120.

Carlton Gyles, "Escherichia coli cytotoxins and enterotoxins", Can. J. Microbiol., 1992, 38, pp. 7323–746.

Matthew P. Jackson et al., "Nucleotide Sequence analysis and comparison of the structural genes for Shiga–like toxin I and Shiga–like toxin II encoded by bacteriophages from Escherichia coli 933", Federation of European Microbiological Societies, 1987, 44, pp. 109–114.

Vernon L. Tesh et al., "Comparison of the Relative Toxicities of Shiga–Like Toxins Type I and Type II for Mice", Infection and Immunity, Aug. 1993, 61 (8), pp. 3392–3402.

Susanne W. Lindgren et al., The Specific Activities of Shiga–Like Toxin Type II (SLT–11) and SLT–II–Related Toxins of Enterohemorrhagic Escherichia coli Differ When Measured by Vero Cell Cytotoxicity but Not by Mouse Lethality, Infection and Immunity, Feb. 1994, 62 (2), pp. 623–631.

Lawrence M. Sung et al., "Transcription of the Shiga–Like Toxin Type II and Shiga–Like Toxin II Variant Operons of Escherichia coli", Journal of Bacteriology, Nov. 1990, 172 (11), pp. 6386–6395.

Inge Muhldorfer et al., "Regulation of the Shiga–Like Toxin II Operon in Escherichia coli", Infection and Immunity, Feb. 1996, 64 (2), pp. 495–502.

Clare K. Schmitt, "Two Copies of Shiga–Like Toxin II–Related Genes Common in Enterohemorrhagic Escherichia coli Strains Are Responsible for the Antigenic Heterogeneity of the O157:H–Strain E32511", Infection and Immunity, Mar. 1991, 59 (3), pp. 1065–1073.

Debra L. Weinstein et al., "Cloning and Sequencing of a Shiga–Like Type II Variant from an Escherichia coli Strain Responsible for Edema Disease of Swine", Journal of Bacteriology, Sep. 1988, 170 (9), pp. 4223–1230.

C.L. Gyles et al., "Cloning and nucleotide sequence analysis of the genes determining verocytotoxin production in a porcine edema disease isolate of Escherichia coli", Microbial Pathologies, 1988, 5, pp. 419–426.

Adrienne W. Paton et al., "Comparative Toxicity and Virulence of Escherichia coli Clones Expressing Variant and Chimeric Shiga–Like Toxin Type II Operons", Infection and Immunity, Jul. 1995, 63 (7), pp. 2450–2458.

Adrienne W. Paton et al., "Polymerase chain reaction amplification, cloning and sequencing of variant Escherichia coli Shiga–like toxin type II operons", Microbial Pathogenesis, 1993, 15, pp. 77–82.

Hideaki Ito et al., "Cloning and nucleotide sequencing of Vero toxin 2 variant genes from Escherichia coli 091:H21 isolated from a patient with the hemoloytic uremic syndrome", Microbial Pathogenesis, 1990, 8, pp. 47–60.

Marie E. Fraser et al., "Crystal structure of the holotoxin from Shigella dysenteriae at 2.5 A resolution", Structural Biology, Jan. 1994, 1 (1), pp. 59–64.

Penolope E. Stein et al., "Crystal structure of the cell–binding B oligomer of verotoxin–1 from E. coli", Nature, Feb. 1992, 355, pp. 748–750.

Per–Georg et al., "Modelling of the interaction of verotoxin–1 (VT1) with its glycolipid receptor, globotriasylceramide ($GB_3$)", Int. J. Biol. Macromol., 1995, 17 (3–4), pp. 199–204.

Per–Georg et al., "Two distinct binding sites for globotriaosyl ceramide on verotoxins: identification by molecular modelling and confirmation using deoxy analogues and a new glycolipid receptor for all verotoxins", Chemistry & Biology, 1996, 3 (4), pp. 263–275.

Hong Ling et al., "Structure of the Shiga–like Toxin I B–Pentamer Complexed with an Analogue of Its Receptor $GB_3$", Bichemistry, 1998, 37, pp. 1777–1788.

Carolyn J. Hovde et al., "Evidence that glutamic acid 167 is an active–site residue of Shiga–like toxin I", Proc. Natl. Acad. Sci. USA, Apr. 1988, 85, pp. 2568–2572.

Shinji Yamasaki et al., "importance of arginine at position 170 of the A subunit of Vero toxin 1 produced by enterohemorrhagic Escherichia coli for toxin activity", Microbial Pathogenesis, 1991, 11, pp. 1–9.

Matthew P. Jackson et al., "Mutational Analysis of the Shiga Toxin and Shiga–Like Toxin II Enzymatic Subunits", Journal of Bacteriology, Jun. 1990, 172 (6), pp. 3346–3350.

V.M. Gordon et al., "An Enzymatic Mutant of shiga–Like Toxin II Variant Is a Vaccine Candidate for Edema Disease of Swine", Infection and Immunity, Feb. 1992, 60 (2), pp. 485–490.

B.T. Bosworth et al., "Vaccination with Genetically Modified Shiga–Like Toxin IIe Prevents Edema Disease in Swine", Infection and Immunity, Jan. 1996, 64 (1), pp. 55–60.

Matthew P. Jackson, "Functional Analysis of the Shiga Toxin and Shiga–Like Toxin Type II Variant binding Subunits by Using Site–Directed Mutagenesis", Journal of Bacteriology, Feb. 1990, 172 (20), pp. 653–658.

Clifford Clark, "Phenylalanine 30 plays an important role in receptor binding of verotoxin–1", Molecular Microbiology, 1996, 19 (4), pp. 891–899.

Darrin J. Bast, "Toxicity and Immunogenicity of a Verotoxin 1 Mutant with Reduced Globotriaosylceramide Receptor Binding in Rabbits", Infection and Immunity, Jun. 1997, 65 (6), pp. 2019–2028.

L.P. Perera et al, "Identification of Three Amino Acid Residues in the B Subunit of Shiga Toxin and Shiga–Like Toxin Type II That are Essential for Holotoxin Activity", Journal of Bacteriology, Feb. 1991, 173 (3), pp. 1151–1160.

L.P. Perera et al., "Mapping the Minimal Contiguous Gene Segment That Encodes Functionally Active Shiga–Like Toxin II", Infection and Immunity, Mar. 1991, 59 (3), pp. 829–835.

Frances Pouch Downes et al., "Affinity Purification and Characterization of Shiga–Like Toxin II and Production of Toxin–Specific Monoclonal Antibodies", Infection and Immunity, Aug. 1988, 56 (8), pp. 1926–1933.

Guo–Fu Su et al., "Construction of Stable LamB–shiga Toxin B Subunit Hybrids: Analysis of Expression in *Salmonella typhimurium* aroA Strains and Stimulation of B Subunit–Specific Mucosal and Serum Antibody Responses", Infection and Immunity, Aug. 1992, 60 (8), pp. 3345–3359.

Gue–fu Su et al., "Extracellular export of Shiga Toxin B–subunit/haemolysin A (C–terminus) fusion protein expressed in *Salmonella typhimurium* aro A–mutant and stimulation of B–subunit antibody responses in mice", Microbial Pathogenesis, 1992, 13, pp. 465–476.

Susan E. Richardson et al., "Experimental Verocytotoxemia in Rabbits", Infection and Immunity, Oct. 1992, 60 (10), pp. 4154–4167.

S. Nelson et al., "Biological activity of verocytotoxin (VT)2c and VT1/VT2c chimeras in the rabbit model", Elsevier Science, 1994, pp. 245–249.

M. Bielaszewska et al., "Localization of Intravenously Administered Verocytotoxins (Shiga–Like Toxins) 1 and 2 in Rabbits Immunized with Homologous and Heterologous Toxoids and Toxin Subunits", Infection and Immunity, Jul. 1997, 65 (7), pp. 2509–2516.

Stephen J. Streatfield et al., "Intermolecular interactions between the A and B subunits of heat–labile enterotoxin from *Escherichia coli* promote holotoxin assembly and stability in vivo", Proc. Natl. Acad. Sci. USA, Dec. 1992, 89, pp. 12140–12144.

David W.K. Acheson et al., "Protective Immunity to Shiga-Like Toxin I following Oral Immunization with ShigaLike Toxin I B–Subunit–Producing *Vibrio cholerae* CVD 103–HgR", Infection and Immunity, Jan. 1996, 64 (1), pp. 355–357.

Elizabeth A. Wadolkowski et al., "Acute Renal Tubular Necrosis and Death of Mice Orally Infected with *Escherichia coli* Strains That Produce Shiga–Like Toxin Type II", Infection and Immunity, Dec. 1990, 58 (12), pp. 3959–3965.

Diana Karpman et al, "The Role of Lipopolysaccharide and Shiga–like Toxin in a Mouse Model of *Escherichia coli* 0157:H7 Infection", The Journal of Infectious Diseases, 1997 175, pp. 611–620.

Chandra B. Louise and Tom G. Obrig, "Specific Interaction of *Escherichia coli* 0157:H7–Derived Shiga–like Toxin II with Human Renal Endothelial Cells", The Journal of Infectious Diseases, 1995, 172, pp. 1397–1401.

Beth Boyd and Clifford Lingwood, "Verotoxin Receptor Glycolipid in Human Renal Tissue", Nephron, 1989, pp. 207–210.

Carla Zoja et al., "Verotoxin glycolipid receptors determine the localization of microangiopathic process in rabbits given verotoxin–1", J Lab Clin Med., Aug. 1992, 120 (2), pp. 229–238.

J. Yu and J.B. Kaper, "Cloning and characterization of the eae gene of enterohaemorrhagic *Escherichia coli* 0157:H7", Molecular Microbiology, 1992 6 (3), pp. 411–417.

Timothy K. McDaniel et al., "A genetic locus of enterocyte effacement conserved among diverse enterobacterial pathogens", Proc. Natl. Acad. Sci. USA, Feb. 1995, 932, pp. 1664–1668.

Karen G. Jarvis et al., "Enteropathogenic *Escherichia coli* contains a putative type III secretion system necessary for the export of proteins involved in attaching and effacing lesion formation", Proc. Natl. Acad. Sci. USA, Aug. 1995, 92, pp. 7996–8000.

Karen G. Jarvis et al., "Secretion of Extracellular Proteins by Enterohemorrhagic *Escherichia coli* via a Putative Type III Secretion System", Infection and Immunity, Nov. 1996, 64 (11), pp. 4826–4829.

Titia K. Sixma et al., "Comparison of the B–Pentamers of Heat–Labile Enterotoxin and Verotoxin–1: Two Structures with Remarkable Similarity and Dissimilarity", Bichemistry, 1993, 32, pp. 191–198.

Marianne Mangeney et al., "Apoptosis Induced in Burkitt's Lymphoma Cells via Gb3/CD77, a Glycolipid Antigen[1]", Cancer Research, Nov. 1, 1993, 53, pp. 5314–5319.

Sylvia Franke et al., "Clonal Relatedness of Shiga–Like Toxin–Producing *Escherichia coli* O101 Strains of Human and Porcine Origin", Journal of Clinical Microbiology, Dec. 1995, 33 (12), pp. 3174–3178.

San–Hyun Kim et al., "Cloning and Sequence Analysis of Another Shiga–Like Toxin 11e Variant Gene (slt–llera) from an *Escherichia coli* R107 Strain Isonlated from Rabbit", Microbiol. Immunol., 1997, 41 (10), pp. 805–808.

Joan R. Butterton et al., "Coexpression of the B Subunit of Shiga Toxin 1 and EaeA from Enterohemorrhagic *Escherichia coli* in *Vibrio cholerae* Vaccine Strains", Isfection and Immunity, Jun. 1997, 65 (6), pp. 2127–2135.

Nataro and Kaper, "Enterohemorrhagic *E. coli*" and "Diarrheagenic *E. Coli",* American Society for Microbiology, 1998, 11, pp. 164–178.

Samir Taga et al., "Intracellular Signaling Events in CD77–Mediated Apoptosis of Burkitt S Lymphoma Cells", Blood, Oct. 1, 1997, 90 (7), pp. 2757–2767.

Judette E. Haddad et al., "Minimum Domain of the Shiga Toxin A Subunit Required for Enzymatic Activity", Journal of Bacteriology, Aug. 1993, 175 (16), pp. 4970–4978.

Victor P. J. Gannon et al., "Molecular cloning and nucleotide sequence of another variant of the *Escherichia coli* Shigalike toxin II family", Journal of General Microbiology, 1990, 136, pp. 1125–1135.

A.D. O'Brien et al., "Shiga Toxin: Biochemistry, Genetics, Mode of Action, and Role in Pathogenesis", Microbiology and Immunology, 1992, 180, pp. 66–93.

William Montfort et al., "The Three–dimensional Structure of Ricin at 2.8 A", The Journal of Biological Chemistry, Apr. 15, 1987, 262 (11), pp. 5398–5403.

Susanne W. Lindgren et al., "Virulence of Enterohemorrhagic *Escherichia coli* O91:H21 Clinical Isolates in an Orally Infected Mouse Model", Infection and Immunity, Sep. 1993, 61 (9), pp. 3832–3842.

Rasmussen, P.B., et al., "Genetic analysis of the parB+ locus of Plasmid R1", Mol. Gen. Genet., 1987, 209 (1), pp. 122–128.

Gerdes, K., et al., "Mechanism of post–segregational killing by the hok/sok system of plasmid R1:sok antisense RNA regulates formation of hok mRNA species correlated with killing of plasmid–free cells", Mol. Microbiol., 1990, 4 (11), pp. 1807–1818.

"Custom DNA/RNA Synthesis, Order Form", Fisher Scientific, DNA Name 5SHOK–TET2 Form No. 070697.

"Custom DNA/RNA Synthesis, Order Form", Fisher Scientific, DNA Name 3SHOK–TET2, Form No. 070967.

"Custom DNA/RNA Synthesis, Order Form", Fisher Scientific, DNA Name 3PDC–TET2, Form No. 070697.

"Custom DNA/RNA Synthesis, Order Form", Fisher Scientific, DNA Name 5PDC–TET2, Form No. 070697.

Thomas Thisted et al., "Mechanism of Post–segregational Killing: Secondary Structure Analysis of the Entire Hok mRNA from Plasmid R1 Suggests a Folds–back Structure that Prevents Translation and Antisense RNA Binding", J. Mol. Biol., 1995, pp. 859–873.

Thomas Thisted et al., "Mechanism of post–segregational killing: translation of Hok, srnB and Pnd mRNAs of plasmids R1, F and R483 is activated by 3'–end processing", The EMBO Journal, 1994, 13 (8), 1950–1959.

Summers, D.K., The Biology of Plasmids, 1996, pp. 65–91.

* cited by examiner

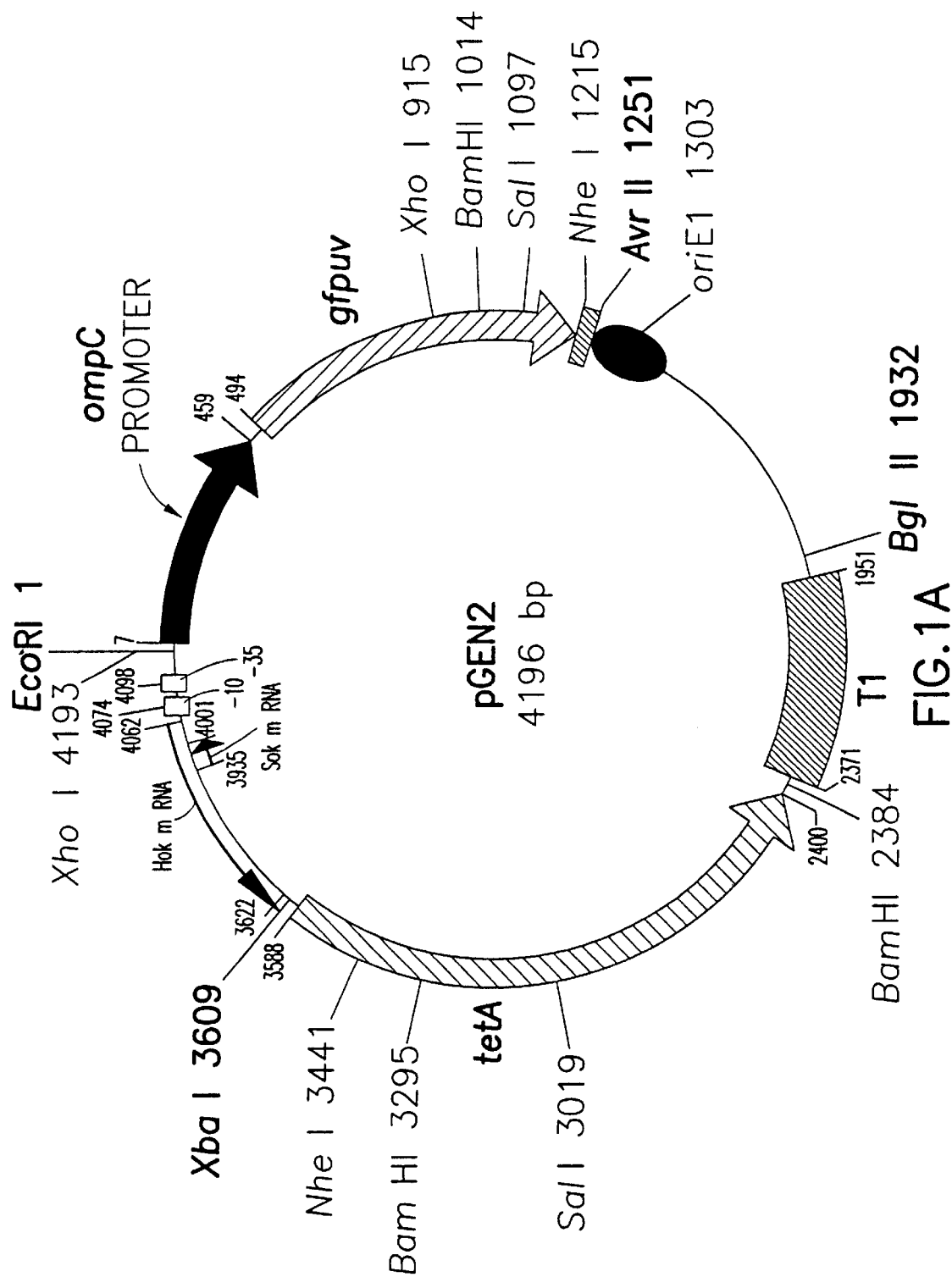

Figure 3F:
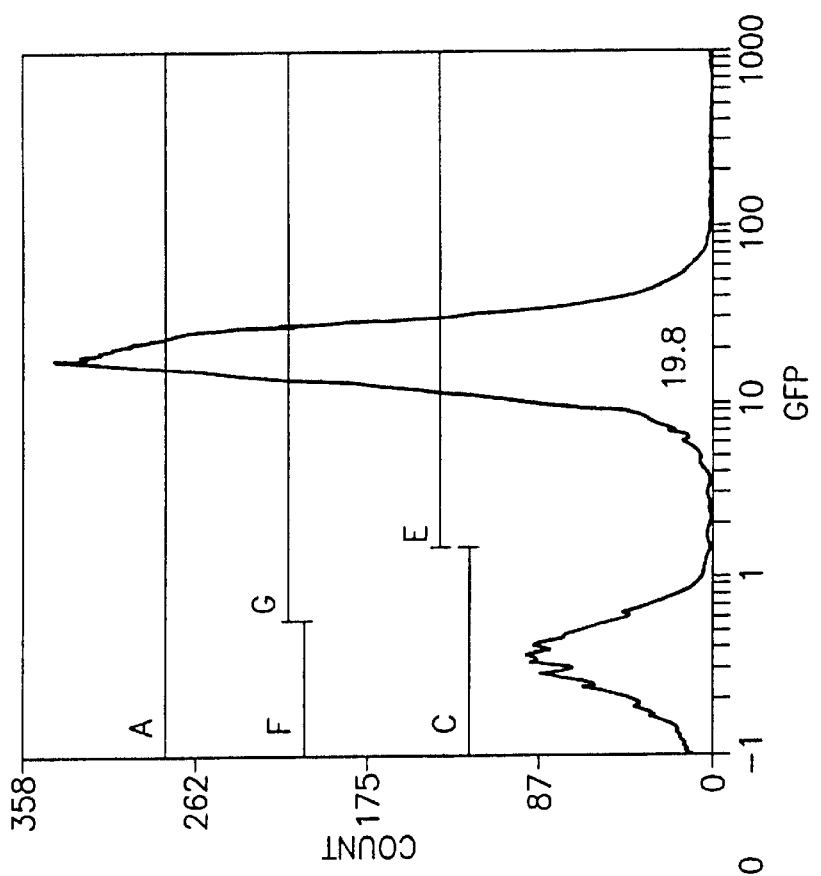

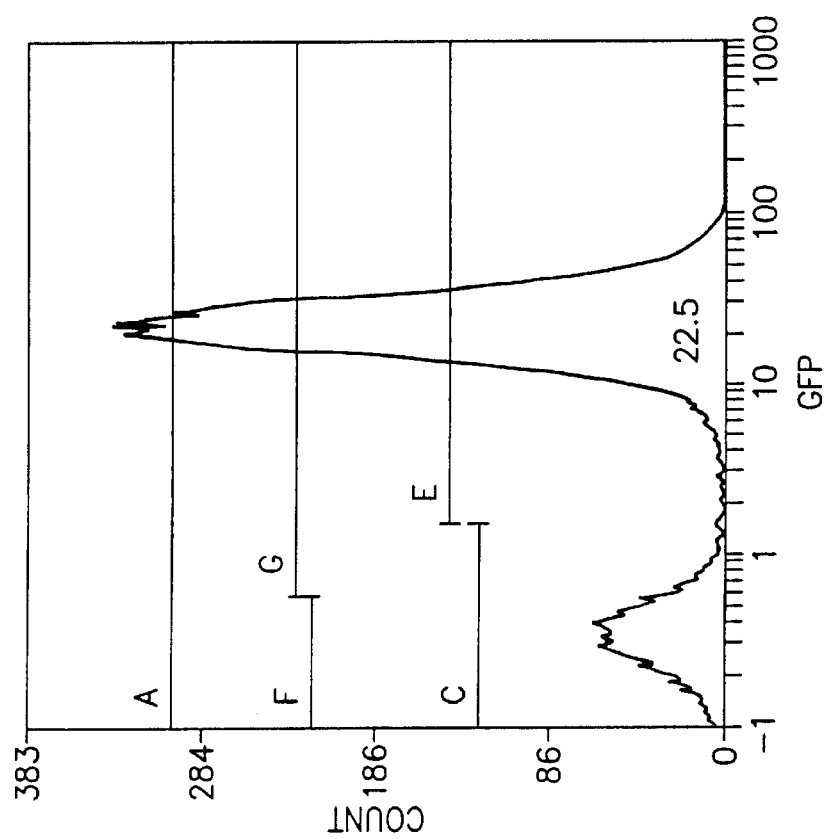
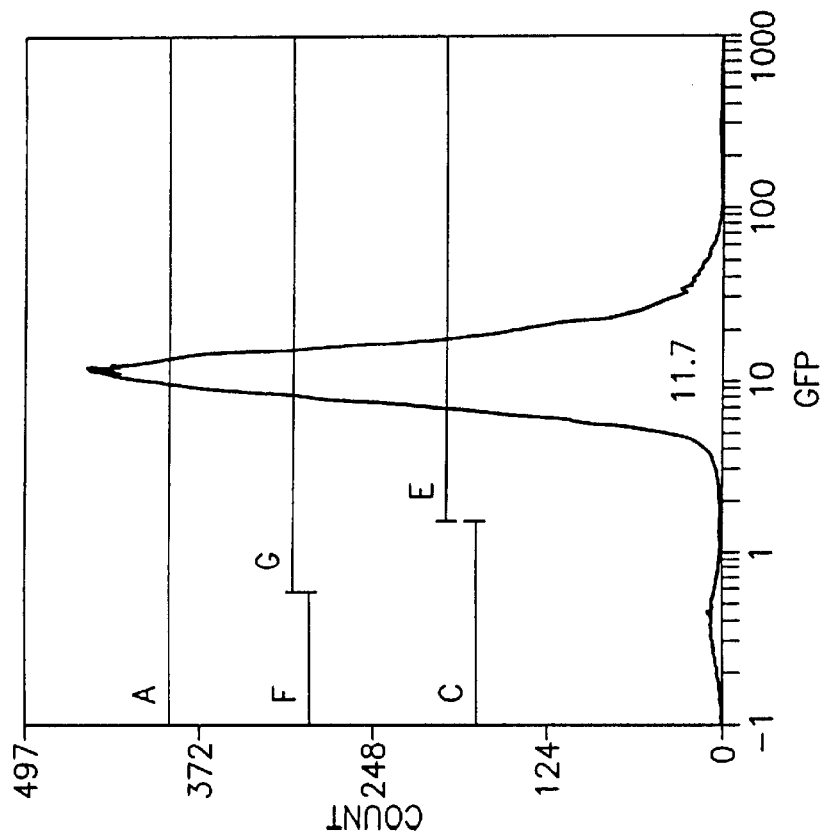
FIG.3B
FIG.3A

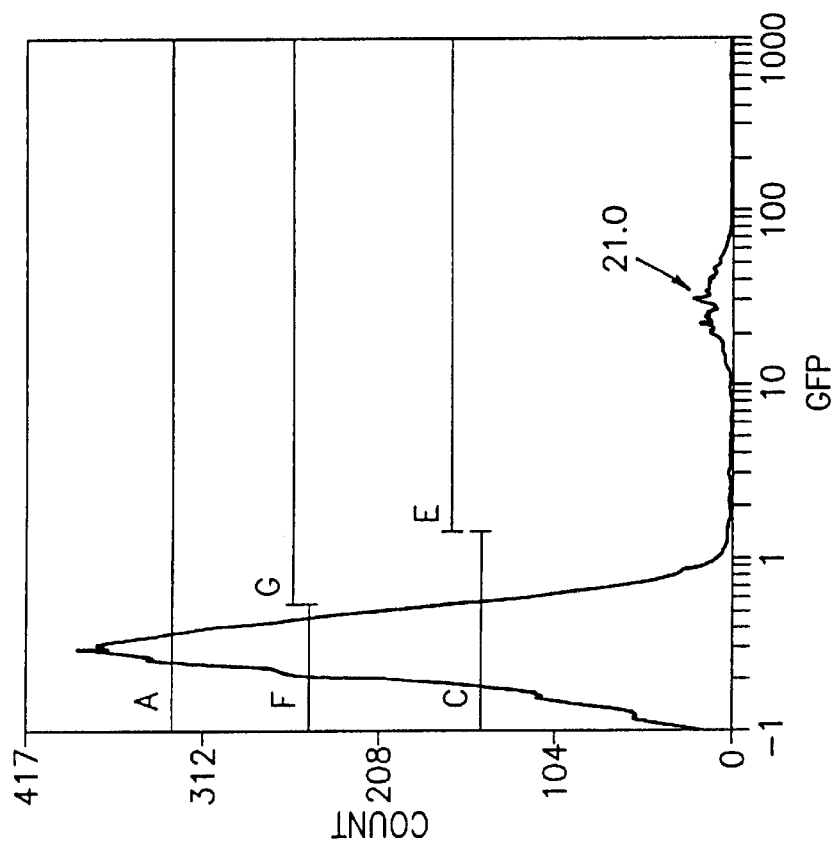
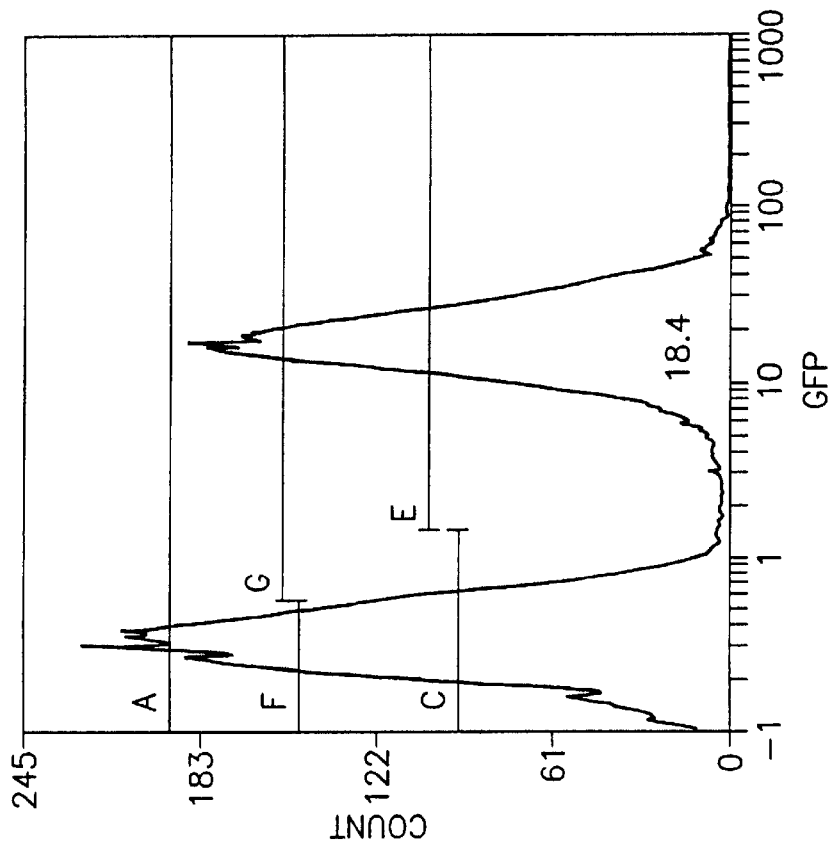

FIG. 4A

```
gaattctgtg gtagcacaga ataatgaaaa gtgtgtaaag aagggtaaaa aaaacgaat   60
gcgaggcatc cggttgaaat agggtaaac  agacattcag aaatgaatga cgtaataaa  120
taaagttaat gatgatagcg ggagttattc tagttggcag tgaagttttt gttttgacat  180
tcagtgctgt caaatactta agataagtt  attgatttta accttgaatt attattgctt  240
gatgttaggt gcttatttcg ccattcgca  ataatcttaa aagttccct  tgcattaca   300
ttttgaaaca tctatagga  taaatgaaac atcttaaaag ttttagtatc atattcgtgt  360
tggattattc tgcattttg  gggagaatgg acttgccgac tgattaatga gggttaatca  420
gtatgcagtg gcataaaaa  gcaaataaag gcatataaca gatgatctt  aaacatccac  480
aggagatat  ctgatgagta aaggagaga  actttttcact ggagttgtcc caattcttgt  540
tgaattagat ggtgatgtta atgggcacaa atttttctgtc agtggagagg gtgaaggtga  600
tgcaacatac ggaaactta  ccttaaatt  tatttgcact actgaaaac  tacctgttcc  660
atggccaaca cttgtcacta cttctctta  tggtgttcaa tgcttttcc  gttatccga   720
tcatatgaaa cggcatgact ttttcaagag gaaggttatg tacagaacg  aaggttatg   780
cactatatct ttcaagatg  acggaacta  caagacggt  gctgaagtca agtttgaagg  840
tgatacccct gttaatgta  togagttaa  agtattgat  tttaaagaag atggaaacat  900
tctcggacac aaactcgagt acaactataa ctcacacaat gtatacatca cggcagacaa  960
acaaaagaat ggaatcaaag ctaacttcaa aattcgccac aacattgaag atggatcgt  1020
tcaactagca gaccattatc aacaaatac  tccaattggc gatgcctg  tcttttacc   1080
```

```
agacaaccat tactgtgtga cacaatctgc cctttcgaaa gatccaacg aaaagggtga  1140
ccacatggtc cttcttgagt ttgtaactgc tgctggatt acacatggca tggatgagct  1200
ctacaaataa tgagctagcc cgctaatga ggcttt ttttctcggc ctagggcag  1260
caaaggcca ggaacgtaa aaggccgcg ttgctgggt tgccatag gctcgcccc  1320
cctgacgagc atcacaaaaa tcgacgctca agtcagaggt gcgaaacc gacagacta  1380
taaagataac aggcgttcc cctgaagc tcctcgtgc gctctcctgt tccgacctg  1440
ccgcttaccg gatacctgtc cgctttctc ccttcggaa ggtgggct ttctcatagc  1500
tcacgctgta ggtatctcag ttcggtgtag gtcgttcgct ccaagctggg ctgtgtgcac  1560
gaacccccg ttcagcccga ccgctggcc ttatccgta actatcgtct tgagtccaac  1620
ccggtaagac acgacttatc gccactggca gcagccactg gtaacaggat tagcagagcg  1680
aggtatgtag gcggtgctac agagttcttg aagtggtggc ctaactagg ctacactaga  1740
aggacagtat ttgtgtatctg cgctctgctg cctcggaaa cccttcggaaa aagagttggt  1800
agctccttgat cggcaaaca aaccacgct ggtagcggtg gtttttttgt ttgcaagcag  1860
cagattacgc gcagaaaaaa aggatctcaa gaagatcct tgatctttc tacgggtct  1920
gacgctcagt agatctaaaa cactaggcc aagagtttgt agaaaagcaa aaaggccatc  1980
gtcaggatg gccttctgct taatttgatg cctggcagtt tatggggc gtcctgccg  2040
ccaccctccg gcgtttgct tgcaacgtt caatcgct ccggggat ttgtctact  2100
caggagagcg ttcaccgaca acaacagat aaaacgaaag gcccagtctt tcgactgagc  2160
```

FIG. 4B

FIG. 4C

```
ctttgtttt atttgatgcc tgcagttcc ctactctgc atgggagac cccacactac 2220
catcgggct acggggttc acttctgagt tggcatggg gtcaggtggg accacggc   2280
tactgcgc  agccaattc  tgttttatca gacgcttct  ggttctgat  ttaatctgta 2340
tcaggctgaa aatctctct catcgccaa acagccaag ctgatcccc gatcttatca 2400
ggtcgaggtg gccggctcc atgcacggg agcacggg gggaggcaga caagtatag  2460
gggggct    acaatcatg  ccaaccgtt  ccatgtgctc gccgagggg cataaatcgc 2520
cgtgacgatc agggtccag tgatcgaagt taggctggta agagccgga gcgatccttg 2580
aagctgtcc  tgatggtcgt catctacctg cctgacagc  atggctcga  acgggggcat 2640
cccgatgccg cggaagcga gaagaatcat aatggggaag gccatccagc ctcggtcgc  2700
gaacgccagc aagacgtagc ccagccgtc gccgccatg cggcgataa tggctgctt   2760
ctcgccgaaa cgtttggtgg cggaccagt gacgaaggct tgagcgagg cgtgcaagat 2820
tcggaatacc gcaagcgaca ggcgatcat cgtcggctc cagcgaaagc gtcctcgcc   2880
gaaaatgacc cagagcctg cggcacctg tcctacgagt tgcatgataa agaagacagt 2940
cataagtgcg gcgacgatag ccggcaccg cgccacccg cggcactga ctggttgaa   3000
ggctctcaag ggcatcggtc gacgctctcc cttatcggac tcctcgatta ggaagcagc  3060
cagtagtagg ttgagccgt tgagcacgc cgccgcaagc aatggtgcat gcaaggagat 3120
ggggccaac agtcccccgg ccaggggc tgcaaccata ccaagccga aacaagct    3180
catgagccg aagtcgggcag ccgatctttc ccatcggtg atgtcgggca tataggcgcc 3240
```

```
agcaacagca cctgtgtggc oggtgatgcc ggccagatg gtoggggt agaggatcca 3300
caggacgggt gtggtcgcca tgatcggta gtcgatagtg gctccaagta ggaagcgag 3360
caggactggg cggcggcaa agggtcgga cagtgctccg agaagggtg cgcatagaaa 3420
ttgcatcaac gcatatagcg ctagcagcac gcatagtga ctggcatgc tgtcggaatg 3480
gacgatatcc cgcaagaggc cggcagtac cggcataacc cggcatatgc ctacagcatc 3540
cagggtgacg gtgccgagga tgacgatgag cgcattgtta gatttcattt ttttttcctc 3600
ctctattttct agacaacatc agcaaggaga aaggggctac cggcgaacca gcagccctt 3660
tataaagggg cttcagtagt cagaccagca tcagtcctga aaagggggc ctggccggc 3720
ctccagttg ctactaccg gattcgtaag ccatcgaaagc cgccactcc ctgtgtcgt 3780
ctctcgtaag aatctcgcac aggattttc gtgtcagata agtgaatatc aacagtgtga 3840
gacacacgat caacacacac aggataagg aacttcgtgg tagtttcatg gcttcttct 3900
cctttgcgcaa agggcgtaa gaggctatcc tgatgtggac tagacatagg gatgctcgt 3960
ggtggttaat gaaaattaac ttactacggg gctatcttct ttctgccaca caacaggca 4020
acaaaccacc ttcagtcat gaggcagaaa gctccaagcg cggcacat catagccat 4080
ataactgcac gctgaccaca ctcactttcc ctgaaaataa tcgctcatt cagacgttc 4140
acggaaatc cgtgtgattg ttgccgcatc agctgcctc cggagtttg tctcga 4196
```

FIG.4D

| | | | | |
|---|---|---|---|---|
| ctacaaataa | tgagctagcc | cgctaatga | ggggctttt | ttttctcggc | ctagagata | 60 |
| cttaacaggg | aagtgagagg | gcgcggcaa | agcgtttt | ccatagctc | cgccccctg | 120 |
| acaagcatca | cgaaatctga | cgctcaaatc | agtggtgggg | aaaccgaca | ggactataaa | 180 |
| gataccaggc | gtttccccct | ggggctccc | tcgtgcgctc | tcctgttcct | gcctttcggt | 240 |
| ttaccggtgt | cattccgctg | ttatgccgc | gtttgtctca | ttcagcct | gacactcagt | 300 |
| tcgggtagg | cagttgcgtc | caagctggac | tgtatgcaag | aacccccgt | tcagtccgac | 360 |
| cgctgcgcct | tatccgtaa | ctatcgtctt | gagtccaacc | cggaaagaca | tgcaaaagca | 420 |
| ccactggcag | cagccactgg | taattgattt | agaggagtta | gtcttgaagt | catggcgcgg | 480 |
| ttaaggctaa | actgaaagga | caagttttgg | tgactgcgct | cctccaagcc | agttacctcg | 540 |
| gttcaaagag | ttggtagctc | agagaacctc | cgaaaaccg | cctgcaagg | cggttttttc | 600 |

FIG.5A

```
gttttcagag caagagatta cggcagacc aaaagatct caagaagatc atcttattaa 660
tcagataaaa tatttctagg atctaaaaca ctagcccaa gagtttgtag aaacgcaaaa 720
aggccatccg tcaggatggc cttctgctta attgatgcc tggcagttta tggcggggt 780
cctgccgcc acctcggg cgttgcttc gcaagttca aatccgctcc cggggattt 840
gtcctactca ggagagcgtt cacgacaaa caacagataa aacgaaaggc ccagtctttc 900
gactgagct ttgtttat ttgatgctg gcagtccct actctcgat ggggagaccc 960
cacactacca tggggctac gggtttcac ttctgagttc tttatacaga caggtgggac 1020
cacgcgcta ctgcgcag gcaaattctg ttatcaga cgcttctgc gttctgattt 1080
aatctgtatc aggctgaaaa tcttctctca tcgccaaaa cagccaagct ggatcccga 1140
tcttatcagg tcgaggtggc ccggctccat gcacgggac gcaacggg gaggcag 1197
```

FIG.5B

```
ctacaaataa  tgagctagcc  cgctaatga   ggggctttt   ttttctcggc  ctagtttca    60
cctgttctat  taggtgttac  atgctgttca  tctgttacat  tgtcgatctg  ttcatggtga  120
acagctttaa  atgcaccaaa  aactcgtaaa  agctccgatg  tatctatctt  ttttacacg   180
ttttcatctg  tgcatatgga  cagttttccc  tttgatatct  aacggtgaac  agttgttcta  240
ctttgttg    ttagtcttga  tgcttcactg  atagatacaa  gagcataag   aacctcagat  300
cctttcgtat  ttagccagta  tgttctctag  tgtggttgt   tgttttgcg   tgagcatga   360
gaacgaacca  ttgagatcat  gcttacttg   catgtcactc  aaaattttg   cctcaaact   420
ggtgagctga  atttttgcag  ttaagcatc   gtgtagtgtt  tttcttagtc  cgttacgtag  480
gtaggaatct  gatgtaatgg  ttgttggtat  tttgtcacca  ttcatttta   tctgttgtt   540
ctcaagttcg  gttacgagat  ccattgtct   atctagttca  tttcatattg  tcaagtatc   600
agtgggggg   cctgcttat   caaccaccaa  tttttaaac   ctgtaagtgt  ttaatcttt   660
acttattggt  ttcaaaccc   attggttaag  ccttttaaac  tcatggtagt  tattttcaag  720
cattaacatg  aactaaatt   catcaaggct  aatctctata  tttgccttgt  gagttttctt  780
ttgtgttagt  tcttttaata  accactcata  aatctcata   gagtatttgt  tttcaaaaga  840
cttaacatgt  tcagattat   attttatgaa  ttttttaac   tggaaaagat  aaggcaatat  900
ctcttcacta  aaaactaatt  ctaattttc   gcttgagaac  tggcatagt   ttgtccactg  960
gaaaatctca  aagcctttaa  ccaaggatt   ccgatttcc   acagttctg   tcatcagctc 1020
tctggttgct  ttagctaata  caccataagc  atttccta    ctgatgttca  tcatctgagc 1080
```

FIG.6A

```
gtattggtta taagtgaacg atacgtccg ttcttcctt gtaggttttt caatgtggg 1140
gttgagtagt gccacacagc ataaaattag cttggtttca tgctccgtta agtcatagcg 1200
actaatcgct agttcatttg ctttgaaaac aactaattca gacatacatc tcaattggtc 1260
taggtgattt taatcactat accaattgag atggctagt caatgataat tactagtcct 1320
tttcctttga gttgtggta tctgtaaatt ctgctagacc tttgctggaa aacttgtaaa 1380
ttctgctaga ccctctgtaa attccgctag acctttgtgt gtttttttg tttatattca 1440
agtggttata atttatagaa taaagaaga ataaaaaag ataaaagaa tagatccag 1500
ccctgtgtat aactcactac tttagtcagt tcgcagtat tacaaaagga tgtcgcaaac 1560
gctgtttgct cctctacaaa acagacctta aaacctaaa ggcttaagta gcacctcgc 1620
aagctcgggc aaatcgctga atattccttt tgtctccgac catcaggcac ctgagtcgct 1680
gtcttttttg tgacattcag ttgctgcgc tcacgctct ggcagtgaat ggggtaaat 1740
ggcactacag gcgccttta tggattcatg caaggaaact accatacata caagaaagc 1800
ccgtcaaggg cttctcaggg cgttttatgg cggtctgct atgtggtgct atctgactttt 1860
ttgctgttca gcagttcctg cctctgatt ttccagtctg accacttcgg attatccgt 1920
```

FIG.6B

```
gacaggtcat tcagactggc taatgcaccc agtaaggcag cgtatcatc aacaggctta 1980
ccgtcttac tgtcaacggg atctaaaaca ctagcccaa gagtttgtag aaacgcaaaa 2040
aggccatccg tcaggatggc cttctgctta atttgatgcc tggcagttta tgcggggggt 2100
cctgccgcc acctcggg cgttgcttc gcaagttca atccgctcc cggggatttt 2160
gtcctactca ggagacggtt cacgacaaa caacagataa acgaaaggc ccagtctttc 2220
gactgagct ttgttttat ttgatgctg gcagtccct actctcgcat gggagaccc 2280
cacactacca tcggcgctac gggtttcac ttctgagttc ggcatggggt caggtgggac 2340
cacgcggcta ctgcgccag gcaaattctg ttttatcaga ccgcttctgc gttctgattt 2400
aatctgtatc aggctgaaaa tcttctctca tcgccaaagct cagccaagct ggatcccga 2460
tcttatcagg tcgagtggc ccggctccat gcaccggac gcaacgggg gaggcagaca 2520
aggtatagg cggcctac aatcatgcc aaccgttcc atgtgctgc cgagggca 2580
taaatcgccg tgacgatcag cggtccagtg atcgaagtta ggctggtaag agccgcgagc 2640
gatcctt                                                       2647
```

FIG.6C

```
ttgctgttca   gcagttcctg   ccctctgatt   ttccagtctg   accacttcgg   attatcccgt   3120
gacaggtcat   tcagactggc   taatgcaccc   agtaaggcag   cggtatcatc   aacaggctta   3180
ccgtcttac    tgtcaaccgg   atctaaaaca   ctaggcccaa   gagtttgtag   aaacgcaaaa   3240
aggccatccg   tcaggatggc   cttctgctta   atttgatgcc   tggcagttta   tggcgggcgt   3300
cctgcccgcc   acccctccgg   ccgttgcttc   gcaacgttca   aatccgctcc   cggcggattt   3360
gtcctactca   ggagagcgtt   caccgacaaa   caacagataa   aacgaaaggc   ccagtctttc   3420
gactgagcct   ttcgtttat    ttgatgcctg   gcagttccct   actctcgcat   ggggagaccc   3480
cacactacca   tcggcgctac   ggcgtttcac   ttctgagttc   ggcatggggt   caggtgggac   3540
caccgcgcta   ctgccgccag   gcaaattctg   ttttatcaga   ccgcttctgc   gttctgattt   3600
aggctgaaaa   tcntctctca   tccgccaaaa   cagccaagct   ggggatccc    3660
```

FIG. 6d

```
cgatcttatc aggtcgaggt ggcccggctc catgcaccgc gacgcaacgc ggggaggcag  3720
acaaggtata gggcggcgcc tacaatccat gccaacccgt tccatgtgct cgccgaggcg  3780
gcataaatcg ccgtgacgat cagcggtcca gtgatcgaag ttaggctggt aagagccgcg  3840
agcgatcctt                                                          3850
```

FIG. 6e

SEQUENCE LISTING

```
<160> NUMBER OF SEQ ID NOS:   7

<210> SEQ ID NO 1
<211> LENGTH: 4199
<212> TYPE: DNA
<213> ORGANISM: Artificial Sequence
<220> FEATURE:
<221> NAME/KEY: misc_feature
<222> LOCATION: ()..()
<223> OTHER INFORMATION: pGEN2 nucleotide sequence 1-4199

<400> SEQUENCE: 1
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcattttg gggagaatgg acttgccgac tgattaatga gggttaatca     420
gtatgcagtg gcataaaaaa gcaaataaag gcatataaca gatcgatctt aaacatccac     480
aggaggatat ctgatgagta aaggagaaga acttttcact ggagttgtcc caattcttgt     540
tgaattagat ggtgatgtta atgggcacaa attttctgtc agtggagagg gtgaaggtga     600
tgcaacatac ggaaaactta cccttaaatt tatttgcact actggaaaac tacctgttcc     660
atggccaaca cttgtcacta ctttctctta tggtgttcaa tgcttttccc gttatccgga     720
tcatatgaaa cggcatgact ttttcaagag tgccatgccc gaaggttatg tacaggaacg     780
cactatatct ttcaaagatg acgggaacta caagacgcgt gctgaagtca agtttgaagg     840
tgatacccct gttaatcgta tcgagttaaa aggtattgat tttaaagaag atggaaacat     900
tctcggacac aaactcgagt acaactataa ctcacacaat gtatacatca cggcagacaa     960
```

```
acaaaagaat ggaatcaaag ctaacttcaa aattcgccac aacattgaag atggatccgt   1020
tcaactagca gaccattatc aacaaaatac tccaattggc gatggccctg tccttttacc   1080
agacaaccat tacctgtcga cacaatctgc cctttcgaaa gatcccaacg aaaagcgtga   1140
ccacatggtc cttcttgagt ttgtaactgc tgctgggatt acacatggca tggatgagct   1200
ctacaaataa tgagctagcc cgcctaatga gcgggctttt ttttctcggc ctagggccag   1260
caaaaggcca ggaaccgtaa aaaggccgcg ttgctggcgt ttttccatag gctccgcccc   1320
cctgacgagc atcacaaaaa tcgacgctca agtcagaggt ggcgaaaccc gacaggacta   1380
taaagatacc aggcgtttcc ccctggaagc tccctcgtgc gctctcctgt tccgaccctg   1440
ccgcttaccg gatacctgtc cgcctttctc ccttcgggaa gcgtggcgct ttctcatagc   1500
tcacgctgta ggtatctcag ttcggtgtag gtcgttcgct ccaagctggg ctgtgtgcac   1560
gaaccccccg ttcagcccga ccgctgcgcc ttatccggta actatcgtct tgagtccaac   1620
ccggtaagac acgacttatc gccactggca gcagccactg gtaacaggat tagcagagcg   1680
aggtatgtag gcggtgctac agagttcttg aagtggtggc ctaactacgg ctacactaga   1740
aggacagtat ttggtatctg cgctctgctg aagccagtta ccttcggaaa aagagttggt   1800
agctcttgat ccggcaaaca aaccaccgct ggtagcggtg gtttttttgt ttgcaagcag   1860
cagattacgc gcagaaaaaa aggatctcaa gaagatcctt tgatcttttc tacggggtct   1920
gacgctcagt agatctaaaa cactaggccc aagagtttgt agaaacgcaa aaggccatc    1980 cgtcaggatg gccttctgct taatttgatg cctggcagtt tatggcgggc gtcctgcccg   2040
ccaccctccg ggccgttgct tcgcaacgtt caaatccgct cccggcggat ttgtcctact   2100
caggagagcg ttcaccgaca aacaacagat aaaacgaaag gcccagtctt tcgactgagc   2160
ctttcgtttt atttgatgcc tggcagttcc ctactctcgc atgggagac  cccacactac   2220 catcggcgct acgcgtttc  acttctgagt tcggcatggg gtcaggtggg accaccgcgc   2280
tactgccgcc aggcaaattc tgttttatca gaccgcttct gcgttctgat ttaatctgta   2340
tcaggctgaa aatcttctct catccgccaa aacagccaag ctgggggatc ccgatctta   2400 tcaggtcgag gtggcccggc tccatgcacc gcgacgcaac gcggggaggc agacaaggta   2460
tagggcggcc cctacaatcc atgccaaccc gttccatgtg ctcgccgagg cggcataaat   2520
cgccgtgacg atcagcggtc cagtgatcga agttaggctg gtaagagccg cgagcgatcc   2580
ttgaagctgt ccctgatggt cgtcatctac ctgcctggac agcatggcct gcaacgcggg   2640
catcccgatg ccgccggaag cgagaagaat cataatgggg aaggccatcc agcctcgcgt   2700
cgcgaacgcc agcaagacgt agcccagcgc gtcggccgcc atgccggcga taatggcctg   2760
cttctcgccg aaacgtttgg tggcgggacc agtgacgaag gcttgagcga gggcgtgcaa   2820
gattccgaat accgcaagcg acaggccgat catcgtcgcg ctccagcgaa agcggtcctc   2880
gccgaaaatg acccagagcg ctgccggcac ctgtcctacg agttgcatga taaagaagac   2940
agtcataagt gcggcgacga tagtcatgcc ccgcgcccac cggaaggagc tgactgggtt   3000
gaaggctctc aagggcatcg gtcgacgctc tcccttatgc gactcctgca ttaggaagca   3060
gcccagtagt aggttgaggc cgttgagcac cgccgccgca aggaatggtg catgcaagga   3120
gatggcgccc aacagtcccc cggccacggg gcctgccacc atacccacgc cgaaacaagc   3180
gctcatgagc ccgaagtggc gagcccgatc ttccccatcg tgatgtcgg  cgatataggc   3240 gccagcaacc gcacctgtgg cgccggtgat gccgccacg  atgcgtccgg cgtagaggat   3300
ccacaggacg ggtgtggtcg ccatgatcgc gtagtcgata gtggctccaa gtagcgaagc   3360
```

| | |
|---|---:|
| gagcaggact gggcggcggc caaagcggtc ggacagtgct ccgagaacgg gtgcgcatag | 3420 |
| aaattgcatc aacgcatata gcgctagcag cacgccatag tgactggcga tgctgtcgga | 3480 |
| atggacgata tcccgcaaga ggcccggcag taccggcata accaagccta tgcctacagc | 3540 |
| atccaggtg acggtgccga ggatgacgat gagcgcattg ttagatttca ttttttttc | 3600 |
| ctccttattt tctagacaac atcagcaagg agaaggggc taccggcgaa ccagcagccc | 3660 |
| ctttataaag gcgcttcagt agtcagacca gcatcagtcc tgaaaaggcg ggcctgcgcc | 3720 |
| cgcctccagg ttgctactta ccggattcgt aagccatgaa agccgccacc tccctgtgtc | 3780 |
| cgtctctgta acgaatctcg cacagcgatt ttcgtgtcag ataagtgaat atcaacagtg | 3840 |
| tgagacacac gatcaacaca caccagacaa gggaacttcg tggtagtttc atggccttct | 3900 |
| tctccttgcg caaagcgcgg taagaggcta tcctgatgtg gactagacat agggatgcct | 3960 |
| cgtggtggtt aatgaaaatt aacttactac ggggctatct tctttctgcc acacaacacg | 4020 |
| gcaacaaacc accttcacgt catgaggcag aaagcctcaa gcgccgggca catcatagcc | 4080 |
| catatacctg cacgctgacc acactcactt tccctgaaaa taatccgctc attcagaccg | 4140 |
| ttcacgggaa atccgtgtga ttgttgccgc atcacgctgc ctcccggagt ttgtctcga | 4199 |

<210> SEQ ID NO 2
<211> LENGTH: 1200
<212> TYPE: DNA
<213> ORGANISM: Artificial Sequence
<220> FEATURE:
<221> NAME/KEY: misc_feature
<222> LOCATION: ()..()
<223> OTHER INFORMATION: pGEN3 nucleotide sequence 1201-2397

<400> SEQUENCE: 2

| | |
|---|---:|
| ctacaaataa tgagctagcc cgcctaatga gcgggctttt ttttctcggc ctaggagata | 60 |
| cttaacaggg aagtgagagg gccgcggcaa agccgttttt ccataggctc cgcccccctg | 120 |
| acaagcatca cgaaatctga cgctcaaatc agtggtggcg aaacccgaca ggactataaa | 180 |
| gataccaggc gtttccccct ggcggctccc tcgtgcgctc tcctgttcct gcctttcggt | 240 |
| ttaccggtgt cattccgctg ttatggccgc gtttgtctca ttccacgcct gacactcagt | 300 |
| tccgggtagg cagttcgctc caagctggac tgtatgcacg aaccccccgt tcagtccgac | 360 |
| cgctgcgcct tatccggtaa ctatcgtctt gagtccaacc cggaaagaca tgcaaaagca | 420 |
| ccactggcag cagccactgg taattgattt agaggagtta gtcttgaagt catgcgccgg | 480 |
| ttaaggctaa actgaaagga caagttttgg tgactgcgct cctccaagcc agttacctcg | 540 |
| gttcaaagag ttggtagctc agagaaccct cgaaaaaccg ccctgcaagg cggttttttc | 600 |
| gttttcagag caagagatta gcgcagacc aaaacgatct caagaagatc atcttattaa | 660 |
| tcagataaaa tatttctagg atctaaaaca ctaggcccaa gagtttgtag aaacgcaaaa | 720 |
| aggccatccg tcaggatggc cttctgctta atttgatgcc tggcagttta tggcgggcgt | 780 |
| cctgcccgcc accctccggg ccgttgcttc gcaacgttca aatccgctcc cggcggattt | 840 |
| gtcctactca ggagagcgtt caccgacaaa caacagataa acgaaaggc ccagtctttc | 900 |
| gactgagcct tcgttttat ttgatgcctg gcagttccct actctcgcat ggggagaccc | 960 |
| cacactacca tcggcgctac ggcgtttcac ttctgagttc ggcatggggt caggtgggac | 1020 |
| caccgcgcta ctgccgccag gcaaattctg ttttatcaga ccgcttctgc gttctgattt | 1080 |
| aatctgtatc aggctgaaaa tcttctctca tccgccaaaa cagccaagct gggggatccc | 1140 | cgatcttatc aggtcgaggt ggcccggctc catgcaccgc gacgcaacgc ggggaggcag     1200

<210> SEQ ID NO 3
<211> LENGTH: 2650
<212> TYPE: DNA
<213> ORGANISM: Artificial Sequence
<220> FEATURE:
<221> NAME/KEY: misc_feature
<222> LOCATION: ()..()
<223> OTHER INFORMATION: pGEN4 nucleotide sequence 1201-3847

<400> SEQUENCE: 3
ctacaaataa tgagctagcc cgcctaatga gcgggctttt ttttctcggc ctaggtttca       60
cctgttctat taggtgttac atgctgttca tctgttacat tgtcgatctg ttcatggtga      120
acagctttaa atgcaccaaa actcgtaaa agctctgatg tatctatctt ttttacaccg       180
ttttcatctg tgcatatgga cagttttccc tttgatatct aacggtgaac agttgttcta      240
cttttgtttg ttagtcttga tgcttcactg atagatacaa gagccataag aacctcagat      300
ccttccgtat ttagccagta tgttctctag tgtggttcgt tgtttttgcg tgagccatga      360
gaacgaacca ttgagatcat gcttactttg catgtcactc aaaaattttg cctcaaaact      420
ggtgagctga attttttgcag ttaaagcatc gtgtagtgtt tttcttagtc cgttacgtag     480
gtaggaatct gatgtaatgg ttgttggtat tttgtcacca ttcattttta tctgttgtt      540
ctcaagttcg gttacgagat ccatttgtct atctagttca acttggaaaa tcaacgtatc      600
agtcgggcgg cctcgcttat caaccaccaa tttcatattg ctgtaagtgt ttaaatcttt      660
acttattggt ttcaaaaccc attggttaag cctttaaac tcatggtagt tattttcaag       720
cattaacatg aacttaaatt catcaaggct aatctctata tttgccttgt gagttttctt      780
ttgtgttagt tcttttaata accactcata aatcctcata gagtatttgt tttcaaaaga      840
cttaacatgt tccagattat atttttatgaa ttttttttaac tggaaaagat aaggcaatat    900
ctcttcacta aaactaatt ctaatttttc gcttgagaac ttggcatagt ttgtccactg       960
gaaaatctca aagcctttaa ccaaggatt cctgatttcc acagttctcg tcatcagctc      1020
tctggttgct ttagctaata caccataagc attttcccta ctgatgttca tcatctgagc     1080
gtattggtta taagtgaacg ataccgtccg ttctttcctt gtagggtttt caatcgtggg     1140
gttgagtagt gccacacagc ataaaattag cttggtttca tgctccgtta agtcatagcg     1200
actaatcgct agttcatttg ctttgaaaac aactaattca gacatacatc tcaattggtc     1260
taggtgattt taatcactat accaattgag atgggctagt caatgataat tactagtcct     1320
tttcctttga gttgtgggta tctgtaaatt ctgctagacc tttgctggaa aacttgtaaa     1380
ttctgctaga ccctctgtaa attccgctag accttttgtgt gttttttttg tttatattca    1440
agtggttata atttatagaa taagaaaga ataaaaaaag ataaaagaa tagatcccag       1500
ccctgtgtat aactcactac tttagtcagt tccgcagtat tacaaaagga tgtcgcaaac     1560
gctgtttgct cctctacaaa acagacctta aaaccctaaa ggcttaagta gcaccctcgc     1620
aagctcgggc aaatcgctga atattccttt tgtctccgac catcaggcac ctgagtcgct     1680
gtcttttcg tgacattcag ttcgctgcgc tcacggctct ggcagtgaat ggggtaaat       1740
ggcactacag gcgccttta tggattcatg caaggaaact acccataata caagaaaagc      1800
ccgtcacggg cttctcaggg cgttttatgg cgggtctgct atgtggtgct atctgacttt     1860
ttgctgttca gcagttcctg ccctctgatt ttccagtctg accacttcgg attatcccgt     1920
gacaggtcat tcagactggc taatgcaccc agtaaggcag cggtatcatc aacaggctta    1980

-continued

```
cccgtcttac tgtcaaccgg atctaaaaca ctaggcccaa gagtttgtag aaacgcaaaa    2040
aggccatccg tcaggatggc cttctgctta atttgatgcc tggcagttta tggcgggcgt    2100
cctgcccgcc accctccggg ccgttgcttc gcaacgttca aatccgctcc cggcggattt    2160
gtcctactca ggagagcgtt caccgacaaa caacagataa aacgaaaggc ccagtctttc    2220
gactgagcct ttcgttttat ttgatgcctg gcagttccct actctcgcat ggggagaccc    2280
cacactacca tcggcgctac ggcgtttcac ttctgagttc ggcatggggt caggtgggac    2340
caccgcgcta ctgccgccag gcaaattctg ttttatcaga ccgcttctgc gttctgattt    2400
aatctgtatc aggctgaaaa tcttctctca tccgccaaaa cagccaagct ggggatccc     2460 cgatcttatc aggtcgaggt ggcccggctc catgcaccgc gacgcaacgc ggggaggcag    2520
acaaggtata gggcggcgcc tacaatccat gccaacccgt tccatgtgct cgccgaggcg    2580
gcataaatcg ccgtgacgat cagcggtcca gtgatcgaag ttaggctggt aagagccgcg    2640
agcgatcctt                                                           2650
```

<210> SEQ ID NO 4
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: mutated Shiga toxin segment

<400> SEQUENCE: 4
acagcagacg cgtta                                                     15

<210> SEQ ID NO 5
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: mutated Shiga toxin segment

<400> SEQUENCE: 5
ctgaacctag ggcga                                                     15

<210> SEQ ID NO 6
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: mutated Shiga toxin segment

<400> SEQUENCE: 6
gaattcgcga ccagt                                                     15

<210> SEQ ID NO 7
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: mutated Shiga toxin segment -continued

```
<400> SEQUENCE: 7
gaatcagatt ctgga                                                    15
```

EXPRESSION PLASMIDS

The development of the present invention was supported by the University of Maryland, Baltimore, Md. and by funding from the National Institutes of Health under contract number NIH R01-AI29471. The United States Government has a non-exclusive, irrevocable, paid-up license to practice or have practiced for or on behalf of the Unites States the invention herein as provided for by the terms of the above mentioned contracts awarded by the United States Government.

TABLE OF CONTENTS

1. BACKGROUND OF THE INVENTION
1.1 Field of the Invention
1.2 Description of Related Art
1.2.1 Bacterial Live Vector Vaccines
1.2.2 Attenuated Salmonella typhi as a live vector strain
1.2.3 Plasmid Instability
1.2.4 Plasmid Stabilization Systems
1.2.5 Antibiotic Resistance
1.2.6 Segregational Plasmid Maintenance Functions
1.2.7 Post-Segregational Killing (PSK) Functions
   1.2.7.1 Proteic Maintenance System: The phd/doc System
   1.2.7.2 Antisense Maintenance System: The hok-sok System
   1.2.7.3 Balanced Lethal Systems

2. SUMMARY OF THE INVENTION
3. DEFINITIONS
4. BRIEF DESCRIPTION OF THE DRAWINGS
5. DETAILED DESCRIPTION OF THE INVENTION
5.1 Suicide Vectors
5.2 Plasmid-based Expression of Heterologous Antigens
5.3 Balanced Lethal Systems
5.4 Segregation Limitations
5.5 Catalytic Activity Limitations
5.6 The Non-Catalytic SSB PSK Function
5.7 Expression Plasmids and Self-Contained Genetic Cassettes
5.8 Components of the Antigen Expression and Replication Cassette
   5.8.1 Promoter
   5.8.2 Origin of Replication
   5.8.3 Expressed Protein or Peptide
   5.8.4 Heterologous Antigens
      5.8.4.1 The Shiga Toxin Family
   5.8.5 Site-Specific Mutagensis of Shiga Toxins
5.9 Pharmaceutical Formulations

6. EXAMPLES
6.1 pGen Structure
6.2 $P_{OmpC}$ Promoter
6.3 Modified OmpC Promoter
6.4 Origins of Replication and Selection Cassettes
6.5 The Hok-Sok Antisense Post-Segregational Killing Locus
6.6 Complementation-Based Killing System
6.7 Conclusions

7. REFERENCES
THE CLAIMS
ABSTRACT OF THE DISCLOSURE

1. BACKGROUND OF THE INVENTION

1.1 Field of the Invention

The present invention relates generally to expression plasmids stabilized by a Plasmid Maintenance System (as defined herein) capable of expressing a protein or peptide, such as an antigen for use in a live vector vaccine, and methods for making and using the stabilized plasmids. The invention optimizes the maintenance of expression plasmids at two independent levels by: (1) removing sole dependence on catalytic balanced lethal maintenance systems; and (2) incorporating a plasmid partition system to prevent random segregation of expression plasmids, thereby enhancing inheritance and stability.

1.2 Description of Related Art

Set forth below is a discussion of art relevant to the present invention.

1.2.1 Bacterial Live Vector Vaccines

Bacterial live vector vaccines represent an important and promising strategy in the field of vaccine development. These vaccines deliver antigens to a host immune system by expressing the antigens from genetic material contained within a bacterial live vector. The genetic material is typically a replicon, such as a plasmid. The antigens may include a wide variety of proteins and/or peptides of bacterial, viral, parasitic or other origin.

Among the bacterial live vectors currently under investigation are attenuated enteric pathogens (e.g., *Salmonella typhi*, Shigella, *Vibrio cholerae*), commensals (e.g., Lactobacillus, *Streptococcus gordonii*) and licensed vaccine strains (e.g., BCG). For the reasons discussed below, *S. typhi* is a particularly attractive candidate for human vaccination.

1.2.2 Attenuated *Salmonella typhi* as a Live Vector Strain

*S. typhi* is a well-tolerated live vector that can deliver multiple unrelated immunogenic antigens to the human immune system. *S. typhi* live vectors have been shown to elicit antibodies and a cellular immune response to expressed antigen. Examples of antigens successfully delivered by *S. typhi* include the non-toxigenic yet highly immunogenic fragment C of tetanus toxin and the malaria circumsporozoite protein from *Plasmodium falciparum*.

*S. typhi* is characterized by enteric routes of infection, a quality which can enable oral vaccine delivery. *S. typhi* also infects monocytes and macrophages and can therefore target antigens to professional APCs.

Expression of an antigen by *S. typhi* generally requires incorporation of a recombinant plasmid encoding the antigen. Consequently, plasmid stability is a key factor in the development of high quality attenuated vaccines with the ability to consistently express foreign antigens.

Attenuated *S. typhi* vaccine candidates for use in humans should possess at least two well separated and well defined mutations that independently cause attenuation, since the chance of in vitro reversion of such double mutants would be negligible.

The attenuated vaccine candidate *S. typhi* CVD908 possesses such properties. CVD908 contains two non-reverting deletion mutations within the aroC and aroD genes. These two genes encode enzymes critical in the biosynthetic pathway leading to synthesis of chorismate, the key precursor required for synthesis of the aromatic amino acids phenylalanine, tyrosine, and tryptophan. Chorismate is also required for the synthesis of p-aminobenzoic acid; after its conversion to tetrahydrofolate, p-aminobenzoic acid is converted to the purine nucleotides ATP and GTP.

1.2.3 Plasmid Instability

Plasmidless bacterial cells tend to accumulate more rapidly than cells containing active plasmids. Summers, *The*

*Biology of Plasmids,* 65–91, 1996 (incorporated herein by reference). One reason for this increased rate of accumulation is that the transcription and translation of plasmid genes imposes a metabolic burden which slows cell growth and gives plasmidless cells a competitive advantage. Furthermore, foreign plasmid gene products are sometimes toxic to the host cell.

Stable inheritance of plasmids is desirable in the field of attenuated bacterial live vector vaccines to ensure successful continued antigen production, as well as in commercial bioreactor operations in order to prevent bioreactor takeover by plasmidless cells.

Stable inheritance of a plasmid generally requires that: (1) the plasmid must replicate once each generation, (2) copy number deviations must be corrected, and (3) upon cell division, the products of replication must be distributed to both daughter cells. Summers, *The Biology of Plasmids,* 65–91, 1996 (the entire disclosure of which is incorporated herein by reference).

Although chromosomal integration of foreign genes confers stability to such sequences, the genetic manipulations involved can be difficult, and the drop in copy number of the heterologous gene often results in production of insufficient levels of heterologous antigen to ensure an optimal immune response. Introduction of heterologous genes onto multicopy plasmids maintained within a live vector strain is a natural solution to the copy number problem. Genetic manipulation of such plasmids for controlled expression of such heterologous genes is straightforward; however, resulting plasmids can become unstable in vivo, resulting in loss of these foreign genes.

1.2.4 Plasmid Stabilization Systems

In nature bacterial plasmids are often stably maintained. See Gerdes et al. *Annu. Rev. Genet.,* 31:1–31, 1997 (incorporated herein by reference). In some circumstances, stable maintenance may simply result from a high copy number. However, many proteins, such as antigens, which may be desirably produced by bacterial cells are toxic if produced in large amounts per cell. Therefore, it is desirable to provide stable lower copy number plasmids for use in bacterial cells.

Stable inheritance of naturally occurring lower copy number plasmids can depend on the presence of certain genetic systems which actively prevent the appearance of plasmid-free progeny. A recent review of plasmid stabilization systems can be found in Jensen et al. *Molecular Microbiol.* 17:205–210, 1995 (incorporated herein by reference).

1.2.5 Antibiotic Resistance

One means for stabilizing plasmids is to provide an antibiotic resistance gene on the plasmid and to grow the cells in antibiotic-enriched media. However, this method is subject to a number of difficulties. The antibiotic resistance approach is expensive, requiring the use of costly antibiotics and perhaps, more importantly, the use of antibiotics in conjunction with in vivo administration of vaccine vectors may promote the growth of antibiotic-resistant bacteria and is currently forbidden by the U.S. Food and Drug Administration.

In large-scale production applications, the use of antibiotics may impose other limitations. With respect to commercial bioreactors, antibiotic resistance mechanisms can degrade the antibiotic and permit a substantial population of plasmidless cells to persist in the culture. Such plasmidless cells are unproductive and decrease the output of the bioreactor.

There is therefore a need in the art for a plasmid stabilization system specifically designed for use in bacterial live vector vaccines which does not rely on antibiotic resistance, and preferably which is also useful in commercial bioreactor applications.

1.2.6 Segregational Plasmid Maintenance Functions

Stable lower copy number plasmids typically employ a partitioning function that actively distributes plasmid copies between daughter cells. Exemplary partitioning functions include, without limitation, systems of pSC101, the F factor, the P1 prophage, and IncFII drug resistance plasmids. Such functions are referred to herein as "SEG" functions.

1.2.7 Post-Segregational Killing (PSK) Functions

PSK plasmid maintenance functions typically employ a two component toxin-antitoxin system and generally operate as follows: The plasmid encodes both a toxin and an antitoxin. The antitoxins are less stable than the toxins, which tend to be quite stable. In a plasmidless daughter cell, the toxins and anti-toxins are no longer being produced; however, the less stable antitoxins quickly degrade, thereby freeing the toxin to kill the cell.

The toxins are generally small proteins and and the antitoxins are either small proteins (proteic systems such as phd/doc) or antisense RNAs which bind to the toxin-encoding mRNAs preventing their synthesis (antisense systems such as hok/sok).

Balanced lethal systems discussed below in Section 1.2.6.3 are an example of an artificial PSK function.

1.2.7.1 Proteic Maintenance System: The phd/doc System

In proteic PSK functions, both the toxin and antitoxin are synthesized from operons in which the gene encoding the antitoxin is upstream of the gene encoding the toxin. These operons autoregulate transcription levels, and synthesis of the encoded proteins is translationally coupled. The anti-toxin is generally synthesized in excess to ensure that toxin action is blocked. The unstable antitoxins are constantly degraded by host-encoded proteases, requiring constant synthesis of antitoxin to protect the cell. Upon loss of the plasmid, antitoxins are no longer produced and the existing antitoxins rapidly degrade. This frees the toxin to kill the host cell.

The phd/doc system is an example of a proteic PSK function. The phd/doc system occurs naturally within the temperate bacteriophage P1, which lysogenizes *Escherichia coli* as an ~100 kb plasmid. This maintenance locus encodes two small proteins: the toxic 126 amino acid Doc protein causes death on curing of the plasmid by an unknown mechanism, and the 73 amino acid Phd antitoxin prevents host death, presumably by binding to and blocking the action of Doc.

Phd and Doc are encoded by a single transcript in which the ATG start codon of the downstream doc gene overlaps by one base the TGA stop codon of the upstream phd gene. Expression of these two proteins is therefore translationally coupled, with Phd synthesis exceeding synthesis of the toxic Doc protein.

In addition, transcription of this operon is autoregulated at the level of transcription through the binding of a Phd-Doc protein complex to a site which blocks access of RNA polymerase to the promoter of the operon as concentrations of both proteins reach a critical level. Although Doc appears to be relatively resistant to proteolytic attack, Phd is highly susceptible to cleavage. The PSK mechanism of a plasmid-encoded phd-doc locus is therefore activated when bacteria spontaneously lose this resident plasmid, leading to degradation of the Phd antitoxin and subsequent activation of the Doc toxin which causes cell death.

1.2.7.2 Antisense Maintenance System: The hok-sok System

In antisense maintenance systems, the antitoxins are antisense RNAs that inhibit translation of toxin-encoding mRNAs. Like the antitoxin peptides, the antisense RNAs are less stable than the toxin-encoding mRNA. Loss of the plasmid permits existing antitoxins to degrade, thereby permitting synthesis of the toxin which kills the host cell.

An example of an antisense maintenance system is the hok-sok system, encoded by the parB locus of plasmid R1. See Thisted et al., *J. Mol. Biol.* 247:859–873, 1995 (incorporated herein by reference). The system is comprised of three genes: hok, sok and mok.

Hok is a membrane-associated protein which irreversibly damages the cell membrane, killing host cells. Expression of Hoc from hok mRNA leads to a loss of cell membrane potential, arrest of respiration, changes in cell morphology, and death.

The sok gene encodes a trans-acting RNA which blocks translation of hok mRNA, thereby preventing Hoc killing of host cells. The sok RNA is less stable than hok mRNA and is expressed from a relatively weak promoter. Gerdes et al. *Annu. Rev. Genet.*, 31:1–31, 1997. The mechanism by which sok RNA blocks translation of Hok in plasmid-containing cells became apparent only after the identification of mok (modulation of killing), a third gene in the parB locus. The mok open reading frame overlaps with hok, and is necessary for expression and regulation of hok translation.

The sok antisense RNA forms a duplex with the 5' end of the mok-hok message rendering the mok ribosome binding site inaccessible to ribosomes and promoting RNase III cleavage and degradation of the mRNA. In the absence of mok translation, hok is not expressed from intact message, even though its own ribosome binding site is not directly obscured by sok RNA.

When a plasmid-free cell is formed, the unstable sok RNA decays much more rapidly than the stable mok-hok message. When the protection afforded by sok is lost, Mok and Hok are translated and the cell dies.

The difficulty with the hok-sok system is that a significant number of plasmidless cells can arise even when the hok-sok system is operative.

1.2.7.3 Balanced Lethal Systems

In a balanced-lethal system (a PSK function), a chromosomal gene encoding an essential structural protein or enzyme is deleted from the bacterial chromosome or is mutated such that the gene can no longer operate. The removed or damaged gene is then replaced by a plasmid comprising a fully operating gene and a nucleotide sequence encoding the protein or peptide of interest, e.g., an antigen. Loss of the plasmid results in an insufficiency of the essential protein and the death of the plasmidless cell.

A balanced-lethal system has been successfully employed in *S. typhimurium* based on expression of the asd gene encoding aspartate β-semialdehyde dehydrogenase (Asd). Asd is a critical enzyme involved in the synthesis of L-aspartic-β-semialdehyde, which is a precursor essential for the synthesis of the amino acids L-threonine (and L-isoleucine), L-methionine, and L-lysine, as well as diaminopimelic acid, a key structural component essential to the formation of the cell wall in Gram-negative bacteria. Loss of plasmids encoding such a critical enzyme would be lethal for any bacterium incapable of synthesizing Asd from the chromosome, and would result in lysis of the bacterium due to an inability to correctly assemble the peptidoglycan layer of its cell wall.

The asd system (a PSK function) has been successfully employed in attenuated *S. typhimurium*-based live vector strains for immunization of mice with a variety of procaryotic and eucaryotic antigens including such diverse antigens as detoxified tetanus toxin fragment C and the LT enterotoxin, synthetic hepatitis B viral peptides, and gamete-specific antigens such as the human sperm antigen SP10.

Murine mucosal immunization with these live vector strains has elicited significant immune responses involving serum IgG and secretory IgA responses at mucosal surfaces.

The asd system has recently been introduced into attenuated *Salmonella typhi* vaccine strains in an attempt to increase the stability of plasmids expressing synthetic hepatitis B viral peptides. However, when volunteers were immunized with these live vector strains, no immune response to the foreign antigen was detected. In fact, to date, few reports have documented an immune response to plasmid-based expression of a foreign antigen from stabilized plasmids after human vaccination with an attenuated *S. typhi* live vector.

In one report, the vaccine strain Ty21a was made auxotrophic for thymine by selecting in the presence of trimethoprim for an undefined mutation in the thyA gene, encoding thymidylate synthetase. Although in some cases failure of live vector strains may have resulted from over-attenuation of the strain itself, it appears probable that current killing systems for plasmids suffer from additional limitations.

Those situations where the chromosomal copy of the gene has been inactivated, rather than removed, may allow for restoration of the chromosomal copy via homologous recombination with the plasmid-borne gene copy if the bacterial strain utilized is recombination-proficient.

Balanced-lethal systems based on catalytic enzyme production are subject to a number of important deficiencies. In particular, since complementation of the chromosomal gene deletion requires only a single gene copy, it is inherently difficult to maintain more than a few copies of an expression plasmid. The plasmidless host strain must be grown on special media to chemically complement the existing metabolic deficiency.

Plasmidless cells may also benefit from "cross-feeding" effects when a diffusible growth factor is growth limiting.

There is therefore a need in the art for a Plasmid Maintenance System which is not solely reliant on a balanced lethal system, particularly for use in bacterial live vector vaccines.

2. SUMMARY OF THE INVENTION

The present invention relates generally to a stabilized expression plasmid which carries a Plasmid Maintenance System and a nucleotide sequence encoding a protein or peptide, such as a foreign antigen, and methods for making and using the stabilized expression plasmids.

In a particular aspect, the stabilized expression plasmid is employed in a *Salmonella typhi* live vector vaccine, such as the strain CVD908-htrA.

The invention optimizes the maintenance of expression plasmids at two independent levels by: (1) removing sole dependence on balanced lethal maintenance systems; and (2) incorporating a plasmid partition system to prevent random segregation of expression vector plasmids, thereby enhancing their inheritance and stability. In one aspect of the invention, the stabilized expression plasmid is recombinantly engineered to express one or more antigens, preferably one or more Shiga toxin 2 (Stx2) antigens, such as Shiga toxin subunit pentamers or a genetically detoxified Stx 2.

The stabilized expression plasmid preferably comprises one or more non-catalytic Plasmid Maintenance Functions.

In another aspect, the expression plasmid comprises a Plasmid Maintenance System which comprises at least one PSK function and at least one SEG function. For example, the Plasmid Maintenance System may comprise a two-component Plasmid Maintenance System comprising one PSK function and one SEG function. Alternatively, the Plasmid Maintenance System may comprise a three-component Plasmid Maintenance System comprising a PSK function, a SEG function and another Plasmid Maintenance Function. In a preferred alternative, the Plasmid Maintenance System comprises hok-sok+par+parA.

The Plasmid Maintenance Systems can be incorporated into multicopy expression plasmids encoding one or more proteins or peptides of interest. Such multicopy expression plasmids produce a gene dosage effect which enhances the level of expression of the protein or peptide of interest. Where the Plasmid Maintenance System is to be employed in a bacterial live vector vaccine, the protein or peptide of interest is one or more foreign antigens.

In one aspect, the expression plasmid is a vaccine expression plasmid comprising a Plasmid Maintenance System and at least one antigen, for example, at least one Shiga toxin 2 (Stx2) antigen. Where the antigen is a Shiga toxin 2 antigen, the Shiga toxin 2 antigen can, for example, be either a B subunit pentamer or a genetically detoxified Stx 2.

In another aspect the expression plasmid comprises a Plasmid Maintenance System which incorporates the ssb balanced lethal system and the ssb locus of the bacterial live vector has been inactivated using a suicide vector comprising a temperature sensitive origin of replication. In one aspect, the bacterial live vector is S. typhi and the suicide vectors are used to inactivate the ssb locus of S. typhi. In one aspect, the suicide vector is a derivative of pSC101 which carries sacB, described herein.

In another aspect, the present invention provides a Plasmid Maintenance System incorporating a PSK function involving a silent plasmid addiction system based on antisense RNA control mechanisms that only synthesize lethal proteins after plasmid loss has occurred.

In one aspect the expression plasmid comprises a series of expression plasmids, each comprising self-contained genetic cassettes encoding regulated expression of a heterologous antigen, an origin of replication, and a selectable marker for recovering the plasmid.

In one aspect the expression plasmid comprises a Plasmid Maintenance System which incorporates a PSK function based on the ssb gene. In a related aspect, mutated alleles such as ssb-1, described herein, are incorporated into the expression plasmids to enhance higher copy number plasmids by overexpression of SSB1-like proteins to form the required biologically active tetramers of SSB.

In another aspect, the expression plasmid comprises a promoter. The promoter is preferably an inducible promoter, such as the ompC promoter. In one aspect, the inducible promoter is the mutated $P_{ompC1}$ promoter described herein.

In one aspect, the expression plasmid of the present invention comprises a plasmid inheritance (or partition) locus; an origin of replication selected to provide copy number which effectively stabilizes a given antigen; a PSK function; and a nucleotide sequence encoding an antigen and a promoter which controls translation of the antigen and has a strength which is selected to improve antigen production without killing the cell.

The present invention also provides a method of using the expression plasmid comprising transforming a bacterial cell using said expression plasmid, and culturing the bacterial cell to produce the protein or peptide (e.g., the antigen), and/or administering said transformed cell or cell culture to a subject. Where the transformed bacterial cells are administered to a subject, they are administered in an amount necessary to elicit an immune response which confers immunity to the subject for the protein or peptide. The subject is preferably a human, but may also be another animal, such as a dog, horse, or chicken.

In one aspect, an expression plasmid is provided which comprises at least 3 independently functioning expression cassettes wherein one cassette encodes a protein or peptide of interest and the remaining cassettes each encode a different Plasmid Maintenance Function.

In one aspect, an expression plasmid is provided which encodes (1) a test antigen operably linked to a promoter and (2) a Plasmid Maintenance System.

In another aspect, a regulated test antigen expression cassette is provided which operates such that as induction of antigen expression is increased, a metabolic burden is placed on the bacterium which leads phenotypically to plasmid instability, i.e. a selective advantage is created for all bacteria which can spontaneously lose the offending plasmid. The test antigen can be the green fluorescent protein (GFP). The expression cassette encoding the test antigen can also comprise an inducible promoter, such as the ompC promoter, positioned such that the inducible promoter drives the translation of the test antigen.

In one aspect, a method of making an expression plasmid is provided which comprises synthesizing an expression plasmid comprising at least 3 independently functioning expression cassettes wherein one cassette encodes a protein or peptide of interest and the remaining cassettes each encode a different Plasmid Maintenance Function.

In one aspect, a method of screening Plasmid Maintenance Systems is provided comprising: providing one expression cassette which encodes a protein or peptide of interest, and at least two other expression cassettes, each encoding and capable of expressing in the host bacterial live vector a different Plasmid Maintenance Function; inserting the three expression cassettes into a single expression plasmid; transforming a bacterial live vector with the single expression plasmid; culturing the transformed bacterial live vector; and determining the rate of introduction of plasmid-less cells into the culture.

In one aspect, the present invention comprises an attenuated bacterial live vector vaccine comprising an attenuated bacterial live vector which has been transformed with a stabilized expression plasmid comprising a Plasmid Maintenance System, preferably a non-catalytic plasmid maintenance system.

In one aspect, the present invention comprises an attenuated bacterial live vector vaccine comprising an attenuated bacterial live vector which has been transformed with an expression plasmid comprising a Plasmid Maintenance System which incorporates at least one PSK system and one SEG system. The attenuated bacterial live vector can, for example, be S. typhi CVD908-htrA.

The present invention also provides a method for vaccinating a subject comprising administering to the subject an amount of a bacterial live vector vaccine sufficient to elicit an immunity-enhancing immune response. The present invention also provides a method for preventing a disease by vaccinating a subject using an amount of such bacterial live vector sufficient to elicit an immune response to one or more pathogens of such disease. The subject is preferably a human but may also be another animal, such as a horse, cow or pig. For example, the present invention provides a method for preventing hemolytic uremic syndrome (HUS) caused by Shiga toxin 2-producing enterohemorrhagic *Escherichia coli* by administering to a subject an amount of a bacterial live vector transformed with a stabilized plasmid encoding at least one Shiga toxin 2 antigen.

In another aspect, the present invention provides a method for screening Plasmid Maintenance Systems for efficacy, the method comprising: providing expression plasmids comprising the Plasmid Maintenance Systems described herein and encoding for a protein or peptide of interest, said expression plasmids having copy numbers which vary from low copy number (i.e. ~5 copies per cell) to medium copy number (~15 copies per cell) to high copy number (~60 copies per cell); transforming bacterial live vectors with such expression plasmids; and testing for rate of introduction of plasmidless cells and/or rate of growth of plasmid-containing cells. The modified origins of replication may be origins of replication from the plasmids pSC101 (low copy number), pACYC184 (medium copy number), and pAT153 (high copy number). Independently functioning plasmid replication cassettes can be utilized which permit testing of the efficiency of one or more plasmid stabilization systems as copy number is increased.

In another aspect, the present invention provides stabilized expression plasmids for use in attenuated *S. typhi* live vectors which contain a selectable marker which can readily be replaced by a non-drug resistant locus or by a gene encoding an acceptable drug resistance marker such as aph encoding resistance to the aminoglycosides kanamycin and neomycin.

The constructs of the present invention provide improved stability of recombinant plasmids, overcoming prior art problems of plasmid instability, for example, in bioreactor and live vector vaccination uses. The plasmids of the present invention are specifically tailored for vaccine applications though such plasmids are also useful in large scale protein production.

The plasmids of the present invention are a major improvement over the prior art in that they overcome the problems associated with plasmidless takeover and plasmid instability and have wide ranging utility in fields such as commercial protein production and attenuated bacterial live vector vaccine production.

There has long been a need for a solution to the problems of plasmidless takeover and plasmid stability associated with the field of vaccine delivery and protein production. The present invention is a major step toward the satisfaction of this need.

3. DEFINITIONS

The term "Plasmid Maintenance System" ("PMS") as used herein refers to a nucleotide sequence comprising at least one post-segregational killing function ("PSK") and at least one partitioning or segregating system ("SEG").

The term "Plasmid Maintenance Function" is used herein to refer to any function associated with a PMS.

The term "Post-Segregational Killing System" (PSK) is used herein to refer to any function which results in the death of any newly divided cell which does not inherit the plasmid of interest, and specifically includes balanced-lethal systems such as asd or ssb, proteic systems such as phd/doc and antisense systems such as hok-sok.

The terms "Segregating System" and/or "Partitioning System" (both referred to herein as "SEG") are used interchangeably herein to refer to any Plasmid Maintenance function that operates to increase the frequency of successful delivery of a plasmid to each newly divided cell, as compared to the frequency of delivery of a corresponding plasmid without such a SEG system. SEG systems include, for example, equipartitioning systems, pair-site partitioning systems, and the par locus of SC101.

The term "detoxified" is used herein to describe a toxin having one or more point mutations which render the toxin non-toxic versus a corresponding toxin without such point mutations.

The term "immunizingly effective" is used herein to refer to an immune response which confers upon the subject of such immune response a degree of immunological cellular memory with the effect that a secondary response (to the same or a similar toxin) is characterized by one or more of the following characteristics: shorter lag phase in comparison to the lag phase resulting from a corresponding exposure in the absence of immunization, production of antibody which continues for a longer period than production of antibody for a corresponding exposure in the absence of such immunization, a change in the type and quality of antibody produced in comparison to the type and quality of antibody produced from such an exposure in the absence of immunization, a shift in class response, with IgG antibodies appearing in higher concentrations and with greater persistence than IgM, an increased average affinity (binding constant) of the antibodies for the antigen in comparison with the average affinity of antibodies for the antigen from such an exposure in the absence of immunization, and/or other characteristics known in the art to characterize a secondary immune response.

4. BRIEF DESCRIPTION OF THE DRAWINGS

FIGS. 1A, 1B and 1C: Genetic maps of exemplary pGEN expression plasmids (pGEN2, pGEN3, and pGEN4) of the present invention.

FIGS. 2A, 2B, 2C and 2D: Genetic maps of exemplary expression plasmids (pJN72, pJN51, pJN10, and pJN12) of the present invention.

FIGS. 3A–H: Flow cytometry histograms of GFP flourescence for CVD 908htrA carrying expression vectors with the hok-sok post-segregational killing system.

FIGS. 4*a–d*: pGEN2 (SEQ. ID. NO.1) nucleotide sequence 1–4199.

FIGS. 5*a–b*: pGEN3 (SEQ. ID. NO.2) nucleotide sequence 1201–2400 showing the sequence of ori15A.

FIGS. 6*a–e*: pGEN4 (SEQ. ID. NO.3) nucleotide sequence 1201–3850 showing the sequence of ori101.

5. DETAILED DESCRIPTION OF THE INVENTION

Bacterial live vector vaccines employs a bacterial live vector to express genes encoding protective antigens of bacterial, viral or parasitic pathogens. The bacterial protective antigens are preferably non-native to the bacterial live vector, i.e. heterologous. The bacterial live vector vaccine is administered to a host, thereby exposing the expressed antigens to the host's immune system, eliciting an immune response of appropriate character to confer immunity on the host.

In order to achieve enhanced immunogenicity, the plasmids expressing such protective antigens must be stabilized. To the inventor's knowledge, no currently available *S. typhi*-based Plasmid Maintenance System takes advantage of naturally occurring partition mechanisms known to improve the stability of multicopy plasmids.

The present invention provides a non-catalytic Plasmid Maintenance System for the stabilization of expression plasmids encoding foreign antigens in a *S. typhi* live vector vaccine strain. In one aspect the *S. typhi* strain is CVD 908-htrA. In another aspect, the present invention improves and/or optimizes maintenance of expression plasmids by providing Plasmid Maintenance Systems which operate at two independent levels: (1) removing sole dependence on catalytic balanced lethal maintenance systems; and (2) incorporating a plasmid partition system which will remove random segregation of the expression plasmids, thereby enhancing their inheritance and stability.

The non-catalytic Plasmid Maintenance System of the present invention improves the stability of multicopy expression plasmids within a live bacterial vector vaccine, such as CVD908-htrA.

In one aspect, the present invention incorporates the naturally occurring PSK function hok-sok from the antibiotic-resistance factor pR1 within multicopy expression plasmids. The hok-sok system is a silent plasmid addiction system based on antisense RNA control mechanisms that only results in synthesis of lethal proteins after plasmid loss has occurred. A critical reason for pursuing this particular approach is that this method of improving plasmid maintenance involves no additional manipulations of the live vector strain, and therefore can improve the immunogenicity of heterologous antigens expressed within any live vector strain.

The present invention also provides a plasmid maintenance system comprising a complementation-based PSK function in which the chromosomal gene ssb, encoding the essential non-catalytic single-stranded binding protein (SSB) required for DNA replication, is specifically deleted and inserted within a multicopy expression plasmid.

The present invention also provides an improved Plasmid Maintenance System comprising an expression plasmid having inserted therein a SEG locus and PSK function.

5.1 Suicide Vectors

Heterologous antigens can be expressed within live vector strains, such as CVD908-htrA, from genes residing either on plasmids or integrated within the chromosome. One technique for integrating these genes into the host chromosome involves the use of temperature sensitive "suicide vectors" such as pIB307 which contains a temperature-sensitive origin of replication from pSC101 (ori101). The present invention provides an improved suicide vector for use in CVD908 and CVD908-htrA, derived from pIB307 which allows for easier construction of mutagenesis cassettes to alter the live vector chromosome.

Integration of these suicide vectors into the chromosome by homologous recombination results from temperature inactivation of the plasmid replication protein, RepA, a protein essential to the function of ori101. Spontaneous resolution of the resulting unstable merodiploid intermediates is detected by counter-selection for loss of the sacB gene contained on the resolving suicide vector. The sacB gene contained on all excised plasmids encodes the levansucrase enzyme, which is lethal when expressed within the cytoplasm of enteric bacteria, including *S. typhi,* growing in the presence of sucrose. Since resolving merodiploids are selected by incubating in the presence of 10% sucrose, excised plasmids will kill host bacteria unless they cure spontaneously.

This system was successfully used to integrate a kanamycin-resistance cassette into the ΔaroC1019 locus of CVD908. However, the success of these experiments rested on the fact that the gene being mobilized into the chromosome of *S. typhi* encoded a selectable drug-resistance marker. Using these early vectors, replacing the kanamycin-resistance cassette with a non-selectable marker was not successful because, although the incoming marker could be integrated into the chromosome as a merodiploid, resolution of the merodiploid to replace the drug resistance gene was never detected.

The present invention also provides a method for using such suicide vectors to inactivate the ssb locus of attenuated *Salmonella typhi* strains such as CVD908.-htrA.

The present invention allows such suicide vectors to permit efficient mobilization of genes expressing proteins or peptides of interest, such as heterologous antigens, into the chromosome of *S. typhi* CVD908-htrA in two stages. A sacB-aph cassette is first introduced into the ΔaroC1019 locus which was selected for using kanamycin. Generation of this *S. typhi* CVD908-htrAΔaroC1019::sacB-aph strain creates a valuable intermediate strain into which, in theory, any structural gene can be efficiently inserted into the aroC locus by marker-exchange. The sacB gene is used as a counter-selectable marker by passing merodiploids in the presence of 10% sucrose to select for replacement of the sacB-aph cassette with the incoming antigen cassette, since resolution of merodiploids in the presence of sucrose will result in loss of the sacB gene in order to produce viable progeny. This intermediate strain was employed to efficiently integrate the non-toxigenic mutant LT-K63 of the *E. coli* heat-labile enterotoxin, creating CVD908ΔaroC1019::LT-K63.

5.2 Plasmid-Based Expression of Heterologous Antigens

Although chromosomal integration of foreign genes confers stability to such sequences, the genetic manipulations involved can be difficult, and the drop in copy number of the heterologous gene often results in production of insufficient levels of heterologous antigen to ensure an optimal immune response.

In contrast, plasmid stability is a complex phenomenon which depends on multiple factors including (1) copy number of the plasmid; (2) appropriately regulated expression of genes contained within the plasmid; and (3) selective pressure for ensuring the proper segregation and inheritance of the plasmid.

To ensure stability, plasmids must be replicated in a regulated manner to prevent their copy number from rising to lethal levels.

In addition, plasmids must segregate during the division of a growing bacterium to ensure that each daughter cell receives at least one copy of the plasmid. Segregation can be a passive, random event or an active process involving synthesis of novel proteins which aid in plasmid segregation and inheritance. Successful inheritance of randomly segregating plasmids relies on a high enough copy number of randomly distributed plasmids within a dividing bacterium to virtually guarantee inheritance of at least one plasmid by each daughter cell.

The commonly used plasmid cloning vectors, including medium copy number pBR322 derivatives and high copy number pUC plasmids, are inherited by random segregation.

Active segregation involves the synthesis of proteins which are proposed to bind to such plasmids and further coordinate with the membranes of dividing bacteria to ensure that each daughter receives at least one plasmid copy. Plasmids employing such active partitioning systems are typically very low copy number plasmids such as the F sex factor of *E. coli* or antibiotic resistance R-factors such as pR1 and pRK2.

The present invention exploits naturally occurring SEG functions to enhance inheritance of multicopy expression plasmids, which would otherwise be inherited by random segregation, to increase the stability of these plasmids.

The present invention also takes advantage of other naturally occurring genetic systems in which daughter cells which do not successfully inherit an expression plasmid will be killed and removed from the growing population, i.e., PSK functions. The incorporation of more than one category of plasmid stabilization function is referred to herein as a Plasmid Maintenance System. For example, the incorporation of both a SEG function such as a partition locus and a PSK function into a single expression plasmid yields a Plasmid Maintenance System.

It should be noted that a gene conferring resistance to a bactericidal antibiotic, such as the aph gene encoding resistance to kanamycin and neomycin, is also considered a PSK function, as is the asd-based balanced-lethal system.

5.3 Balanced Lethal Systems

One method of ensuring the inheritance of expression plasmids involves the construction of a PSK function referred to as a balanced lethal system for plasmids expressing heterologous antigens. In a plasmid-based balanced lethal system, plasmids replicating in the cytoplasm of the bacterium express a critical protein required by the bacterium to grow and replicate. Loss of such plasmids removes the ability of the bacterium to express the critical protein and results in cell death.

Such a system has been successfully employed in *S. typhimurium* and is based on expression of the asd gene encoding aspartate β-semialdehyde dehydrogenase (Asd). Asd is a critical enzyme involved in the synthesis of L-aspartic-β-semialdehyde, which is a precursor essential for the synthesis of the amino acids L-threonine (and L-isoleucine), L-methionine, and L-lysine, as well as diaminopimelic acid, a key structural component essential to the formation of the cell wall in Gram-negative bacteria. Loss of plasmids encoding such a critical enzyme is lethal for any bacterium incapable of synthesizing Asd from the chromosome, resulting in lysis of the bacterium due to an inability to correctly assemble the peptidoglycan layer of its cell wall.

The asd system for improving the stability of expression plasmids by removing plasmid-cured bacteria from the population (i.e. a PSK function), has been successfully employed in attenuated *S. typhimurium*-based live vector strains for immunization of mice with a variety of procaryotic and eucaryotic antigens including such diverse antigens as detoxified tetanus toxin fragment C and the LT enterotoxin, synthetic hepatitis B viral peptides, and gamete-specific antigens such as the human sperm antigen SP10.

Murine mucosal immunization with these live vector strains has elicited significant immune responses involving serum IgG and secretory IgA responses at mucosal surfaces. The asd system has recently been introduced into attenuated *S. typhi* vaccine strains in an attempt to increase the stability of plasmids expressing synthetic hepatitis B viral peptides.

However, when volunteers were immunized with these live vector strains, no immune response to the foreign antigen was detected. See Tacket et al., *Infection and Immunity*, 65:3381, 1997 (incorporated herein by reference). In fact, to date, few reports have documented an immune response to plasmid-based expression of a foreign antigen from plasmids (stabilized or otherwise) after vaccination of humans with an attenuated *S. typhi* live vector.

Although in some cases failure of live vector strains may have resulted from over-attenuation of the strain itself, the inventor's conclusion is that currently used PSK functions for plasmids suffer from additional limitations, in particular, from segregation imitations and catalytic activity limitations. The present invention provides improved expression plasmids comprising enhanced segregation capabilities by incorporating a partitioning system along with a PSK system.

5.4 Segregation Limitations

One limitation of plasmid maintenance functions such as the asd function (as well as the thyA function) is that they do not enhance the inheritance of resident plasmids, which continue to segregate randomly with or without the presence of the asd function. Therefore, if resident expression plasmids carrying asd genes are inherently unstable, they will be lost, regardless of the requirement of the bacterium for Asd.

The inherent stability of an asd expression plasmid can be defined by growing plasmid-bearing strains in the presence of DAP, which removes the selective pressure that ensures that all viable bacteria contain the expression plasmid. If a given plasmid is inherently unstable, it will be lost from bacteria at a high rate and such plasmidless bacteria will lyse in the absence of growth supplements; the overall result of this effect will be a population of bacteria that grows much slower than wildtype unaltered strains.

The present invention can improve plasmid stability by incorporating a SEG function, such as a partition locus, onto the expression plasmid to enhance the inheritance of such plasmids by actively dividing bacteria. As pointed out above, partition loci are naturally present on the virulence plasmids of *S. typhimurium*. Tinge and Curtiss, *Journal of Bacteriology*, 172:5266, 1990 (incorporated herein by reference) reported that such partition loci were well conserved among *S. typhimurium* virulence plasmids, and that when a 3.9 kb restriction fragment encoding this locus was introduced onto the lower copy number plasmid pACYC184 (~15 copies per cell), the observed plasmid stability increased from 34% plasmid-containing cells to 99% plasmid-bearing cells after 50 generations. The nucleotide sequence of this locus was later determined by Cerin and Hackett, Plasmid, 30:30, 1993 (incorporated herein by reference), (GenBank Accession Number M97752).

5.5 Catalytic Activity Limitations

Another potential limitation of a plasmid maintenance function such as the asd function (as well as the thyA system) is its reliance on an enzyme with catalytic activity. Given that complementation with only a single copy of the asd gene is sufficient to remove auxotrophy, it is not clear why all copies of a multicopy plasmid should remain stable, especially if they encode an especially problematic heterologous antigen which inhibits growth of the bacterium.

Further, although higher copy number expression plasmids may express appreciable levels of a given heterologous antigen in vitro, such plasmids may not be maintained at the expected copy numbers in vivo due to toxicity and may in fact be present at much lower copy numbers, which would be expected to reduce any observed immune response specific for the heterologous antigen. Accordingly, the present invention thus provides stably maintained low and medium copy number plasmids for expressing heterologous antigens.

5.6 The Non-Catalytic ssb PSK Function

The potential limitation of catalytic activity associated with balanced lethal systems is addressed here through the use of plasmids expressing the single-stranded binding protein (SSB) from *S. typhi* to trans-complement an otherwise lethal mutation introduced into the chromosomal ssb gene. The biochemistry and metabolic roles of the *E. coli* SSB protein have been extensively reviewed in Lohman et al., *Annual Reviews in Biochemistry* 63:527, 1994 and Chase et al., *Annual Reviews in Biochemistry* 55:103, 1986 (the disclosures of which are incorporated herein by reference).

SSB is a non-catalytic 177 amino acid protein, with a relative molecular weight of 19 kDa, that binds with high affinity to single-stranded DNA (ssDNA), and plays an essential role as an accessory protein in DNA replication, recombination, and repair. The biologically relevant form of SSB involved in binding to ssDNA is a tetramer, which binds in two modes to ssDNA, intimately associating with an average of either 35 ($SSB_{35}$-binding mode) or 65 bases ($SSB_{65}$-binding mode). The specific conditions controlling the preferred mode of binding are complex and depend on the surrounding concentration of monovalent and divalent salts, pH, and temperature, as well as the amount of SSB protein present. Under given conditions, high concentrations of SSB favor the $SSB_{35}$-binding mode, with lower SSB concentrations favoring the $SSB_{65}$-mode. However, it must be emphasized that in both binding modes, the required conformation of SSB is a tetramer.

Spontaneously occurring temperature-sensitive point mutations within the ssb gene have now been characterized at the biochemical, physiological, and nucleotide level; one such mutant, ssb-1, contains the point mutation His 55 to Tyr, and has been found to be unable to assemble correctly into tetramers at non-permissive temperatures. These mutant strains exhibit temperature-sensitive lethal defects in DNA replication and recombination.

The segregation frequencies of plasmids carrying ssb which complement chromosomal ssb mutations in *E. coli* bacteria were examined by Porter et al. Bio/Technology 8:47, 1990 (incorporated herein by reference). They observed that in experiments involving bioreactors, the segregation frequency in plasmid-bearing strains growing in continuous culture under non-selective conditions for 150 hours was less than $1 \times 10^{-7}$; this segregation frequency was independent of copy number, as both lower copy number pACYC184 plasmids and very high copy number pUC19 plasmids were maintained at the same frequency. However, it must be noted that the plasmids involved expressed only a drug-resistance marker in addition to the SSB protein.

The present invention provides an improved plasmid maintenance system which incorporates a partition locus such as that present on pSC101, and may also incorporate an active partitioning system such as that described above for the virulence plasmid of *S. typhimurium*.

The present invention removes dependence on catalytic enzymes to confer plasmid stability. In one aspect, mutated alleles similar to ssb-1 are introduced into the expression plasmids to enhance higher copy number plasmids by overexpression of SSB1-like proteins to form the required biologically active tetramers of SSB. In another aspect the present invention provides a PSK function involving a silent plasmid addiction system based on antisense RNA control mechanisms that only synthesize lethal proteins after plasmid loss has occurred.

5.7 Expression Plasmids and Self-contained Genetic Cassettes

The present invention also comprises a series of expression plasmids which are referred to herein as pGEN plasmids. pGEN plasmids comprise self-contained genetic cassettes encoding regulated expression of a heterologous antigen, an origin of replication, and a selectable marker for recovering the plasmid. This vector series has been specifically designed to test whether any Plasmid Maintenance System can increase the stability of plasmids, for example within an attenuated *S. typhi* vaccine background.

Figure 1C:
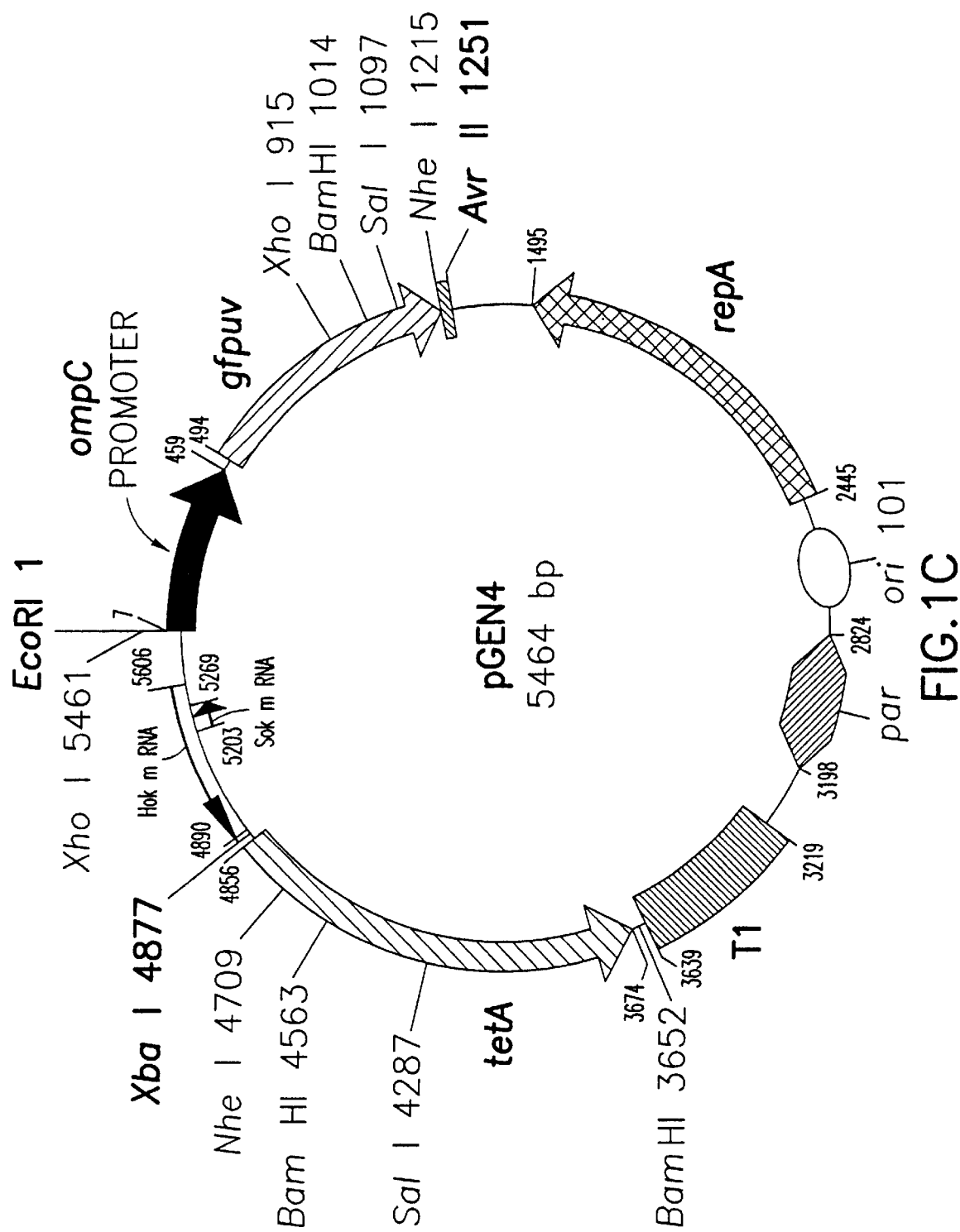

The basic structure of these vectors is represented in FIG. 1, and the composite gene sequences for the vectors pGEN 2 (SEQ. ID. NO.1), pGEN 3 (SEQ. ID. NO.2) and pGEN 4 (SEQ. ID. NO.3) are represented in FIGS. 4, 5 and 6, respectively.

It is critical to note that the pGEN plasmids are designed to be comprised of a set of 3 independently functioning genetic cassettes. These cassettes have been constructed such that individual components can be optimized by replacement as necessary. Accordingly, in addition to the various Plasmid Maintenance Systems described herein, the cassettes can test other promising systems now in existence or which may become available in the future. Further, the optimized plasmid(s) can be adapted to express relevant protective heterologous antigens within attenuated vaccine strains for immunization of humans.

The pGEN plasmids provide a regulated test antigen expression cassette which operates such that as induction of antigen expression is increased, a metabolic burden is placed on the bacterium which leads phenotypically to plasmid instability, i.e. a selective advantage is created for all bacteria which can spontaneously lose the offending plasmid. Thus one aspect of the present invention provides a conditionally unstable plasmid which can be examined for stability as plasmid maintenance functions are incorporated.

In a preferred mode, the regulated test antigen expression cassette contained within the pGEN plasmids comprise the inducible ompC promoter driving expression of a fluorescent protein such as the green fluorescent protein (GFP), overexpression of which is toxic to *E. coli* and *S. typhi*.

The present invention also comprises a series of plasmid replicons having copy numbers which vary from low copy number (i.e. ~5 copies per cell) to medium copy number (~15 copies per cell) to high copy number (~60 copies per cell). To accomplish this, origins of replication from the well-characterized plasmids pSC101, pACYC184, and pAT153 have been modified using polymerase chain reaction (PCR) techniques to create independently functioning plasmid replication cassettes. These replication cassettes permit testing of the efficiency of a plasmid stabilization system as copy number is increased.

The present invention also comprises selectable expression plasmids for use in attenuated *S. typhi* live vectors. These expression plasmids contain a selectable marker which can ultimately be replaced either by a non-drug resistant locus or by a gene encoding an acceptable drug resistance marker such as aph encoding resistance to the aminoglycosides kanamycin and neomycin.

To accomplish this, resistance cassettes encoding resistance to carbenicillin and tetracycline have been constructed, with transcription being efficiently terminated by an rrnB T1T2 terminator. A detailed description of the individual components comprising the expression and replication cassettes follows.

5.8 Components of the Antigen Expression and Replication Cassettes

5.8.1 Promoter

It will be appreciated by one of skill in the art that a wide variety of components known in the art may be included in the expression cassettes of the present invention, including a wide variety of transcription signals, such as promoters and other sequences that regulate the binding of RNA polymerase to the promoter. The operation of promoters is well known in the art and is described in Doi, Regulation of Gene Expression, *Modem Microbial Genetics* pages 15–39 (1991) (the entire disclosure of which is incorporated herein by reference). The ensuing description uses the ompC promoter by way of example, and is not meant to delimit the invention.

The promoter is preferably an environmentally regulatable promotor controlled by a biologically relevant signal such as osmolarity. In a preferred mode, the promoter is the ompC promoter. The ompC gene encodes a porin protein which inserts as a trimer into the outer membrane of a bacterial cell. Expression and control of ompC is complex and has recently been reviewed in considerable detail in Pratt et al., *Molecular Microbiology* 20:911, 1996 and Egger et al., Genes to Cells 2:167, 1997 (the disclosures of which are incorporated herein by reference).

Synthesis of the OmpC protein is ultimately controlled at the level of transcription by the osmolarity of the surrounding environment such that increases in osmolarity are accompanied by increases in the transcription of ompC. However, increases in osmolarity do not directly mediate increases in the transcription of ompC. Rather, the bacterium senses the surrounding osmolarity using a two-component signal transduction system encoded by the ompB operon. This operon is composed of two genes transcribed in the order envZ-ompR. The envZ gene encodes a 450 amino acid (a.a.) protein, containing two transmembrane regions, which inserts into the bacterial inner membrane (perhaps as a dimer) with an N-terminal 118 a.a. osmotic-sensing domain extending into the periplasmic space and a C-terminal 270 a.a. catalytic domain extending into the cytoplasm. The C-terminal catalytic domain possesses both kinase and phosphatase activities which are modulated by osmolarity such that as osmolarity increases, kinase activity predominates, and as osmolarity drops, phosphatase activity predominates.

EnvZ kinase activity phosphorylates aspartic acid residue 55 of the 239 a.a. cytoplasmic protein OmpR, creating OmpR-P. It is the OmpR-P modified protein which binds to the ompC promoter and activates transcription by RNA polymerase; therefore, as osmolarity increases, increasing kinase activity of EnvZ produces higher levels of OmpR-P, which in turn lead to greater transcription of ompC. OmpR-P binds to a region of the ompC promoter spanning bases $-41$ (relative to the transcriptional start site of $+1$) to $-102$, with initial binding of OmpR-P to bases $-78$ through $-102$ being followed by additional binding to bases extending to $-41$ as the concentration of OmpR-P increases with osmolarity. In addition, OmpR-P has been shown to bind to an AT-rich upstream region extending back to base $-405$ which further enhances ompC transcription.

In a preferred embodiment the ompC promoter fragment from *E. coli* spans nucleotides $+70$ through $-389$. The promoter can direct transcription within attenuated *S. typhi* strains of an antibiotic resistance gene, such as the kanamycin resistance gene in an osmotically sensitive manner. For example, our experiments have demonstrated that when the concentration of NaCl in liquid growth medium was increased from 0 mM to 300 mM, resistance to kanamycin increased from 0 $\mu$g/ml to $>800$ $\mu$g/ml.

5.8.2 Origin of Replication

Due to varying degrees of toxicity associated with different heterologous antigens (i.e. higher toxicity for antigens derived from parasitic organisms such *Plasmodium falciparum* vs. virtually no toxicity for the fragment C of tetanus toxin), the present invention provides live vector vaccines which preferably express such antigens from either low or medium copy plasmids. It will be appreciated by one skilled in the art that the selection of an origin of replication will depend on the degree of toxicity, i.e., the copy number should go down as toxicity to the bacterial strain goes up. In a preferred mode, the Plasmid Maintenance System(s) used are capable of stabilizing replicons of low or medium copy numbers.

It is preferable for the origin of replication to confer an average copy number which is between about 2 and about 75. In a preferred mode the origin of replication is selected to confer an average copy number which is between about 5 and about 50. More preferably the range is from about 5 to about 45.

In one aspect, the origin of replication is from pSC101, conferring a copy number of approximately 5 per genome equivalent.

The oriE1 locus specifies synthesis of a 555 base transcript called RNA I and synthesis of a 110 base antisense RNA transcript called RNA II. As RNA I is synthesized, the 5'-proximal region of the transcript adopts a stem-loop structure composed of 3 domains which can hybridize to a complementary stem-loop structure formed by RNA II, resulting in a double stranded RNA-RNA structure forming which causes plasmid replication to abort.

As synthesis of RNA I continues, generating the full-length 555 base transcript, a rearrangement of the secondary structure of the transcript destroys the initial 3 domain stem-loop structure to form an alternate stem-loop configuration which no longer hybridizes to RNA II. Formation of this alternate structure allows the transcript to hybridize to one DNA strand of the plasmid itself, forming an RNA-DNA complex which is nicked by endogenous RNAse H to trigger synthesis of the first DNA strand of the plasmid and plasmid replication.

Plasmid replication is therefore controlled by synthesis of RNA I, which undergoes a cascade of structural configurations leading to initiation of replication. The necessary progression of the RNA I folding cascade (and resulting replication initiation) is interrupted by competition of the domains with RNA II. This mechanism is essentially the same in plasmids containing either oriE1 or ori15A.

The reason these two types of plasmids can coexist within the same bacterium is due to sequence divergence within the region of hybridization between RNA I and RNA II, such that the RNA II from ori15A will not hybridize to RNA I from oriE1; this sequence divergence also affects the stability of the RNA I: RNA II hybrid, accounting for the differences in copy number between plasmids carrying the oriE1 or ori15A origins of replication.

The structural organization of the origins of replication cassettes for pSC101 (ori101; ~5 copies per genome equivalent), pACYC184 (ori15A derivative; ~15 copies per genome equivalent), and pAT153 (oriE1 derivative; ~60 copies per genome equivalent) are analogous in structure and function.

5.8.3 Expressed Protein or Peptide

When the expression cassette is used to screen Plasmid Maintenance Systems, it preferably expresses a protein or peptide with no metabolic activity. A preferred protein is the green flourescent protein (GFP) of the bioluminescent jellyfish Aequorea Victoria, a 238 amino acid protein which undergoes a posttranslational modification in which 3 internal amino acids ($^{65}$Ser-Tyr-Gly$^{67}$) are involved in a cyclization and oxidation reaction. The resulting fluorophore emits blue-green light maximally at a wavelength of 509 nm upon irradiation with long-wave ultraviolet light at a wavelength of 395 nm. In addition, fluorescence activity is remarkably constant over a wide range of pH from 5.5–12 and at temperatures up to 70° C.

Since GFP has no known catalytic activity, the level of observed fluorescence within individual bacteria expressing GFP can provide a direct indication of transcription levels of the gfp gene carried by each bacterium. Expression of the GFP protein has now been quantitated in a variety of both prokaryotic and eukaryotic cells and requires no additional cofactors or enzymes from *A. victoria*. Fluorophore formation is apparently dependent either on ubiquitous enzymes and cofactors, or is an autocatalytic event.

Individual bacteria expressing GFP can be quantitated either alone or within macrophages, epithelial cell lines, and infected animal tissues using flow cytometry. GFP fluorescence is absolutely dependent on residues 2–232 of the undenatured protein. However, fusion of unrelated biologically active protein domains to the N-terminus of GFP has still resulted in fusion proteins with the expected heterologous biological activity which continue to fluoresce as well.

It has been confirmed by sequence analysis (Clontech) that the gfp allele preferred here (i.e. gfpuv) expresses a GFP mutant containing 3 amino acid substitutions (not involving the fluorophore) which increase fluorescence 18-fold over that of wildtype GFP.

In addition, 5 rarely used arginine codons have been optimized for efficient expression of GFP in *E. coli*. Since comparison of expression levels of various heterologous proteins in *E. coli* and CVD908 has demonstrated equivalent or superior expression within CVD908, it is expected that gfpuv will function efficiently in CVD908-htrA.

A coding sequence is inserted in a correct relationship to a promoter where the promoter and the coding sequence are so related that the promoter drives expression of the coding sequence, so that the encoded peptide or protein is ultimately produced. It will be understood that the coding sequence must also be in correct relationship with any other regulatory sequences which may be present.

5.8.4 Heterologous Antigens

The expression plasmids of the present invention preferably express an antigen for presentation to a host to elicit an immune response resulting in immunization and protection from disease. While Shiga toxins are presented herein as examples of antigens usefully expressed by the vaccine expression plasmids disclosed herein, the invention is broad in scope and encompasses the expression of any antigen which does not destroy the bacterial live vector and which elicits an immune response when the bacterial live vector containing said expression plasmid(s) is administered to a host, i.e., a human or other animal.

The vaccine expression plasmids provided herein are used to transform attenuated bacterial strains, preferably strains used for human vaccination and most preferably used to transform CVD908-htrA, and preferably encode either the B subunit of Stx2 or a genetically detoxified Stx2 holotoxin.

A sub-set of STEC most often referred to as enterohemorrhagic *E. coli* (EHEC) are capable of causing severe clinical syndromes including hemorrhagic colitis, hemolytic uremic syndrome (HUS) and thrombotic thrombocytopenic purpura (TTP) in a small proportion of infected individuals, in addition to causing non-bloody diarrhea in most others.

Hemorrhagic colitis is characterized by copious bloody diarrhea, usually without fever or with only low-grade fever and a relative paucity of fecal leukocytes demonstrable in the diarrheal stools. These features differentiate hemorrhagic colitis from dysentery caused by Shigella which is typically scanty stools of blood and mucus, preceded by high fever and with large numbers of fecal leukocytes visible by microscopy.

HUS, a potentially fatal disease that most often affects young children but may afflict individuals of any age, is characterized by the triad of microangiopathic hemolytic anemia, thrombocytopenia and uremia. Currently in North America, HUS is the most frequent cause of acute renal failure in infants and young children. In a study by Siegler et. al. of 288 patients treated for postdiarrheal HUS in Utah from 1970–1994, severe disease (defined as anuria lasting longer than 7 days, oliguria lasting for longer than 14 days, or extrarenal structural damage such as stroke) occurred in 25% of cases and was associated with children less than two years of age; about one third of these severe cases of HUS resulted in death (5%) or severe sequelae including end-stage renal disease (5%) or chronic brain damage (3–5%), with less severe chronic problems involving hypertension, proteinuria, or azotemia.

TTP, which most often affects adults, is characterized by neurologic complications such as stroke, in addition to thrombocytopenia, hemolytic anemia and renal disease.

By far the most common EHEC serotype is O157:H7. Nevertheless, other EHEC serotypes also cause HUS and hemorrhagic colitis, including O26:H11, O111 :H8 and a number of others. EHEC strains associated with HUS always elaborate one or more Shiga toxins and carry a 60 MDa virulence plasmid. In addition, most also harbor a chromosomal pathogenicity island (so-called LEE) having a set of genes that encode the ability to attach and efface. It is well accepted that Shiga toxins elaborated by EHEC play a key role in the pathogenesis of hemorrhagic colitis and HUS.

As described in detail below, the Shiga toxin family is comprised of two groups of toxins, Stx1 (which is essentially identical to cytotoxin/neurotoxin/enterotoxin produced by Shigella dysenteriae type 1, the Shiga bacillus) and Stx2 (which is immunologically distinct from Stx1 and has several related variants). In the USA, the overwhelming majority of EHEC associated with cases of HUS express Stx2, either alone or in conjunction with Stx1.

The most important reservoir of EHEC infection are bovines. The single most important mode of transmission of EHEC to humans is via the consumption of under-cooked contaminated beef, most often ground beef. Less commonly, a variety of other food vehicles and other modes of transmission have been incriminated. Most notably, EHEC are one of the handful of bacterial enteric pathogens, which, like Shigella, can be transmitted by direct contact or by contact with contaminated fomites.

There is great anticipation and optimism on the part of most epidemiologists that irradiation of meat sold in the USA will drastically curtail the transmission of EHEC to humans, since it will curtail the single most important mode of transmission. Nevertheless, certain risk groups exposed to other modes of transmission of EHEC will not benefit from this intervention. For example, the exposure of abattoir workers to EHEC, an occupational hazard, occurs at a point in the meat processing cycle prior to when irradiation would be utilized. For such special groups such as these for whom risk will remain even after irradiation of meat becomes commonplace, anti-EHEC vaccines can be useful. The present invention provides vaccines against EHEC useful for the prevention of infection (in the animal reservoirs or in humans) and for preventing the severe complications of EHEC infection by stimulating neutralizing Shiga antitoxin.

Studies with attenuated Vibrio cholerae O1 expressing Stx1 B subunit have demonstrated the feasibility of eliciting neutralizing Shiga antitoxin by mucosal immunization with live vectors. However, since virtually all EHEC associated with HUS cases in the USA express Stx2, alone or in conjunction with Stx1, it is preferable that a vaccine for preventing the severe complications of EHEC infection via elicitation of toxin-neutralizing antibodies should stimulate anti-Stx2 as well as Stx1. It is within the broad scope of the present invention to provide a stabilized plasmid system for expressing Stx2 antigens, alone or in conjunction with Stx1, in attenuated *S. typhi* live vector.

Other antigens which may be suitably delivered according to the compositions and methods of the present invention include, for example, those for hepatitis B, Haemophilus influenzae type b, hepatitis A, acellular pertussis ($_{ac}$P), varicella, rotavirus, *Streptococcus pneumoniae* (pneumococcal), and *Neisseria meningitidis* (meningococcal). See Ellis et al., Advances in Pharm., 39: 393–423, 1997 (incorporated herein by reference).

In one aspect, the antigens encoded by the expression plasmids of the present invention are cancer vaccines.

In another aspect, the antigens encoded by these plasmids are designed to provoke an immune response to autoantigens, B cell receptors and/or T cell receptors which are implicated in autoimmune or immunological diseases. For example, where inappropriate immune responses are raised against body tissues or environmental antigens, the vaccines of the present invention may immunize against the autoantigens, B cell receptors and/or T cell receptors to modulate the responses and ameliorate the diseases. For example, such techniques can be efficacious in treating myasthenia gravis, lupus erythematosis, rheumatoid arthritis, multiple sclerosis, allergies and asthma.

5.8.4.1 The Shiga Toxin Family

Conradi in 1903 first reported that *S. dysenteriae* 1 produced a powerful exotoxin. Because injection of this toxin led to hind limb paralysis of rabbits it was originally called a neurotoxin. Subsequently this toxin, Shiga toxin, was shown to be lethal for certain cells in tissue culture (i.e., it was a cytotoxin). Vicari et al. and then Keusch et al. demonstrated that it also functioned as an enterotoxin.

Scientists now recognize the existence of a family of Shiga cytotoxins which inhibit protein synthesis, leading to cell death for susceptible cells. For many years after the revelation that such toxins were produced by certain *E. coli* strains in addition to the original Shiga toxin produced by *Shigella dysenteriae* type 1, the nomenclature for this family of toxins was confusing. Since early reports described the activity of these toxins on Vero cells (a cell line derived from African green monkey kidney epithelial cells), many investigators called them verotoxins. Others referred to these toxins expressed in *E.coli* as Shiga-like toxins.

The protein toxins are collectively referred to herein as Shiga toxins (Stx), and the genes encoding these toxins are designated as stx with subscripts denoting the group and variant [i.e. $stx_1$ for the Shiga toxin produced by *E. coli* that is essentially identical to that of *Shigella dysenteriae* type 1 (stx), and $stx_2$, $stx_{2c}$, $stx_{2d}$, $stx_{2e}$ for the antigenically distinct group of related toxins].

The structure, biochemistry and antigenicity of Shiga toxins are well described in Melton-Celsa et al., *Eschericia coli* 0157:H7 and *Other Shiga Toxin-producing E. coli Strains*, 1998; Takeda, *Bacterial Toxins and Virulence Factors in Disease*, 1995; Gyles, *Canadian J. of Microbiology*, 38:734, 1992; and O'Brien et al., *Current Topics in Microbiology and Immunology*, 180:165, 1992 (the disclosures of which are incorporated herein by reference).

These Shiga cytotoxins are composed of a single catalytic A subunit of approximately 32 kDa non-covalently associated with a pentameric receptor binding domain of approximately 7.7 kDa B subunits. These subunits are encoded by a single operon of the order stxA-stxB; transcription of the stx and $stx_1$ operons are iron-regulated in both *S. dysenteriae* type 1 and *E. coli*, but no environmental control signals have as yet been determined for any $stx_2$ operon. None of these toxins is encoded on a plasmid; rather they are phage-encoded (Stx1, Stx2, Stx2c, and Stx2d) or are chromosomally encoded (Stx, Stx2e).

As mentioned above, all members of the Shiga toxin family are cytolytic toxins which inhibit protein synthesis within susceptible cells by blocking the binding of elongation factor 1-dependent aminoacyl-tRNA to ribosomes. For all toxins identified from human infections, penetration of susceptible cells by endocytosis follows binding of the holotoxin to the necessary cell surface glycolipid receptor globotriaosyl ceramide ($Gb_3$), trafficking of the toxin to the Golgi apparatus and endoplasmic reticulum, followed by release into the cytoplasm. Shiga toxins are RNA N-glycosidases which depurinate a single adenine from the 28S RNA of the eucaryotic 60S ribosomal subunit, thus inactivating the 60S subunit and eventually leading to cell death.

There are six prototypic members of the Shiga toxin family: Stx, Stx1, Stx2, Stx2c, Stx2d, and Stx2e, which differ from one another immunologically and in toxic activity. Significant detail has been included here to provide background for understanding the significance of point mutations discussed below, which are required for the genetically detoxified holotoxins. The members of the Shiga toxin family differ from one another in 3 fundamental ways, as recently summarized by Melton-Celsa et al., *Eschericia coli* 0157:H7 and *Other Shiga toxin-producing E. coli strains*, 1998:

(1) Immunologically: The Shiga toxin family is composed of two serogroups, Stx/Stx1 and Stx2; antisera raised against Stx/Stx1 do not neutralize members of the Stx2 serogroup, as judged by the Vero cell cytotoxicity assay.

(2) Structurally: Stx and Stx1 are essentially identical, differing in a single amino acid at position 45 of the mature A subunit, and the crystal structure for the Stx holotoxin has been solved. The prototype Stx2 is only 55% homologous to residues of the mature A subunit of Stx/Stx1 and 57% homologous to the mature B subunit, which explains why antisera raised against Stx/Stx1 do not neutralize members of the Stx2 group. Within the Stx2 group, Stx2e is most distantly related, sharing 93% amino acid homology to the mature A subunit of Stx2 and 84% homology to the mature B subunit; Stx2c and Stx2d are very similar to Stx2, sharing 99–100% homology in mature A subunit residues and 97% homology in mature B subunit residues.

(3) Cytotoxicity: Stx2 is among the most lethal of the Shiga toxins, with an $LD_{50}$ for mice injected intraperitoneally of 0.5–2 ng. The $LD_{50}$ for Stx1 and Stx2e is 200–400 ng, and 1–5 ng for Stx2d; however, Stx2d is unusual in that this toxin can become activated by murine intestinal mucus to increase the toxicity of the toxin, lowering the $LD_{50}$ to 0.5 ng.

5.8.5 Site-Specific Mutagensis of Shiga Toxins

In one aspect, the invention provides a genetically detoxified Shiga toxin. The detoxification is accomplished by site-specific mutagenesis, introducing two defined and well-separated point mutations altering critical residues within the catalytic site of the A subunit. The invention also introduces two additional defined and well-separated point mutations within the B subunit to alter critical residues within the primary binding site (i.e. SITE I) residing within the cleft formed by adjacent B subunits of the holotoxin pentameric ring.

Prior attempts have been made to alter the lower affinity binding SITE II. However, this binding site has only been identified from molecular modeling studies, and is not extensively supported by mutational studies which favor SITE I binding of the $Gb_3$ receptor. Even if SITE II is an alternate low-affinity binding site allowing entry of our mutant holotoxin into susceptible cells, the inactivation of the catalytic domain will still prevent cell death.

Based on amino acid sequence alignments, X-ray crystallography studies, and molecular modeling studies, essential amino acids have been identified comprising the active site within the catalytic A subunit of Stx, as well as those residues comprising the binding SITE I within the B subunit pentamer of Stx/Stx1. It is the inventor's conclusion that the amino acids essential to the active site are selected from the group consisting of Tyr 77, Tyr 114, Glu 167, Arg 170, and Trp 203. The residues believed to be required for receptor binding to the clefts formed by adjacent B subunits include Lys 13, Asp 16, Asp 17, Asp 18, Thr 21, Phe 30, Glu 28, Gly 60, and Glu. These site predictions are now being supported by functional studies and in vivo experiments using defined single and double mutations, within individual domains of the holotoxin, introduced by site-specific mutagenesis. A summary of promising mutations is presented in Table 1. Based on these data and crystallographic predictions, it is within the broad practice of the invention to provide expression plasmids encoding, Shiga toxins having two specific sets of point mutations within both the A and B subunits to create non-toxic mutant Stx2 holotoxins for use as vaccines, such as by expression within CVD908-htrA.

TABLE 1

SITE-SPECIFIC MUTAGENESIS STUDIES

| SUBUNIT | TOXIN | MUTATION | DROP IN CYTOTOXICITY | DROP IN LETHALITY | NEUTRALIZING ANTIBODIES |
|---|---|---|---|---|---|
| A | Stx1 | Leu201 → Val + Δ of residues 202–213 | NO cytotoxicity | — | — |
|  | Stx1 | Glu167 → Asp | $10^3$ | — | — |
|  | Stx1 | Arg170 → Leu | $10^3$ | — | — |
|  | Stx2 | Glu167 → Asp | $10^3$ | — | — |
|  | Stx2e | Glu167 → Asp | $10^4$ | — | — |
|  | Stx2e | Arg170 → Lys | 10 | — | — |
|  | Stx2e | Glu167 → Asp Arg170 → Lys | $10^4$ | — | — |
|  | Stx2e | Glu167 → Gln | $10^6$ | $10^4$ | Y |
| B | Stx | Asp16 → His + Asp17 → His | NO cytotoxicity | — | — |
|  | Stx | Arg33 → Cys | $10^8$ | — | — |
|  | Stx | Gly60 → Asp | $10^6$ | — | — |
|  | Stx1 | Phe30 → Ala | $10^5$ | 10 | Y |
|  | Stx2 | Ala42 → Thr | $10^3$–$10^4$ | Y | Y |
|  | Stx2 | Gly59 → Asp | $10^3$–$10^4$ | Y | Y |

5.9 Pharmaceutical Formulations

It is contemplated that the bacterial live vector vaccines of the present invention will be administered in pharmaceutical formulations for use in vaccination of individuals, preferably humans. Such pharmaceutical formulations may include pharmaceutically effective carriers, and optionally, may include other therapeutic ingredients, such as various adjuvants known in the art.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the compounds which are desirable and efficacious for the vaccination application. The bacterial live vector materials are delivered in an amount capable of eliciting an immune reaction in which it is effective to increase the patient's immune response to the expressed mutant holotoxin or to other desired heterologous antigen(s). An immunizationally effective amount is an amount which confers an increased ability to prevent, delay or reduce the severity of the onset of a disease, as compared to such abilities in the absence of such immunization. It will be readily apparent to one of skill in the art that this amount will vary based on factors such as the weight and health of the recipient, the type of protein or peptide being expressed, the type of infecting organism being combatted, and the mode of administration of the compositions.

The modes of administration may comprise the use of any suitable means and/or methods for delivering the bacterial live vector vaccines to a corporeal locus of the host animal where the bacterial live vector vaccines are immumostimulatively effective.

Delivery modes may include, without limitation, parenteral administration methods, such as subcutaneous (SC) injection, intravenous (IV) injection, transdermal, intramuscular (IM), intradermal (ID), intraperitoneal (IP), as well as non-parenteral, e.g., oral, nasal, intravaginal, pulmonary, opthalmic and/or rectal administration.

The dose rate and suitable dosage forms for the bacterial live vector vaccine compositions of the present invention may be readily determined by those of ordinary skill in the art without undue experimentation, by use of conventional antibody titer determination techniques and conventional bioefficacy/biocompatibility protocols. Among other things, the dose rate and suitable dosage forms depend on the particular antigen employed, the desired therapeutic effect, and the desired time span of bioactivity.

The bacterial live vector vaccines of the present invention may be usefully administered to the host animal with any other suitable pharmacologically or physiologically active agents, e.g., antigenic and/or other biologically active substances.

Formulations of the present invention can be presented, for example, as discrete units such as capsules, cachets, tablets or lozenges, each containing a predetermined amount of the vector delivery structure; or as a suspension.

6. EXAMPLES

An expression plasmid composed of individual cassettes has been constructed for use in bacterial live vector vaccines such as *E. coli* and Salmonella. With the exception of ribosomal binding sites (RBS), the key genetic loci controlling transcription initiation and termination, plasmid replication, or encoding expressed proteins are contained within defined restriction fragments, as depicted by the representative plasmid diagram of pGEN2 (SEQ. ID. NO.1) seen in FIG. 1. The basic structure of these expression plasmids will first be highlighted and then the data demonstrating the function of each locus within the attenuated vaccine strain CVD908-htrA will be summarized.

6.1 pGEN Structure

Transcription of any heterologous antigen to be expressed within CVD908-htrA is primarily controlled by an inducible promoter contained on an EcoRI-BglII cassette. Since our expression plasmids were initially modeled after pTETnir15, early versions carried the anaerobically-activated nir15 promoter ($P_{nir15}$). However, this promoter has been replaced with a more tightly regulated osmotically controlled promoter $P_{ompC}$ which is easily manipulated in vitro by varying the concentration of NaCl.

Heterologous antigens are contained on a BglII-AvrII cassette, flanked by an optimized RBS at the 5'-proximal end and a trpA transcriptional terminator at the 3'-distal end of this cassette. The origin of replication for these expression plasmids has been designed as an AvrII-BglII cassette, and is protected from read-through transcription originating in flanking regions. These cassettes carry an extremely efficient T1T2 transcriptional terminator at one terminus with the trpA transcriptional terminator from the heterologous antigen cassette at the opposite end of the replication cassette.

The flanking BglII and SpeI sites between the replication cassette and the selection cassette are intended for insertion of a plasmid maintenance function, such as the par locus from pSC101. The selection cassettes contained within the plasmids are contained within SpeI-XbaI cassettes, and can, for example, be used to encode resistance to carbenicillin (the bla gene) or resistance to tetracycline (the tetA gene).

The drug resistance cassette can be replaced with the ssb gene encoding the essential single stranded binding protein of *Salmonella typhi* CVD908-htrA.

The flanking XbaI and EcoRI sites between the selection cassette and $P_{ompC}$ are intended for insertion of a PSK locus such as hok-sok.

6.2 $P_{ompC}$.

An inducible promoter has been constructed to control expression of a heterologous antigen for introduction to the human immune system using the ompC promoter ($P_{ompC}$) from *E. coli*. The basic sequence of the ompC promoter is described in Norioka et al., *Journal of Biologoical Chemistry*, 261:17113, 1986 (the disclosure of which is incorporated herein by reference). Synthesis was carried out using synthetic primers designed to introduce a 5'-proximal EcoRI restriction site and 3'- distal BglII site flanking a fragment of 465 base pairs in which the natural RBS has been removed.

To confirm that this promoter is osmotically controlled within CVD908-htrA, a pBR322-derived plasmid was constructed in which tetA was replaced by a cassette comprised of $P_{ompC}$ driving expression of a promoterless aph cassette derived from the sacB-neo genes of the suicide vectors described above) which confers resistance to kanamycin. This plasmid designated pKompC was introduced into CVD908-htrA by electroporation, and recipients were screened for resistance to kanamycin on LB medium. The osmotically regulated expression of aph was determined by growing CVD908-htrA(pKompC) in LB broth supplemented with 0.0001% (w/v) 2,3-dihydroxybenzoic acid (DHB) and 50 μg/ml of kanamycin for approximately 2 hrs to provide a seed culture; 50 μl of this culture were inoculated into 50 ml Nutrient Broth (NB) supplemented with DHB as above, but with increasing concentrations of kanamycin; a parallel set of cultures were set up with the identical ranges of kanamycin added, but also containing 10% sucrose to hopefully induce $P_{ompC}$. Cultures were incubated overnight at 37° C., and the $O.D._{600}$ was measured. Results are reported in the Table 2 below for Experiment 1.

TABLE 2

| | Experiment 1 | |
| --- | --- | --- |
| CONCENTRATION of KANAMYCIN (μg/ml) | CONTROL ($O.D._{600}$) | 10% SUCROSE ($O.D._{600}$) |
| 0 | 0.91 | 0.34 |
| 50 | 0.13 | 0.35 |
| 100 | 0.07 | 0.31 |
| 300 | 0.02 | 0.19 |
| | Experiment 2 | |
| CONCEN-TRATION of KANAMYCIN (μg/ml) | CONTROL ($O.D._{600}$) | 300 mM NaCl ($O.D._{600}$) |
| 0 | 0.95 | 1.04 |
| 200 | 0.04 | 0.99 |
| 400 | 0.01 | 0.96 |
| 800 | 0.01 | 0.92 |

Although 10% sucrose has an inhibitory effect on the growth of CVD908-htrA(pKompC), regardless of selective pressure using kanamycin, it is concluded that *E. coli* $P_{ompC}$ is indeed inducible when driving aph gene expression within CVD908-htrA(pKompC).

To confirm this, a culture of CVD908-htrA(pKompC) in supplemented LB broth and kanamycin was incubated for 16 hr at 37° C., diluted 1:10 into fresh medium, and incubated at 37° C. for two hrs to provide a seed culture of exponentially growing bacteria. 100 μl aliquots of this culture were then inoculated into 50 ml NB broth cultures (1:500 dilution) containing increasing concentrations of kanamycin from 200 to 800 μg/ml; a parallel set of cultures were set up containing 300 mM NaCl, and all cultures were incubated at 37° C. for 16 hr. Results are reported in Table 2 above for Experiment 2.

It is clear from these experiments that $P_{ompC}$-driven expression of the aph gene within CVD908-htrA confers resistance to kanamycin at levels up to 800 μg/ml in an osmotically regulated manner.

6.3 Modified ompC Promoter

As described above, early versions of the expression plasmid carried $P_{ompC}$ driving transcription of the aph gene. This cassette was later replaced with a 756 bp BglII-NheI cassette containing the gfpuv allele from pGFPuv (Clontech) and the desired construct was recovered in *E. coli*. During the visual screening of *E. coli* colonies sub-illuminated with ultraviolet light, one very brightly fluorescing colony and another representative fluorescent colony were chosen for further study, designated clone 1 and clone 2 respectively. Upon purification of the plasmids involved, it was determined that clone 1 contained a plasmid that no longer carried a BglII site separating $P_{ompC}$ from gfpuv, while clone 2 carried the expected BglII site.

The induction of GFP expression when clones 1 and 2 are grown on nutrient agar in the presence or absence of NaCl was examined, and it was determined by visual inspection that clone 2 displays very little fluorescence when grown on nutrient agar containing no NaCl but fluoresces brightly when plated on nutrient agar containing 300 mM NaCl; clone 1, however, has a higher background level of fluorescence when uninduced and fluoresces intensely when induced with 300mM NaCl.

To rule out mutations within the gfpuv gene which might affect fluorescence, $P_{ompC}$ from clone 1 was replaced with $P_{ompC}$ from clone 2, and the expected decrease in fluorescence as judged by sub-illumination was confirmed. It was therefore concluded that differences in observed fluorescence were controlled by two genetically distinct versions of our $P_{ompC}$ promoter, which will now be designated as $P_{ompC}$ (higher transcription levels with less osmotic control) and $P_{ompC}$ (moderate transcription levels with osmotic control similar to that observed for the $P_{ompC}$-aph cassette described above). The plasmids containing these expression cassettes are designated as pGFPompC1 and pGFPompC2, respectively.

Flow cytometry was also used to characterize differences in induced and uninduced expression of gfpuv, controlled by $P_{ompC}$ and $P_{ompC}$. To accomplish this, isolated colonies of CVD908-htrA, CVD908-htrA(pGFPompC1) and CVD908-htrA(pGFPompC2) grown on nutrient agar containing DHB and 100 μg/ml of carbenicillin were inoculated into 40 ml broth cultures of the same medium, and grown at 37° C./250 rpm for 24 hr to generate seed cultures. Each culture was then diluted 1:100 into either supplemented nutrient broth, supplemented nutrient broth plus 10% sucrose, or supplemented nutrient broth plus 300 mM NaCl, and grown at 37° C./250 rpm for 48 hr; bacteria were then pelleted and resuspended in 1 ml of phosphate-buffered saline (PBS, pH=7.4). Suspensions were then diluted 1:100 in PBS, pH=7.4 and analyzed by flow cytometry using a Coulter Epics Elite ESP with the argon laser exciting bacteria at 488 nm and emissions detected at 525 nm. Results are presented in Table 3 below.

TABLE 3

| Strain | Low Osmolarity | | 10% Sucrose | | 300 mM NaCl | |
| --- | --- | --- | --- | --- | --- | --- |
| | $O.D._{600}$ | Mean Fluorescence | $O.D._{600}$ | Mean Fluorescence | $O.D._{600}$ | Mean Fluorescence |
| CVD908-htrA | 0.34 | 0.3 | 0.27 | 0.3 | 0.41 | 0.3 |
| CVD908-htrA (pGFPompC1) | 0.36 | 18.8 | 0.25 | 38.0 | 0.38 | 39.4 |
| CVD908-htrA (pGFPompC2) | 0.32 | 14.3 | 0.23 | 40.6 | 0.35 | 37.5 |

These data clearly show that when driving expression of gfpuv within the live vector strain CVD908-htrA, $P_{ompC}$ and $P_{ompC}$ are inducible with increasing osmolarity, although the basal level of transcription is still significant in both cases. The results observed under conditions of low osmolarity further support our observations using solid media that $P_{ompC1}$ drives higher heterologous antigen expression than $P_{ompC}$.

6.4 Origins of Replication and Selection Cassettes

The success of expressing potentially toxic or otherwise problematic heterologous antigens within CVD908-htrA depends on the copy number of the expression plasmid. In addition, observed immune responses to a given heterologous antigen are affected by the copy number of the gene(s) encoding the antigen, with chromosomally expressed antigens eliciting poorer immune responses when compared to plasmid-based expression.

An optimized immune response will depend on multicopy plasmid-based expression of the heterologous antigen(s) from plasmids with the appropriate copy number.

Since the appropriate copy number for a given heterologous gene cannot be known a priori, the present invention provides a set of expression plasmids which contain the origins of replication oriE1 (amplified from pAT153; copy number ~60), ori15A (amplified from pACYC184; copy number ~15), and ori101 (amplified from pSC101; copy number ~5). These self-contained replication cassettes are all carried on BglII-BamHI fragments, and are depicted for a set of 3 tetracycline-resistance expression plasmids shown in FIG. 1.

Expression of the $P_{ompC1}$-controlled gfpuv expression cassette contained on these expression plasmids was analyzed using flow cytometry. These experiments were designed to detect whether differences in the level of observed fluorescence could be correlated with the expected copy number of a given, exression plasmid. CVD908-htrA strains carrying pGEN2 (SEQ. I.D. NO.1), pGEN3 (SEQ. I.D. NO.2), and pGEN4 (SEQ. I.D. NO.3), were streaked onto the rich medium SuperAgar supplemented with DHB and 20 μg/ml tetracycline where appropriate. SuperAgar was used because it is a very rich medium (3× LB agar). Plates were incubated at 30° C. to reduce the toxicity of GFP synthesis and allow bacteria to grow luxuriously on the plates. Isolated colonies were then inoculated into 45 ml of SuperBroth supplemented with DHB and 20 μg/ml tetracycline where appropriate, and incubated at 37° C. for 16 hr. Bacteria were concentrated by centrifugation and resuspended in 1 ml of sterile PBS, pH=7.4, and diluted 1:100 in PBS, pH=7.4 prior to FACS analysis. Bacteria were analyzed by flow cytometry, as described above, for two independent growth experiments, and results are displayed in Table 4 at the end of this section.

These data support the conclusion that overexpression of GFP within CVD908-htrA is toxic to the bacteria. As the theoretical copy number increases for the plasmids pGEN4 (SEQ. I.D. NO.3), pGEN3 (SEQ. I.D. NO.2), and pGEN2 (SEQ. I.D. NO.1) expressing GFP under identical growth conditions from the identical $P_{ompC}1$ promoter, the percentage of the growing population which fluoresces declines. It is expected that the "dim" bacteria are not viable bacteria and may no longer contain the expression plasmid, since these cultures were grown in the presence of 20 μg/ml tetracycline. It is noted, however, that when streaked onto solid medium and grown at 37° C. for 24–36 hr, CVD908-htrA(pGEN2 (SEQ. I.D. NO.1)) grows poorly and fails to produce isolated colonies, while CVD908-htrA(pGEN3 (SEQ. I.D. NO.2)) and CVD908-htrA(pGEN4 (SEQ. I.D. NO.2)) grow quite well and produce intensely fluorescing isolated colonies.

GFP is employed herein as representative of other problematic heterologous antigens which would be of interest to include in a bacterial live vector, such as the S. typhi-based live vector; however, it will be appreciated that GFP can be replaced by any non-metabolic protein or peptide antigen.

The data above show that although use of medium-copy expression plasmids containing oriE1 replicons can be of use in expression of some antigens, expression of antigens of higher toxicity will be more successfully expressed from lower copy number plasmids which employ origins of replication yielding average copy numbers between 2 and 30, such as ori15A or ori101 origins of replication.

TABLE 4

| Strain | Percent Dim Bacteria | Mean Fluorescence Of Dim Bacteria (Relative Units) | Percent Fluorescing Bacteria | Mean Fluorescence (Relative Units) |
|---|---|---|---|---|
| Experiment 1 | | | | |
| CVD908-htrA | 100 | 0.6 | 0 | 0 |
| CV0908-htrA(pGEN2) | 19.9 | 0.1 | 80.1 | 38.5 |
| CVD908-htrA(pGEN3) | 17.1 | 0.1 | 82.9 | 28.1 |
| CVD908-htrA(pGEN4) | 12.1 | 0.1 | 88.0 | 22.4 |
| EXPERIMENT 2 | | | | |
| CVD908-htrA | 100 | 0.3 | 0 | 0 |
| CVD908-htrA(pGEN2) | 37.2 | 0.3 | 62.8 | 10.1 |
| CVD908-htrA(pGEN3) | 4.9 | 0.2 | 95.1 | 8.28 |
| CVD908-htrA(pGEN43) | 9.4 | 0.3 | 90.6 | 4.25 |

6.5 The hok-sok Antisense Post-segregational Killing Locus

Using the polymerase chain reaction, the hok-sok PSK genes were amplified using the multiple antibiotic resistance R-plasmid pR1 as the template in these reactions. All initial attempts to clone this locus onto either high or medium copy number plasmids were unsuccessful. In order to directly select for the hok-sok locus during subcloning, a set of primers was designed for use in overlapping PCR reactions such that the final product was a fragment containing a genetic fusion of the hok-sok locus from pR1 and a promoterless tetA gene from pBR322 encoding resistance to tetracycline. This cassette was engineered such that transcription of the hok gene would continue into tetA; the two loci within this cassette were separated by an XbaI restriction site for future manipulations.

Construction of this cassette not only allowed for direct selection of the hok-sok locus, but also allowed for confirmation that the PSK function would operate in S. typhi CVD908-htrA. After electroporation of plasmids carrying the cassette into CVD908-htrA, transformants could be selected using tetracycline. Successful recovery of isolated colonies indicates successful synthesis of the hok-tetA mRNA, and successful synthesis of the antisense sok RNA to prevent translation and synthesis of Hok, which would kill the bacteria. Recovery of the hok-sok-tetA cassette then became straightforward, and was easily incorporated into our expression plasmids to create the selectable marker cassette of the plasmids pGEN2 (SEQ. I.D. NO.1), pGEN3 (SEQ. I.D. NO.2), and pGEN4 (SEQ. I.D. NO.3) depicted in FIG. 1.

Experiments were then initiated to determine the effect of the hok-sok PSK function on the stability of expression plasmids containing oriE1 and the resistance marker bla encoding β-lactamase which confers resistance to carbenicillin. The hok-sok cassette was inserted into the pAT153-based expression plasmid pTETnir15, in which the Pnir15-toxC heterologous antigen cassette was replaced with our $P_{ompC1}$-gfpuv cassette, creating the plasmids pJN72 (without hok-sok) and pJN51 (with hok-sok). An additional set of plasmids was created by replacing $P_{ompC1}$ with the weaker promoter $P_{ompC2}$, creating pJN10 and pJN12; the structures of these four isogenic plasmids are represented in FIG. 2. CVD908-htrA strains carrying either pJN72, pJN51, pJN10, or pJN12 were streaked onto the rich medium SuperAgar supplemented with DHB and 100 μg/ml carbenicillin, and plates were incubated as above for the pGEN plasmids at 30° C. to reduce the toxicity of GFP synthesis and allow bacteria to grow luxuriously on the plates.

Figure 3E:
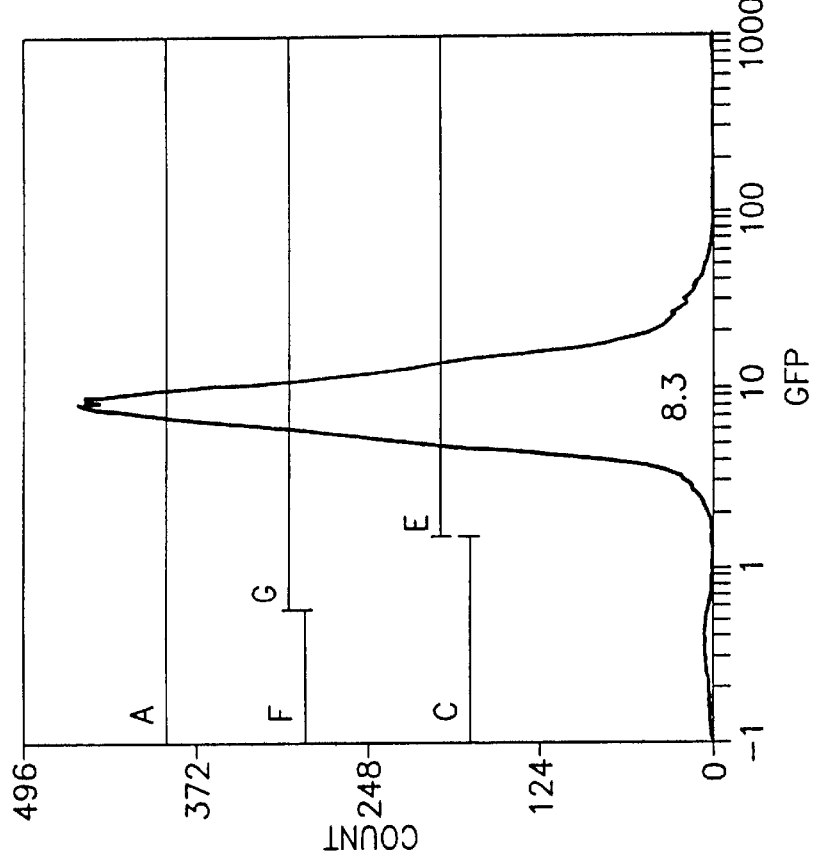
Figures 3G, 3H:
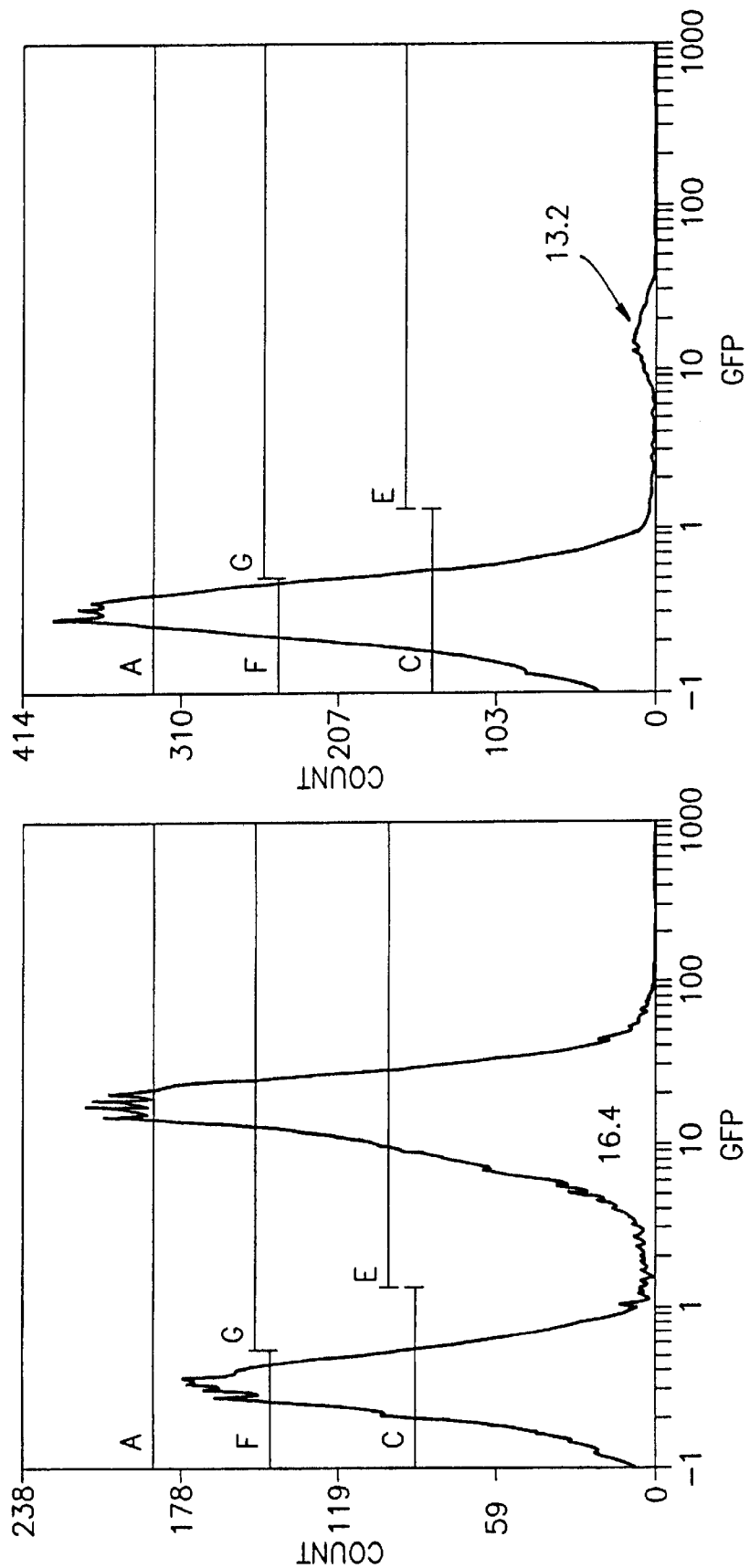

Isolated colonies were then inoculated into 45 ml of Super broth supplemented with DHB and 100 μg/ml carbenicillin and grown at 37° C. for 24 hours for analysis by flow cytometry of fluorescence. A second independent experiment was carried out exactly as the first, except isolated colonies were suspended in 500 μl of Super broth and 250 μl each inoculated into 45 ml paired Super broth cultures with or without 300 mM NaCl added to induce the $P_{ompC}$-gfpuv cassette; cultures were incubated at 37° C. for 48 hrs and again analyzed by flow cytometry, and results for both experiments are displayed in Table 5. Fluorescence histograms for uninduced and induced expression plasmids from experiment 2 are represented in FIG. 3.

TABLE 5

| | Experiment 1 | | | |
|---|---|---|---|---|
| Strain | Percent Dim Bacteria | Mean Fluorescence Of Dim Bacteria | Percent Fluorescing Bacteria | Mean Fluorescence |
| CVD908-htrA | 100 | 0.3 | | |
| CVD908-htrA(pJN72) | 3.1 | 0.2 | 96.9 | 10.2 |
| CVD908-htrA(pJN51) | 58.1 | 0.3 | 41.9 | 6.29 |
| CVD908-htrA(pJN10) | 5.4 | 0.2 | 94.6 | 7.43 |
| CVD908-htrA(pJN12) | 18.9 | 0.2 | 81.1 | 6.60 |

| | Experiment 2 | | | | | |
|---|---|---|---|---|---|---|
| Strain | O.D.$_{600}$ | +/− 300 Mm Nacl | % Dim Bacteria | Mean Fluorescence Dim Bacteria | % Fluorescing Bacteria | Mean Fluorescence |
| CVD908-htrA | 0.73 | − | 100 | 0.3 | 0 | 0 |
| CVD908-htrA(pJN72) | 0.75 | − | 2.3 | 0.3 | 97.7 | 11.7 |
| | 0.89 | + | 22.2 | 0.3 | 77.8 | 22.5 |
| CVD908-htrA(pJN51) | 0.62 | − | 56.3 | 0.3 | 43.7 | 18.4 |
| | 0.82 | + | 95.4 | 0.3 | 4.6 | 21.0 |
| CVD908-htrA(pJN10) | 0.72 | − | 1.7 | 0.3 | 98.3 | 8.3 |
| | 0.96 | + | 29.9 | 0.3 | 70.1 | 19.8 |
| CVD908-htrA(pJN12) | 0.47 | − | 45.2 | 0.3 | 54.8 | 16.4 |
| | 0.68 | + | 95.6 | 0.3 | 4.4 | 13.2 |

These flow cytometry results can be explained as follows: Expression of GFPuv (or other potentially detrimental heterologous antigen) from a multicopy expression plasmid such as pJN72 increases the metabolic stress on the CVD 908-htrA(pJN72) live vector, and increases plasmid instability in the absence of selection. Since the selectable marker of the expression plasmid encodes the secreted enzyme β-lactamase, then as time increases the concentration of carbenicillin in the surrounding medium declines, selective pressure decreases, and the frequency of plasmid loss increases; however, since multicopy plasmids are involved, relatively few bacteria succeed in losing all resident plasmids, but the average copy number of pJN72 per bacterium drops.

Quantitation by flow cytometry of GFPuv production for an uninduced population of healthy growing CVD 908-htrA (pJN72) indicates that the majority of bacteria express GFPuv and few non-fluorescing cells are detected (FIG. 3, panel A). However, increasing production of GFPuv by induction of the $P_{ompC1}$-gfpuv cassette increases the metabolic stress on CVD 908-htrA(pJN72), and although the production of GFP doubles, the percentage of non-fluorescent bacteria increases as more plasmids are lost from the population (FIG. 3B).

In a similar population of growing CVD 908-htrA (pJN51), each bacterium carries multicopy plasmids encoding both GFPuv and a PSK function. The frequency of plasmid loss for pJN51 remains the same as for pJN72, but in this case as individual bacteria lose copies of the expression plasmid, the 1:1 stoichiometry between the mRNA levels of hok and sok is disturbed, and production of Hok leads to cell death; therefore, the only CVD 908-htrA (pJN51) bacteria that will grow rapidly will be those which retain all of their expression plasmids. Accordingly, it is not surprising that quantitation by flow cytometry of GFPuv production for an uninduced population of healthy growing CVD 908-htrA(pJN51) now detects a population of fluorescing bacteria which displays levels of GFPuv fluorescence equivalent to those observed for CVD 908-htrA (pJN72) grown under inducing conditions (FIG. 3C vs FIG. 3B); however, the percentage of non-fluorescing bacteria rises to over half the overall population of organisms.

Figure 2A:
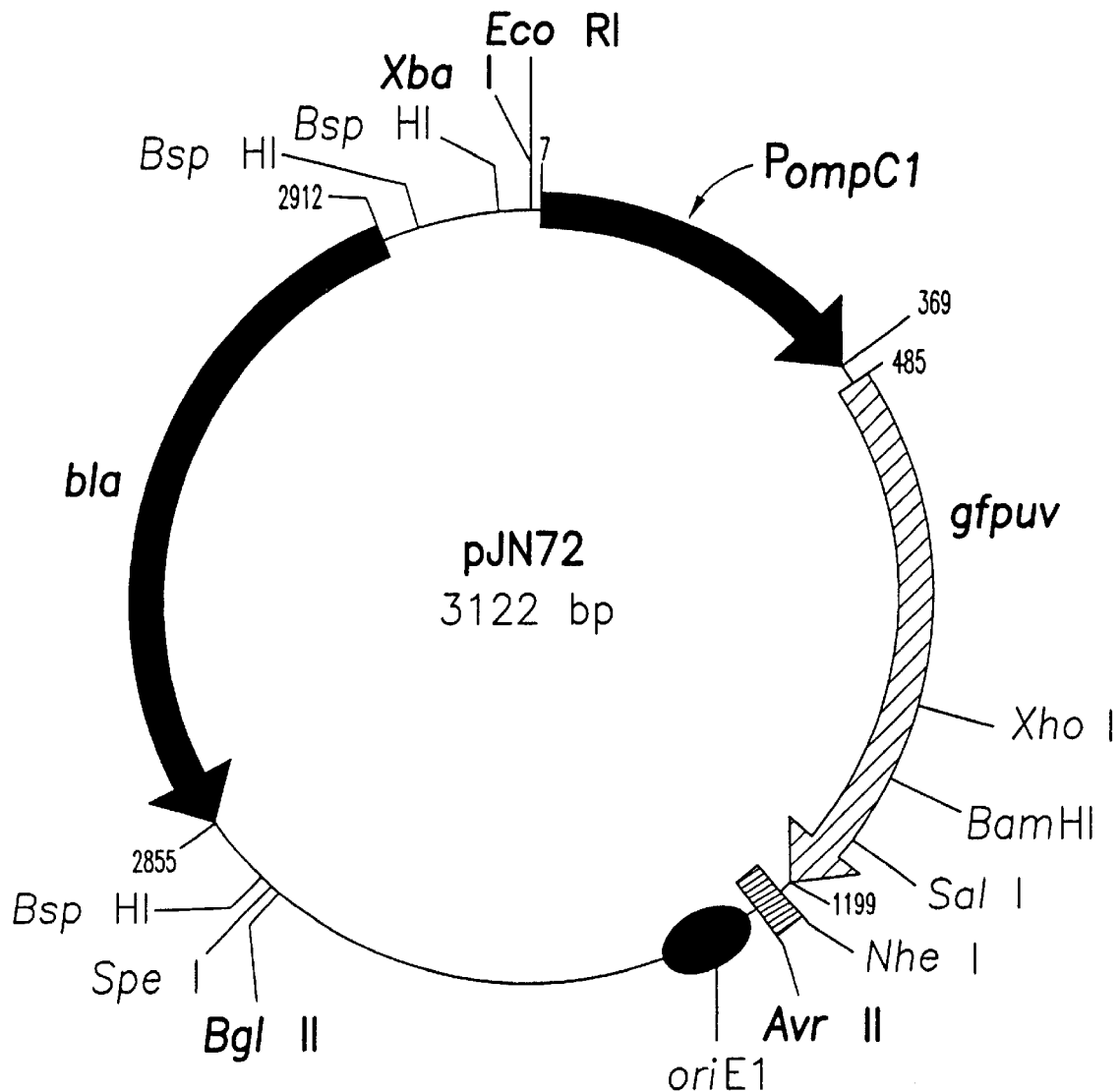
Figure 2B:
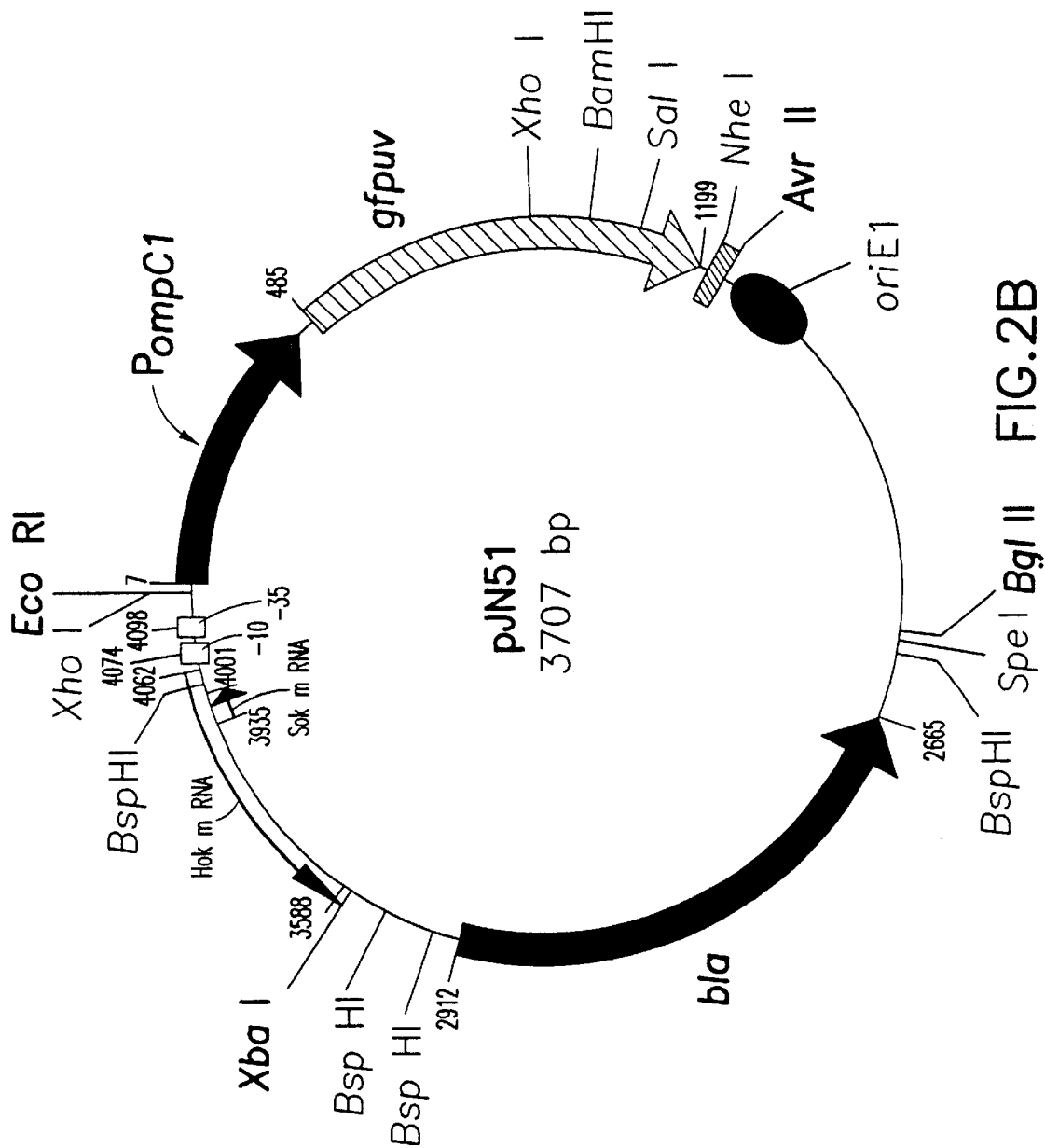
Figure 2C:
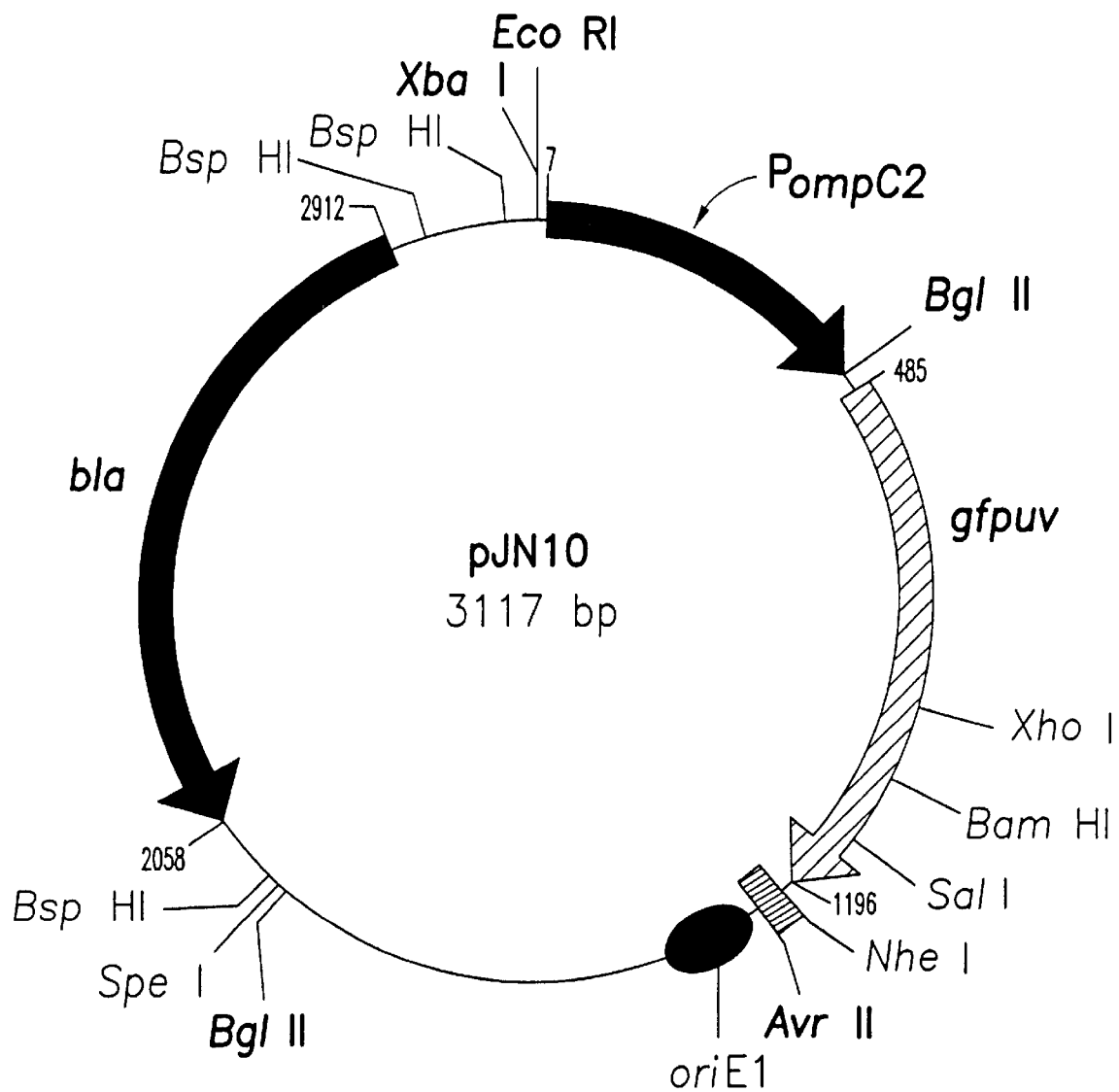
Figure 2D:
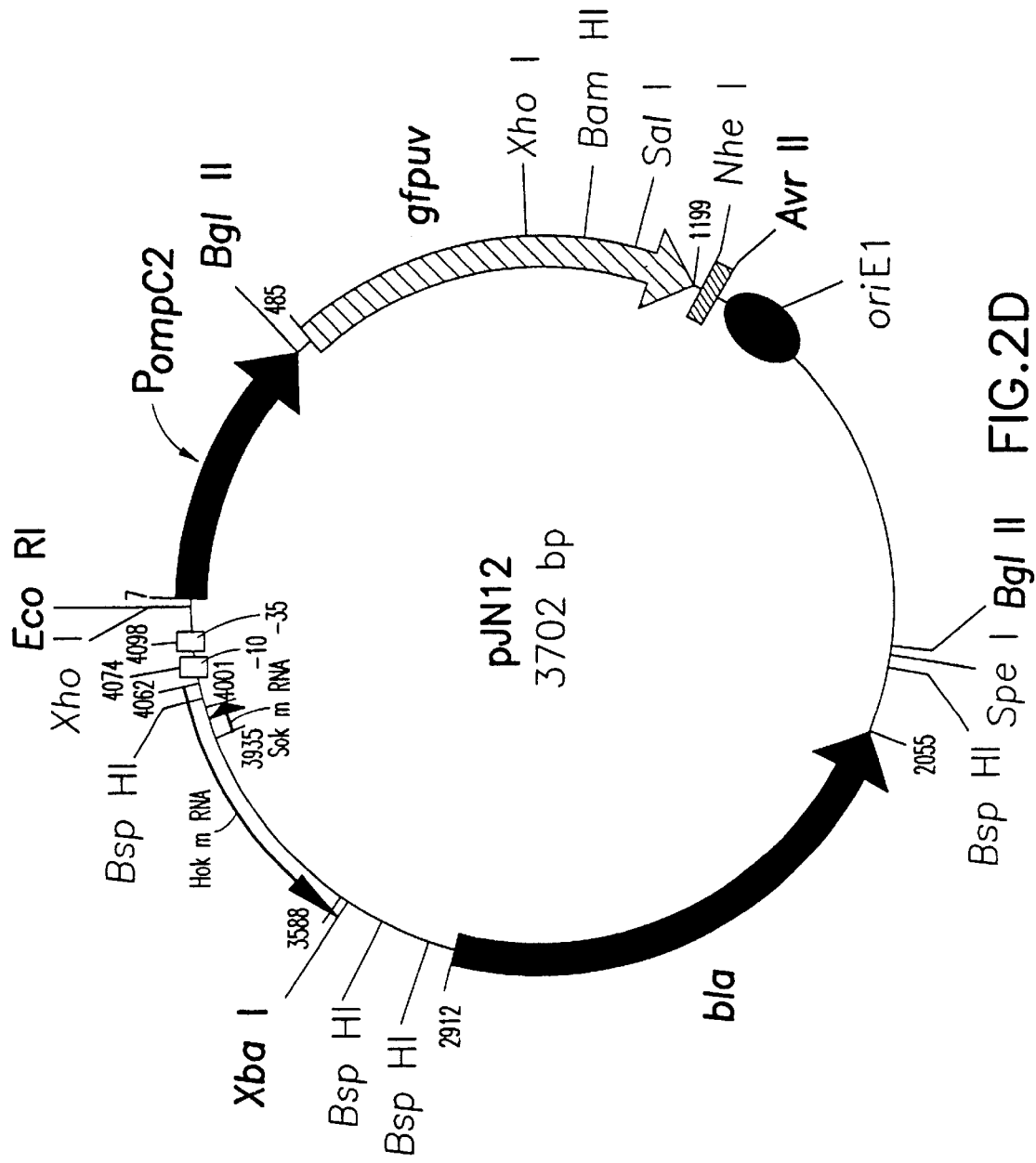

Increasing production of GFPuv in this population by induction of the $P_{ompC1}$-gfpuv cassette in CVD 908-htrA (pJN51) again increases the metabolic stress on the live vector, but now the percentage of non-fluorescent bacteria almost completely overtakes the few fluorescing bacteria as many plasmids are presumably lost from the population and bacteria are killed (FIG. 2D).

One would expect that if a weaker promoter is used to control expression of GFPuv, the overall fluorescence of the population would be decreased (compared to that observed for a similar population of organisms grown with a strong promoter expressing GFPuv under identical conditions), and the percentage of non-fluorescent bacteria should drop due to the overall drop in GFPuv synthesis. However, as seen in FIG. 3E–H, use of the weaker $P_{ompC2}$-gfpuv cassette did not significantly improve the viability of induced bacteria carrying a killing system, even though overall expression of GFPuv was reduced.

It is concluded that in order to maximize the percentage of a population of live vectors expressing the heterologous antigen of choice, it is not sufficient only to incorporate a PSK function into a given expression plasmid, whether it be a drug resistance marker, the asd system, an alternate ssb system, or the hok-sok killing system. In addition to optimizing copy number and expression levels, the segregation frequencies of these plasmids must also be improved to ensure that each daughter cell in an actively growing population will inherit at least one expression plasmid and those that do not will be killed and removed from the population. It is therefore within the scope of the present invention to provide an expression vector having a PSK function and further having optimized copy number and/or expression levels, coupled with incorporation of one or more SEG functions.

6.6 Complementation-based Killing System

It is also within the broad scope of the present invention to provide an expression plasmid comprising a complementation-based killing system, for example, a system involving the introduction of a defined non-revertible deletion mutation into the chromosomal ssb locus of CVD908-htrA by homologous recombination, and trans-complementation of this lesion using multicopy plasmids carrying ssb.

To carry out such constructions requires cloning the relevant section of the S. typhi chromosome encompassing the ssb gene and flanking sequences, into which specific in-frame deletions can be introduced for chromosomal mutagensis. No complete nucleotide sequence data have been published for the ssb gene or flanking gene sequences within the chromosome of S. typh screening plasmids for the presence of the unique Spe I restriction site. pJN14 and pJN15 will then be cleaved with Avr II-Bgl II, and the oriE1 replicons replaced with the ori15A Avr II-Bam HI cassette from pGEN3 (SEQ. I.D. NO.2), or the ori101 Avr II-Bam HI cassette from pGEN4 (SEQ. I.D. NO.3), creating pJN16 and pJN17. The influence of the hok-sok locus and copy number within the isogenic set of expression plasmids pJN14, pJN15, pJN16, and pJN17, can then be examined as transcription levels are kept relatively constant within the $P_{ompC1}$-gfpuv cassette. Note that since the origins of replication within these expression plasmids are sequestered by transcriptional termination signals at both the 5'-proximal and 3'-distal termini, variations in copy number due to read-through transcription from other promoters within these plasmids can be minimized. To examine the effect of promoter strength, an additional set of analogous expression plasmids can also be constructed in which the $P_{ompC1}$ promoter cassette is replaced by the $P_{ompC2}$ cassette.

It is within the broad scope of the present invention to determine the stability of these two sets of expression plasmids within CVD 908-htrA to improve and/or optimize the amount of heterologous antigen produced by a population of live vectors grown for immunization. Plasmid stability can be estimated by examining cultures grown both under selection (25 μg/ml neomycin) and grown without selection by serially passaging cultures using 1:10$^6$ dilutions as described by Summers and Sheratt Cell, 36:1097, 1984 (incorporated herein by reference), except cultures can be grown in Super broth with or without 300 mM NaCl rather than minimal medium. The frequency of plasmid loss can be estimated using the ratio of colony forming units on selective medium versus colony forming units on non-selective medium after passaging live vectors for 0, 25, 50, and 100 generations. The mean fluorescence of bacteria carrying optimized expression plasmids encoding GFPuv and grown with or without selection can then be examined using flow cytometry, and expression of GFPuv from promising constructs by Western immunoblot analysis using a commercially available monoclonal antibody specific for GFP (Clontech) can be confirmed.

Furthermore, it is within the scope of the present invention to employ within the expression plasmids disclosed herein the proteic addiction system phd-doc of the temperate bacteriophage P1. As described above, in proteic addiction systems both the toxin and antitoxin involve proteins, rather than only RNAs. These proteins are synthesized from operons in which the gene encoding the antitoxin is upstream of the gene encoding the toxin.

The phd-doc system encodes two small proteins: the toxic 126 amino acid Doc protein which causes death on curing by an unknown mechanism, and the 73 amino acid Phd antitoxin which prevents host death, presumably by binding to and blocking the action of Doc. Synthesis of Phd and Doc is translationally coupled, with Phd synthesis exceeding synthesis of the toxic Doc protein. In addition, transcription of the operon is autoregulated at the level of transcription. Although Doc appears to be relatively resistant to proteolytic attack, Phd is susceptible to cleavage by the ClpXP serine protease of E. coli.

The PSK mechanism of a plasmid-encoded phd-doc locus is therefore activated when bacteria spontaneously lose the resident plasmid, which leads to degradation of the Phd antitoxin and subsequent activation of the Doc toxin which causes cell death. Therefore, proper function of the phd-doc system within S. typhi requires the presence of the ClpXP serine protease; using the published sequence of the E. coli clpP-clpX operon (GenBank Accession Numbers J05534 and L18867 respectively) PCR of CVD908htrA chromosomal DNA has been used to demonstrate a product of the expected size presumably corresponding to the clpP-clpX operon. PCR techniques can also be employed to construct an Eco RI-Xba I phd-doc cassette for replacement of the Eco RI-Xba I hok-sok cassette in promising expression plasmids.

The present invention can also provide an expression plasmid, expressing a

Plasmid Maintenance System comprising at least one partition locus and a non-catalytic PSK function, based on trans-complementation of an otherwise lethal deletion mutation of the CVD 908-htrA chromosomal ssb gene to improve the observed plasmid-based expression of heterologous antigens within CVD908-htrA.

The chromosomal ssb locus from CVD 908-htrA can be cloned to determine the nucleotide sequence of the transcriptional control region and ssb structural gene, and to construct defined in-frame deletions to inactivate chromosomally-encoded SSB. The intact ssb gene can then be inserted into expression plasmids to optimize expression of the test heterologous antigen, GFPuv.

The non-catalytic PSK function can function as a selectable marker using the ssb system. Although SSB is an essential protein, it has no catalytic activity to produce a required product that could be added to the growth medium allowing ssb mutants to grow. The key to the success of the proposed chromosomal constructions rests in the use of two non-leaky conditionally replicative plasmids. One of these conditional replicons is the temperature-sensitive suicide vector used f or chromosomal mutagenesis, derived from pIB307 and described above; this suicide vector contains the origin of replication from pSC101 encoding the temperature-sensitive RepA protein essential to the function of ori101. The other critical conditional replicon provides transient expression of SSB protein in CVD 908-htrA live vectors deleted for ssb, prior to introduction of expression plasmids carrying the essential ssb gene.

This conditional replicon, designated pCON (conditional replicon) has recently been constructed, which contains the minimum functioning origin of replication for oriE1 without the critical promoter controlling synthesis of RNA I (the promoter controlling synthesis of the antisense RNA II has not been altered); this RNA I promoter has been replaced by the Lac repressor-controlled trc promoter, and the required lacI gene encoding the repressor has also been included on this plasmid to ensure control of plasmid replication by the presence or absence of IPTG. IPTG is a chemical analog of galactose which cannot be cleaved by the enzyme β-galactosidase. IPTG induces activity of the E. coli lac operon by binding and inactivating the lac repressor. In the absence of IPTG, no colony forming units for CVD908-htrA(pCON) were detected in the presence of carbenicillin selective pressure.

This novel approach significantly extends the range of chromosomal loci in live vectors now available for mutagenesis.

An expected 3.6 kb fragment for characterization by direct sequence analysis to define the uvrA-ssb chromosomal locus from CVD908-htrA has been successfully amplified. Primers homologous to sequences within the S. typhi soxS gene are currently being used in combination with primers designed from the partial sequence of the S. typhi ssb gene to amplify regions of the chromosome flanking the other side of the CVD908-htrA uvrA-ssb locus. The critical clones encompassing ssb and flanking regions necessary for the chromosomal crossovers can then be recovered. Alternatively, a cosmid gene bank of chromosomal DNA from CVD 908-htrA can be established and the necessary clone containing ssb and flanking sequences can be identified using radioactively labelled single-stranded probes designed from the known partial sequence of the *S. typhi* Ty2 ssb gene. Once required clones containing the ssb locus have been obtained and the sequences for the uvrA-ssb intergenic control region and ssb are defined, one can proceed with the chromosomal constructions.

A suicide vector can be constructed in which the sacB-neo cassette has been inserted upstream of the intact ssb gene, within the uvrA-ssb intergenic control region, and transcribed toward ssb to ensure necessary synthesis of SSB. This sacB-neo-ssb cassette can then be crossed into the chromosome of CVD 908-htrA to associate a counter-selectable marker with the ssb locus. Merodiploids can be selected by plating on selective medium containing 25 $\mu$g/ml neomycin and incubating at the non-permissive temperature of 42° C. The required CVD 908-htrA ssb:: sacB-neo strain can then be selected by plating on selective medium containing 25 $\mu$g/ml neomycin and incubating at 30° C.

It is also within the scope of the present invention to prepare a trc-controlled conditional replicon encoding SSB (designated pCONssb) and to electroporate this conditional replicon into CVD 908-htrA ssb::sacB-neo; the desired CVD 908-htrA ssb:: sacB - neo(pCONssb) colonies can be recovered on neomycin-containing medium supplemented with carbenicillin and 2 mM IPTG to allow for selection and replication of pCONssb. A further suicide vector can be constructed in which a defined in-frame deletion mutation which inactivates ssb can be introduced into a chromosomal fragment encoding ssb and flanking regions. This Δssb suicide vector can then be electroporated into CVD 908-htrA ssb::sacB-neo(pCONssb); merodiploids at the chromosomal ssb locus can be selected for by plating on medium supplemented with 20 $\mu$g/ml chloramphenicol, 25 $\mu$g/ml neomycin, and 2 mM IPTG, and incubating at the non-permissive temperature of 42° C. Resolution of merodiploids and recovery of Δssb in the chromosome can be accomplished by plating at 30° C. on medium containing 10% sucrose (to counterselect for loss of the sacB-neo genes), plus carbenicillin and IPTG (to ensure replication of pCONssb and continued synthesis of SSB), generating CVD 908-htrA ssb(pCONssb).

An expression plasmid carrying the wildtype ssb gene can then easily be introduced into CVD 908-htrAssb(pCONssb) to replace pCONssb, by electroporation and selection of the desired colonies at 37° C. on non-selective medium without IPTG or carbenicillin. The ssb cassette can be inserted as an Xba I-Spe I fragment into all promising expression plasmids to replace the aph or other selection cassette.

The stability of plasmids carrying the ssb PSK function can then be determined using the methods described above.

Expression plasmids can be employed which carry mutated ssb genes analogous to the ssb-1 point mutations identified in *E. coli*. As described above, such mutations do not complement chromosomal lesions in the ssb gene of *E. coli* unless the mutant SSB-1 proteins are expressed in high enough amounts from multicopy plasmids. This approach can therefore enhance the maintenance of proposed multi-copy plasmids containing ori15A or oriE1 origins of replication.. This is not to say that ssb technology cannot be used with other systems to further enhance plasmid maintenance. Indeed, combinations of killing systems reduce loss frequencies by another $10^3$ fold versus loss frequencies observed using single killing systems. However, use of multiple PSK functions in expression plasmids to optimize synthesis of heterologous antigens must be balanced against any additional physiological stresses imposed by multiple killing systems upon the live vector.

A Plasmid Maintenance System based solely on the use of a PSK function is generally insufficient to guarantee the inheritance of expression plasmids during division of a host bacterium. Without a partition function to reduce or eliminate the random inheritance of expression plasmids, overall expression of heterologous antigens in a live vector population will drop and reduce immunogenicity. The random segregation of expression plasmids carrying only a PSK system can be eliminated by insertion of a partition locus. Accordingly, in a preferred mode, the present invention comprises an expression plasmid comprising both a PSK function and at lease one partitioning function.

The par locus from pSC101 can be used in combination with the oriE1 or ori15A origin of replication, and the parA active partition locus from pR1 in combination with the oriE1, the ori15A and ori101 origins.

As previously stated, the presence of a PSK function per se does not affect the frequency at which a given expression plasmid is inherited; if such a plasmid is unstable, then loss of plasmids encoding killing functions is expected to produce a decrease in the overall growth rate of a population of bacteria carrying such plasmids. When the par locus from pSC101 is incorporated into expression plasmids that are potentially toxic to host bacteria, growth rates are improved, presumably due to a reduction of loss frequencies for resident plasmids. In addition, introduction of the par locus into medium copy number plasmids such as pBR327 improves plasmid stability. Insertion of the par locus into high copy number pUC plasmids can completely stabilize these plasmids in bacteria serially passaged under non-selective conditions for up to 100 generations. The par locus can therefore improve segregation frequencies of our expression plasmids in CVD 908-htrA.

Since par does not encode any proteins, use of this locus in expression plasmids can minimize any metabolic stress on the live vector due to synthesis of additional foreign proteins. If the par locus proves insufficient for significantly improving segregation frequencies, one can consider use of the parA locus from pR1. The parA active partitioning system is preferred because it naturally resides within the same plasmid from which the hok-sok locus originates and is, therefore, compatible with hok-sok in the expression plasmids.

It is also within the scope of the present invention to provide expression plasmids which carry a unique Spe I restriction site (see FIG. 2). Using PCR methods, a Spe I-Nhe I cassette encoding the par locus from pSC101 can be constructed for insertion into the Spe I site of plasmids carrying a PSK function. Plasmids in which par is present in both orientations can be obtained and examined for any effect of orientation on plasmid maintenance. Since no proteins are encoded by par, the effects of transcription originating from other promoters within the expression plasmid are expected to be minimal. However, this becomes a concern when attempting to exploit an active partitioning locus since proteins expressed by such loci are required for proper function of the locus and must be synthesized at their natural levels. parA-aph Spe I-Eco RI cassettes in which the aph gene and parA operon are divergently transcribed and are separated by an Xba I site can be constructed. This cassette can be used to replace the bla cassettes of pJN72 and pJN10 (see FIG. 2), and the aph cassette can later be replaced by the ssb gene or other appropriate locus; origins of replication can then be replaced by oriE1, ori15A or ori101 Bam HI-Avr II cassettes from pGEN2 (SEQ. I.D. NO.1), pGEN3 (SEQ. I.D. NO.2) or pGEN4 (SEQ. I.D. NO.3) respectively (see FIG. 1).

The stability of plasmids carrying Plasmid Maintenance Systems, comprised of partition and killing functions can then be determined using the methods described above. These results can be compared to the stability of plasmids carrying individual partition or killing cassettes, or no maintenance functions at all.

As mentioned above, another active partitioning locus which functions in Salmonella is naturally present on the virulence plasmids of *S. typhimurium*. Such partition loci are well conserved among Salmonella virulence plasmids, and when a 3.9 kb restriction fragment encoding this locus is introduced onto the lower copy number plasmids containing ori15A, the observed plasmid stability increases from 34% plasmid-containing cells to 99% plasmid-bearing cells after 50 generations.

It is within the broad practice of the present invention to insert this active partition locus into the expression plasmids of the present invention. The combination of an active partitioning locus with our proposed ssb technology is expected to significantly improve plasmid maintenance and overall viability of CVD 908-htrA carrying these plasmids.

Stx2 is a highly potent toxin strongly implicated in the development of most HUS cases in the United States. Therefore, to remove any risk of residual toxicity associated with expression of a genetically detoxified holotoxin within CVD 908-htrA, the B subunits of Stx2 can be used as antigens to elicit serum neutralizing antibodies which block binding of the B pentamer to $Gb_3$. It is well established that laboratory strains of *E. coli*, capable of plasmid-based expression of wild type Shiga toxins, are lethal when orally inoculated into mice at high doses. It has further been demonstrated by ELISA techniques that the biologically relevant pentameric form of the holotoxin assembles correctly and is able to bind to its $Gb_3$ receptor. It is within the broad practice of the present invention to provide expression plasmids expressing $Stx2_B$ subunits within CVD 908-htrA resulting in formation of pentamers. Coexpression of an A2 domain can further increase formation of these pentamers.

An operon can be constructed encoding a non-toxic truncated form of the A subunit in addition to the B subunit of Stx2, designated $stx2_{A2B}$. The truncated A subunit will consist of the natural leader sequence of Stx2 fused to the A2 domain, and will therefore not contain the catalytic site responsible for eucaryotic cell death. This genetically engineered operon encoding $Stx2_{A2B}$ can be expressed within CVD 908-htrA from multicopy plasmids which carry an optimized Plasmid Maintenance System. Expression of $Stx2_{A2B}$ pentamers can be compared to expression of $Stx2_B$ pentamers from an independent cassette encoding only B subunit. It can be determined if the A2 peptide can enhance proper assembly of B subunits, preserving neutralizing epitopes within the 5 receptor binding clefts of the B subunit pentameric ring.

Coexpression of the A2 domain of Stx2 may promote proper assemblage of β-pentamers for two reasons. First, crystal structure studies have now demonstrated that the tertiary structure of the B subunits of the heat-labile enterotoxin LT and Stx1 are remarkably similar, despite differences in size and a lack of amino acid sequence identity. It has been further described by Streatfield et al. that the A2 domain of the closely related cholera and LT enterotoxins promotes holotoxin assembly and stability in vivo. It is therefore within the scope of the invention to provide an expression plasmid wherein expression of the A2 domain can enhance formation of Stx2 B pentamers. The second reason for coexpression of the A2 domain relates to the preservation of the conformation of critical neutralizing epitopes within the binding clefts of the pentamers. The structure of the B pentamer within the holotoxin (in which the A subunit is coordinated with the B pentamer via the A2 domain) has more of a 5-fold symmetry than is observed for the crystal structure of the pentamer alone. It is therefore within the scope of the invention to provide an expression plasmid wherein coexpression of A2 will allow formation of pentamers which more closely resemble naturally occurring pentamers.

Using PCR, an $stx2_{A2B}$ Bgl II-Nhe I cassette can be constructed encoding a truncated Stx2 A subunit in which the complete leader sequence including the terminal serine residue 22 is fused to residues 262–297 of the mature Stx2 A subunit which will form the α-helix that inserts into the central pore of the B pentamer ring. In order to preserve the natural relative levels of synthesis of the two subunits, the natural ribosome binding sites upstream of both the A and B subunits can be preserved.

An $stx2_B$ Bgl II-Nhe I gene cassette can also be constructed encoding $Stx2_B$ in which an optimal ribosome binding site has been introduced to promote optimum synthesis of B subunits. Either of these two cassettes can then be inserted into optimized expression plasmids which carry Plasmid Maintenance Systems, replacing gfpuv Bgl II-Nhe I gene cassettes. Expression of pentamers can be further improved by adjusting the copy number of the expression plasmids, using the origin of replication cassettes from either pGEN2 (SEQ. I.D. NO.1), pGEN3 (SEQ. I.D. NO. 2) or pGEN4 (SEQ. I.D. NO.3), and using alternate promoters such as the anaerobically activated promoter $P_{nir15}$ from pTETnir 15 to control transcription of these heterologous antigen cassettes.

Residual cytotoxic activity in sonicates of CVD908-htrA expressing $Stx2_{A2B}$ and $Stx2_B$ can be detected using the Vero cell assay. In addition to Vero cells, human renal glomerular microvascular endothelial (HRMEC) cells can be used to establish the baseline toxicity of purified Stx2 (necessary for proposed neutralization assays described below). This assay can be used to confirm residual toxicity results observed for sonicates assayed with the standard Vero cell assay.

Generation of immune responses directed against specific immunogens expressed within attenuated Salmonella can be investigated using inbred strains of BALB/c mice.

BALB/c mice have been selected because of their serum immunoglobulin responses to intranasal immunization with live vaccine carrier strains of *Salmonella typhi*.

Once CVD908-htrA strains have been established carrying stable expression plasmids, immunogenicity experiments can be carried out using constructs expressing either $Stx2_{A2B}$ or $Stx2_B$.

BALB/c mice can be randomized to be immunized intranasally with one of three vaccine strains: 1) CVD908-htrA; 2) CVD908-htrA expressing $Stx2_{A2B}$ from unaltered expression plasmids [designated here as CVD908-htrA ($pStx2_{A2B}$)], 3) CVD908-htrA expressing $Stx2_{A2B}$ from expression plasmids carrying the optimized Plasmid Maintenance system [designated CVD908-htrA($pStx2_{A2B}$pm)]. Two intranasal doses ($10^{10}$ CFU in 30 µl) of live vector vaccine can be administered spaced 28 days apart and sera can be collected before and 28, 42 and 60 days thereafter to measure titers of Stx2 antitoxin by ELISA, and Stx2 neutralizing antitoxin by the Vero cell assay. The Vero cell assay neutralizing titers are the critical endpoints of the experiment.

Based on previous data, it is expected that only 67% of mice given the parent CVD 908-htrA strain group will attain Shiga toxin neutralizing antitoxin titers of $\geq 1:50$ and only 10% of mice will achieve titers of $\geq 1:200$. Based on the hypothesis that in mice immunized with CVD908-htrA(p Stx2$_{A2B}$pm) at least 70% will reach Stx2 antitoxin neutralizing titers of 1:200, inclusion of 16 mice per group will provide 80% power to detect a significant difference for each Stx2 versus the control or between the two expression plasmids with or without the maintenance system (alpha= 0.0167, two-tail test, Bonferroni correction for multiple comparisons).

After collecting the final serum samples at day 60, mice can be orally challenged with $10^{10}$ CFU in 100 μl of the $E.$ $coli$ strain C600(933W) expressing toxigenic Stx2, and observed for 10 days for mortality. Assays for Stx2 neutralizing antitoxin using the HRMEC assay can also be performed to determine the titer of Stx2 neutralizing antibodies which block toxicity to the relevant human tissue postulated to be involved in HUS. These experiments can be repeated using CVD908-htrA expressing Stx2$_B$ alone to determine if coexpression of A2 enhances the titer of Stx2 neutralizing antibodies which block binding of the toxin.

It should be noted that one investigator has proposed that Stx 1 binds to Burkitt's lymphoma cells and a subset of tonsillar B lymphocytes located in germinal centers, causing them to undergo apoptosis. This proposition has raised some concerns about the safety of immunizing humans with Stx1 B subunit. It is not known if this observation applies to Stx2 B subunit as well. Under any circumstances, in the future, should this concern become substantiated by clinical observations, it will be possible to alter Gb$_3$ binding of either B subunit or mutant Stx2 by site-directed mutagenesis, as described below.

It is within the scope of the invention to provide an expression plasmid which expresses within attenuated $S.$ $typhi$ live vector strains a genetically detoxified and safe Stx2 holotoxin that is non-toxic yet stimulates neutralizing antitoxin.

holotoxin can be expressed from multicopy plasmids which carry an optimized Plasmid Maintenance System.

A minimum of two well separated sets of specific point mutations can be introduced into the open reading frames encoding both the A and B subunits, in order to remove the possibility of genetic reversions which restore toxic activity to the holotoxin. The sets of point mutations can be separated within each reading frame to remove the possibility of a single rare reversion event reversing the influence of mutations within a single domain. It is known that replacement of the phenylalanine residue 30 of Stx1 with alanine does not alter the three dimensional structure of the resulting holotoxin. The identical substitution of the analogous residue 29 can therefore be introduced within the B subunit of Stx2, as the first mutation to detoxify Stx2. This construct can be tested for immunogenicity and protection in mice. Where protection is achieved, each additional mutation can be sequentially introduced and assessed for immunogenicity and protection until all four mutations are prepared without significantly reducing immunogenicity of the mutant holotoxin.

It must be emphasized that the original nucleotide sequence reported for the stx2 operon incorrectly predicted the mature A subunit to be comprised of 296 residues, rather than 297; the amino acid coordinates used here for mature Stx2 subunits are based on GenBank Accession Number X07865, as revised by C. Schmitt, and referenced in the Addendum of Jackson et al., *Journal of Bacteriology* 172:3346, p. 3349, 1990 (incorporated herein by reference). Based on these coordinates, the following point mutations can be engineered to create the desired mutant holotoxins: E167D (i.e. Glu 167→Asp) and W202L (i.e. Trp 202→Leu) to detoxify Stx2a; and Y28F+W29A (i.e. Tyr 28→Phe+ Trp29→Ala) and G59D (i.e. Gly59→Asp) to inactivate the binding sites of Stx2B.

Using overlapping PCR, the following mutations can be introduced into a Bgl II-Nhe I gene cassette containing mutated stx2 operons:

| Subunit | Mutation(s) | Sequences Changed | | | Restriction Site Introduced (Or Deleted) |
|---|---|---|---|---|---|
| A | E167D | (797) – ACA GCA GAC GCG TTA – (811) | (SEQ ID NO:4) | | Mlu I |
|   | W202L | (902) – CTG AAC CTA GGG CGA – (916) | (SEQ ID NO:5) | | Avr II |
| B | Y28F + W29A | (1345) – GAA TCc GCg ACC AGT – (1359) | (SEQ ID NO:6) | | Eco RI, Nru I (overlapping) |
|   | G59D | (1435) – GAA TCA GAT TCT GGA – (1449) | (SEQ ID NO:7) | | Bsp E1 site removed by C → T substitution. |

The nucleotide sequence coordinates within the stx2 operon are listed in parenthesis. Point mutations are listed in oversized typeface. Restriction sites introduced (or removed) by these point mutations are denoted by underlined bases.

It is within the broad scope of the invention to prepare a detoxified Stx2 holotoxin for expression within CVD908-htrA which properly assembles into the biologically relevant A1:B5 configuration, preserving neutralizing epitopes within the catalytic domain (i.e. Stx2$_A$), as well as preserving the 5 receptor binding clefts of the B subunit (i.e. Stx2$_B$) pentameric ring. This genetically engineered mutant Stx2

The codon usage tables compiled for both $E.$ $coli$ and $S.$ $typhi$ have been employed in the design of the point mutations. With the exception of the codon used for the Leu substitution within the A subunit, none of the codons proposed here is expected to be rare in $S.$ $typhi$. Mutated holotoxin cassettes can be inserted into our optimized expression plasmids, replacing gfpuv cassettes. Lower copy number plasmids derived from pGEN3 (SEQ. ID. NO.2) and pGEN4 (SEQ. ID. NO.3) can be used for these constructions. Restriction sites introduced (or deleted) within the stx2 operon can be used to rapidly identify the desired constructs, and the nucleotide sequence of promising constructs can be determined to verify the integrity of each mutation. Promising constructs can be electroporated into CVD908-htrA, and plasmid maintenance determined as above. Western immunoblot analysis, using monoclonal antibodies 11E10 (specific for the A subunit of Stx2) and BC5 (specific for the B subunit of Stx2), can be used to quantify expression of mutant Stx2 within CVD908-htrA.

Residual cytotoxic activity in sonicates of CVD908-htrA expressing mutant Stx2 holotoxin can be detected using the Vero cell assay and the HRMEC assay, as described above.

Once CVD908-htrA strains have been prepared to carry stable expression plasmids, an initial immunogenicity experiment can be carried out using constructs expressing $Stx2_{Y28F+W29A}$ (designated here as Stx2-1). BALB/c mice can be randomized to be immunized intranasally with one of three vaccine strains: 1) CVD908-htrA; 2) CVD908-htrA expressing Stx2-1 from unaltered expression plasmids [designated here as CVD908-htrA(pStx2-1)], 3) CVD908-htrA expressing Stx2-1 from expression plasmids carrying the optimized Plasmid Maintenance system [designated CVD908-htrA(pStx2-1 pm)]. Two intranasal doses ($10^{10}$ CFU in 30 $\mu$l) of live vector vaccine can be administered spaced 28 days apart and sera can be collected before and 28, 42 and 60 days thereafter to measure titers of Stx2 antitoxin by ELISA, and Stx2 neutralizing antitoxin by the Vero cell assay. The Vero cell assay neutralizing titers are the critical endpoints of the experiment.

Based on previous data, only 67% of mice given the parent CVD 908-htrA strain group are expected to attain Shiga toxin neutralizing antitoxin titers of $\geq$1:50 and only 10% of mice would achieve titers of $\geq$1:200. It is expected that in mice immunized with CVD908-htrA(pStx2-1 pm) at least 70% will reach Stx2 antitoxin neutralizing titers of 1:200. Accordingly, inclusion of 16 mice per group will provide 80% power to detect a significant difference for each Stx2 versus the control or between the two expression plasmids with or without the maintenance system (alpha= 0.0167, two-tail test, Bonferroni correction for multiple comparisons).

After collecting the final serum samples at day 60, mice can be orally challenged with $10^{10}$ CFU in 100 $\mu$l of the E. coli strain C600(933W), expressing toxigenic Stx2, and observed for 10 days for mortality.

Experiments assaying for Stx2 neutralizing antitoxin using the HRMEC assay can be used to determine the titer of Stx2 neutralizing antibodies which block toxicity to the relevant human tissue postulated to be involved in HUS.

Different promoters can be used to optimize holotoxin expression. Mutant stx2 operons can be introduced as Bgl II-Bam HI cassettes into the Bgl II site of a given expression plasmid, creating stx2(mutant)-gfpuv operons. This will not involve re-engineering of the cassettes from above since juxtaposed Xba I-Bam HI sites 3' can be introduced into the cassettes constructed above (i.e. an Xba I-Bam HI-Nhe I 3'terminus).

The advantage of constructing stx2(mutant)-gfpuv operons is that transcription levels for mutant stx2 can be monitored by examining the expression of GFPuv, which is translated from the distal gene of the polycistronic stx2 (mutant)-gfpuv mRNA. Using such a system, the transcription of mutant stx2 genes can be optimized and can be monitored indirectly by flow cytometry and confirmed by Western immunoblot analysis. The gfpuv gene of promising constructs can then be deleted by digestion with Xba I and Nhe I, and recircularized constructs can be purified for electroporation into CVD908-htrA.

7. REFERENCES

The disclosures of the following references are incorporated herein in their entirety:

Acheson, D. W. K. 1998. Nomenclature of enterotoxins. Lancet 351:1003.

Acheson, D. W. K., M. M. Levine, J. B. Kaper, and G. T. Keusch. 1996. Protective immunity to Shiga-like toxin I following oral immunization with Shiga-like toxin I B-subunit-producing Vibrio cholerae CVD 103-HgR. Infection and Immunity 64:355.

Austin, S. J. 1988. Plasmid partition. Plasmid 20:1.

Barry, E. M., O. G. Gomez-Duarte, S. Chatfield, R. Rappuoli, M. Pizza, G. Losonsky, J. E. Galen, and M. M. Levine. 1996. Expression and immunogenicity of pertussis toxin S1 subunit-tetanus toxin fragment C fusions in Salmonella typhi vaccine strain CVD 908. Infection and Immunity 64:4172.

Bast, D. J., J. L. Brunton, M. A. Karmali, and S. E. Richardson. 1997. Toxicity and immunogenicity of a verotoxin 1 mutant with reduced globotriaosylceramide receptor binding in rabbits. Infection and Immunity 65:2019.

Baumler, A. J., J. G. Kusters, I. Stojiljkovic, and F. Heffron. 1994. Salmonella typhimurium loci involved in survival within macrophages. Infection and Immunity 62:1623.

Blattner, F. R., G. Plunkett III, C. A. Bloch, N. T. Perna, V. Burland, M. Riley, J. Collado-Vides, J. D. Glasner, C. K. Rode, G. F. Mayhew, J. Gregor, N. W. Davis, H. A. Kirkpatrick, M. A. Goeden, D. J. Rose, B. Mau, and Y. Shao. 1997. The complete genome sequence of Escherichia coli K-12. Science 277.1453.

Blomfield, I. C., V. Vaughn, R. F. Rest, and B. I. Eisenstein. 1991. Allelic exchange in Escherichia coli using the Bacillus subtilis sacB gene and a temperature-sensitive pSC101 replicon. Molecular Microbiology 5:1447.

Boe, L. and K. V. Rasmussen. 1996. Suggestions as to quantitative measurements of plasmid loss. Plasmid 36153.

Boe, L., K. Gerdes, and S. Molin. 1987. Effects of genes exerting growth inhibition and plasmid stability on plasmid maintenance. Journal of Bacteriology 169.4646.

Bokman, S. H. and W. W. Ward. 1981. Renaturation of Aequorea green-fluorescent protein. Biochemical and Biophysical Research Communications 101:1372.

Bosworth, B. T., J. E. Samuel, H. W. Moon, A. D. O'Brien, V. M. Gordon, and S. C. Whipp. 1996. Vaccination with genetically modified Shiga-like toxin IIe prevents edema disease in swine. Infection and Immunity 64:55.

Bouvier, J., C. Richaud, W. Higgins, O. Bogler, and P. Stragier. 1992. Cloning, characterization, and expression of the dapE gene of Escherichia coli. Journal of Bacteriology 174:5265.

Boyd, B. and C. A. Lingwood. 1989. Verotoxin receptor glycolipid in human renal tissue. Nephron 51:207.

Butterton, J. R., E. T. Ryan, D. W. Acheson, and S. B. Calderwood. 1997. Coexpression of the B subunit of Shiga toxin 1 and EaeA from enterohemorrhagic Escherichia coli in Vibrio cholerae vaccine strains. Infection and Immunity 65:2127.

Calderwood, S. B., D. W. K. Acheson, G. T. Keusch, T. J. Barrett, P. M. Griffin, N. A. Strockbine, B. Swaminathan, J. B. Kaper, M. M. Levine, B. S. Kaplan, H. Karch, A. D. O'Brien, T. G. Obrig, Y. Takeda, P. I. Tarr, and I. K. Wachsmuth. 1996. Proposed new nomenclature for SLT (VT) family. *ASM News* 62.118.

Calderwood, S. B., F. Auclair, A. Donohue-Rolfe, G. T. Keusch, and J. J. Mekalanos. 1987. Nucleotide sequence of the Shiga-like toxin genes of *Escherichia coli*. *Proceedings of the National Academy of Sciences USA* 84:4364.

Carlini, L. E., R. D. Porter, U. Curth, and C. Urbanke. 1993. Viability and preliminary in vivo characterization of site-specific mutants of *Escherichia coli* single-stranded DNA-binding protein. *Molecular Microbiology* 10.1067.

Carter, P. B. and F. M. Collins. 1974. Growth of typhoid and paratyphoid bacilli in intravenously infected mice. *Infection and Immunity* 10:816.

Cerin, H. and J. Hackett. 1989. Molecular cloning and analysis of the incompatibility and partition functions of the virulence plasmid of *Salmonella typhimurium*. *Microbial Pathogenesis* 7:85.

Cerin, H. and J. Hackett. 1993. The parVP region of the *Salmonella typhimurium* virulence plasmid pSLT contains four loci required for incompatibility and partition. *Plasmid* 30:30.

Chalfie, M., Y. Tu, G. Euskirchen, W. W. Ward, and D. C. Prasher. 1994. Green fluorescent protein as a marker for gene expression. *Science* 263:802.

Chambers, S. P., S. E. Prior, D. A. Barstow, and N. P. Minton. 1988. The pMTLnic cloning vectors. I. improved pUC polylinker regions to facilitate the use of sonicated DNA for nucleotide sequencing. *Gene* 68:139.

Chase, J. W. and K. R. Williams. 1986. Single-stranded DNA binding proteins required for DNA replication. *Annual Reviews in Biochemistry* 55:103.

Chase, J. W., J. B. Murphy, R. F. Whittier, E. Lorensen, and J. J. Sninsky. 1983. Amplification of ssb-1 mutant single-stranded DNA-binding protein in *Escherichia coli*. *Journal of Molecular Biology* 163,164:193.

Chatfield, S., K. Strahan, D. Pickard, I. G. Charles, C. E. Hormaeche, and G. Dougan. 1992. Evaluation of *Salmonella typhimurium* strains harbouring defined mutations in htrA and aroA in the murine salmonellosis model. *Microbial Pathogenesis* 12:145.

Clark, C., D. Bast, A. M. Sharp, P. M. St. Hilaire, R. Agha, P. E. Stein, E. J. Toone, R. J. Read, and J. L. Brunton. 1996. Phenylalanine 30 plays an important role in receptor binding of verotoxin-1. *Molecular Microbiology* 19:891.

Conradi, H. 1903. Ueber losliche,durch aseptische autolyse erhaltene giftstoffe von ruhr-und Typhusbazillen. *Dtsch. Med. Wochenschr.* 29.26.

Covone, M. G., M. Brocchi, E. Palla, W. D. da Silveira, R. Rappuoli, and C. L. Galeotti. 1998. Levels of expression and immunogenicity of attenuated *Salmonella enterica* serovar typhimurium strains expressing *Escherichia coli* mutant heat-labile enterotoxin. *Infection and Immunity* 66:224.

Dam, M. and K. Gerdes. 1994. Partitioning of plasmid R1: ten direct repeats flanking the parA promoter constitute a centromere-like partition site parC, that expresses incompatibility. *Journal of Molecular Biology* 236:1289.

Dopf, J. and T. M. Horiagon. 1996. Deletion mapping of the Aequorea victoria green fluorescent protein. *Gene* 173:39.

Downes, F. P., T. J. Barrett, J. H. Green, C. H. Aloisio, J. S. Spika, N. A. Strockbine, and I. K. Wachsmuth. 1988. Affinity purification and characterization of Shiga-like toxin II and production of toxin-specific monoclonal antibodies. *Infection and Immunity* 56:1926.

Egger, L. A., H. Park, and M. Inouye. 1997. Signal transduction via the histidyl-aspartyl phosphorelay. *Genes to Cells* 2:167.

Endo, Y., K. Tsurugi, T. Yutsudo, Y. Takeda, T. Ogasawara, and K. Igarashi. 1988. Site of action of a Vero toxin (VT2) from *Escherichia coli* O157:H7 and of Shiga toxin on eukaryotic ribosomes: RNA N-glycosidase activity of the toxins. *European Journal of Biochemistry* 171:45.

Forrest, B. D., J. T. Labrooy, S. R. Attridge, G. Boehm, L. Beyer, R. Morona, D. J. C. Shearman, and D. Rowley. 1989. Immunogenicity of a candidate live oral typhoid/cholera hybrid vaccine in humans. *J. Infect Dis.* 159:145.

Fraser, M. E., M. M. Chernaia, Y. V. Kozlov, and M. N. G. James. 1994. Crystal structure of the holotoxin from *Shigella dysenteriae* at 2.5 A resolution. *Nature Structural Biology* 1:59.

Galan, J. E., K. Nakayama, and R. Curtiss III. 1990. Cloning and characterization of the asd gene of *Salmonella typhimurium*: use in stable maintenance of recombinant plasmids in Salmonella vaccine strains. *Gene* 94:29.

Galen, J. E. and M. M. Levine. 1995. Improved suicide vectors for chromosomal mutagenesis in *Salmonella typhi*. Abstracts of the *Annual Meeting of the American Society of Microbiology* H192:(Abstract)

Galen, J. E. and M. M. Levine. 1996. Further refinements of suicide vector-mediated chromosomal mutagenesis in *Salmonella typhi*. Abstracts of the *Annual Meeting of the American Society of Microbiology* H260:(Abstract)

Galen, J. E., O. G. Gomez-Duarte, G. Losonsky, J. L. Halpern, C. S. Lauderbaugh, S. Kaintuck, M. K. Reymann, and M. M. Levine. 1997. A murine model of intranasal immunization to assess the immunogenicity of attenuated *Salmonella typhi* live vector vaccines in stimulating serum antibody responses to expressed foreign antigens. *Vaccine* 15:700.

Gay, P., D. Le Coq, M. Steinmetz, E. Ferrari, and J. A. Hoch. 1983. Cloning structural gene sacB, which codes for exoenzyme levansucrase of *Bacillus subtilis:* expression of the gene in *Escherichia coli*. *Journal of Bacteriology* 153:1424.

Gerdes, K. and S. Molin. 1986. Partitioning of plasmid R1: structural and functional analysis of the parA locus. *Journal of Molecular Biology* 190:269.

Gerdes, K., A. P. Gultyaev, T. Franch, K. Pedersen, and N. D. Mikkelsen. 1997. Antisense RNA-regulated programmed cell death. *Annual Reviews in Genetics* 31:1.

Gerichter, C. B. 1960. The dissemination of *Salmonella typhi, S. paratyphi* A, and *S. paratyphi* B through the organs of the white mouse by oral infection. *Journal of Hygiene, Cambridge* 58:307.

Gerichter, C. B. and D. L. Boros. 1962. Dynamics of infection of the blood stream and internal organs of white mice with *Salmonella typhi* by intraperitoneal injection. *Journal of Hygiene, Cambridge* 60:311.

Gomez-Duarte, O. G., J. E. Galen, S. N. Chatfield, R. Rappuoli, L. Eidels, and M. M. Levine. 1995. Expression of fragment C of tetanus toxin fused to a carboxyl-terminal fragment of diphtheria toxin in *Salmonella typhi* CVD 908 vaccine strain. *Vaccine* 13:1596.

Gonzalez, C., D. M. Hone, F. Noriega, C. O. Tacket, J. R. Davis, G. Losonsky, J. P. Nataro, S. Hoffman, A. Malik, E. Nardin, M. Sztein, D. G. Heppner, T. R. Fouts, A. Isibasi, and M. M. Levine. 1994. *Salmonella typhi* vaccine strain CVD 908 expressing the circumsporozoite protein of *Plasmodium falciparum:* strain construction and safety and immunogenicity in humans. *Journal of Infectious Diseases* 169:927.

Gordon, V. M., S. C. Whipp, H. W. Moon, A. D. O'Brien, and J. E. Samuel. 1992. An enzymatic mutant of Shiga-like toxin II variant is a vaccine candidate for edema disease of swine. *Infection and Immunity* 60:485.

Gottesman, S., W. P. Clark, V. de Crecy-Lagard, and M. R. Maurizi. 1993. ClpX, an alternative subunit for the ATP-dependent Clp protease of *Escherichia coli. Journal of Biological Chemistry* 268:22618.

Green, J. M., B. P. Nichols, and R. G. Matthews. 1996. Folate biosynthesis, reduction, and polyglutamylation. In *Escherichia coli* and Salmonella: *Cellular and molecular biology.* 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 665.

Griffin, P. M. 1995. *Escherichia coli* O157:H7 and other enterohemorrhagic *Escherichia coli.* In *Infections of the gastrointestinal tract.* M. J. Blaser, P. D. Smith, J. I. Ravdin, H. B. Greenberg and R. L. Guerrant, eds. Raven Press, Ltd, New York, p. 739.

Gyles, C. L. 1992. *Escherichia coli* cytotoxins and enterotoxins. *Canadian Journal of Microbiology* 38:734.

Heim, R., D. C. Prasher, and R. Y. Tsien. 1994. Wavelength mutations and posttranscriptional autoxidation of green fluorescent protein. *Proceedings of the National Academy of Sciences* USA 91:12501.

Hoiseth, S. K. and B. A. Stocker. 1981. Aromatic-dependent *Salmonella typhimurium* are non-virulent and effective as live vaccines. *Nature* 291:238.

Hovde, C. J., S. B. Calderwood, J. J. Mekalanos, and R. J. Collier. 1988. Evidence that glutamic acid 167 is an active-site residue of Shiga-like toxin I. *Proceedings of the National Academy of Sciences USA* 85:2568.

Jackson, M. P., E. A. Wadolkowski, D. L. Weinstein, R. K. Holmes, and A. D. O'Brien. 1990. Functional analysis of the Shiga toxin and Shiga-like toxin type II variant binding subunits by using site-directed mutagenesis. *Journal of Bacteriology* 172:653.

Jackson, M. P., R. J. Neill, A. D. O'Brien, R. K. Holmes, and J. W. Newland. 1987. Nucleotide sequence analysis and comparison of the structural genes for Shiga-like toxin I and Shiga-like toxin II encoded by bacteriophages from *Escherichia coli.* FEMS *Microbiology Letters* 44:109.

Jackson, M. P., R. L. Deresiewicz, and S. B. Calderwood. 1990. Mutational analysis of the Shiga toxin and Shiga-like toxin II enzymatic subunits. *Journal of Bacteriology* 172:3346.

Jarvis, K. G. and J. B. Kaper. 1996. Secretion of extracellular proteins by enterohemorrhagic *Escherichia coli* via a putative type III secretion system. *Infection and Immunity* 64:4826.

Jarvis, K. G., J. A. Giron, A. E. Jerse, T. K. McDaniel, M. S. Donnenberg, and J. B. Kaper. 1995. Enteropathogenic *Escherichia coli* contains a putative type III secretion system necessary for the export of proteins involved in attaching and effacing lesion formation. *Proceedings of the National Academy of Sciences USA* 92:7996.

Jensen, R. B. and K. Gerdes. 1995. Programmed cell death in bacteria: proteic plasmid stabilization systems. *Molecular Microbiology* 17:205.

Jensen, R. B. and K. Gerdes. 1997. Partitioning of plasmid R1. The ParM protein exhibits ATPase activity and interacts with the centromere-like ParR-parC complex. *Journal of Molecular Biology* 269:505.

Karem, K. L., S. Chatfield, N. Kuklin, and B. T. Rouse. 1995. Differential induction of carrier antigen-specific immunity by *Salmonella typhimurium* live-vaccine strains after single mucosal or intravenous immunization of BALB/c mice. *Infection and Immunity* 63.4557.

Karmali, M. A. 1989. Infection by verocytotoxin-producing *Escherichia coli. Clinical Microbiological Reviews* 2:15.

Karmali, M. A., M. Petric, C. Lim, P. C. Fleming, and B. T. Steele. 1983. *Escherichia coli* cytotoxin, haemolytic-uraemic syndrome, and haemorrhagic colitis. *Lancet* ii:1299.

Karmali, M. A., M. Petric, C. Lim, P. C. Fleming, G. S. Arbus, and H. Lior. 1985. The association between idiopathic hemolytic uremic syndrome and infection by verotoxin-producing *Escherichia coli. Journal of Infectious Diseases* 151:775.

Karpman, D., H. Connell, M. Svensson, F. Scheutz, P. Alm, and C. Svanborg. 1997. The role of lipopolysaccharide and Shiga-like toxin in a mouse model of *Escherichia coli* O157:H7 infection. *Journal of Infectious Diseases* 175:611.

Keusch, G. T., G. F. Grady, L. J. Mata, and J. McIver. 1972. Pathogenesis of shigella diarrhea. 1. Enterotoxin production by *Shigella dysenteriae* 1. *Journal of Clinical Investigation* 51:1212.

Killeen, K. P., V. Escuyer, J. J. Mekalanos, and R. J. Collier. 1992. Reversion of recombinant toxoids: mutations in diphtheria toxin that partially compensate for active-site deletions. *Proceeding of the National Academy of Sciences USA* 89:6207.

Kim, J. Y., H. A. Kang, and D. D. Ryu. 1993. Effects of the par locus on the growth rate and structural stability of recombinant cells. *Biotechnology Progress* 9:548.

Konowalchuk, J., J. I. Speirs, and S. Stavric. 1977. Vero response to a cytotoxin of *Escherichia coli. Infection and Immunity* 18:775.

Lehnherr, H. and M. B. Yarmolinsky. 1995. Addiction protein Phd of plasmid prophage P1 is a substrate of the ClpXP serine protease of *Escherichia coli. Proceedings of the National Academy of Sciences USA* 92:3274.

Lehnherr, H., E. Maguin, S. Jafri, and M. B. Yarmolinsky. 1993. Plasmid addiction genes of bacteriophage P1: doc, which causes cell death on curing of prophage, and phd, which prevents host death when prophage is retained. *Journal of Molecular Biology* 233:414.

Levine, M. M., J. E. Galen, E. M. Barry, F. Noriega, S. Chatfield, M. Sztein, G.

Dougan, and C. O. Tacket. 1996. Attenuated Salmonella as live oral vaccines against typhoid fever and as live vectors. *Journal of Biotechnology* 44:193.

Lindgren, S. W., J. E. Samuel, C. K. Schmitt, and A. D. O'Brien. 1994. The specific activities of Shiga-like toxin type II (SLT-II) and SLT-II-related toxins of enterohemorrhagic *Escherichia coli* differ when measured by Vero cell cytotoxicity but not by mouse lethality. *Infection and Immunity* 62:623.

Lloyd, R. G. and K. B. Low. 1996. Homologous recombination. In *Escherichia coli* and Salmonella: *Cellular and molecular biology.* 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 2236.

Lohman, T. M. and M. E. Ferrari. 1994. *Escherichia coli* single-stranded DNA-binding protein: multiple DNA-binding modes and cooperativities. *Annual Reviews in Biochemistry* 63:527.

Louise, C. B. and T. G. Obrig. 1995. Specific interaction of *Escherichia coli* O157:H7-derived Shiga-like toxin II with human renal endothelial cells. *Journal of Infectious Diseases* 172.1397.

Love, C. A., P. E. Lilley, and N. E. Dixon. 1996. Stable high-copy-number bacteriophage lambda promoter vectors for overproduction of proteins in *Escherichia coli*. *Gene* 176:49.

Lynch, A. S. and E. C. C. Lin. 1996. Responses to molecular oxygen. In *Escherichia coli* and Salmonella: *Cellular and molecular biology.* 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 1526.

Magnuson, R., H. Lehnherr, G. Mukhopadhyay, and M. B. Yarmolinsky. 1996. Autoregulation of the plasmid addiction operon of bacteriophage P1. *Journal of Biological Chemistry* 271:18705.

Mangeney, M., C. A. Lingwood, S. Taga, B. Caillou, T. Tursz, and J. Wiels. 1993. Apoptosis induced in Burkitt's lymphoma cells via $Gb_3$/CD77, a glycolipid antigen. *Cancer Research* 53:5314.

Marshall, J., R. Molloy, G. W. J. Moss, J. R. Howe, and T. E. Hughes. 1995. The jellyfish green fluorescent protein: a new tool for studying ion channel expression and function. *Neuron* 14:211.

Matthews, R. G. 1996. One-carbon metabolism. In *Escherichia coli* and Salmonella: *Cellular and molecular biology.* 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 600.

Maurizi, M. R., W. P. Clark, Y. Katayama, S. Rudikoff, J. Pumphrey, B. Bowers, and S. Gottesman. 1990. Sequence and structure of Clp P, the proteolytic component of the ATP-dependent Clp protease of *Escherichia coli*. *Journal of Biological Chemistry* 265:12536.

McClelland, M. and R. Wilson. 1998. Sample sequencing of the *Salmonella typhi* genome: comparison to the *E. coli* K-12 genome. *Infection and Immunity.*

McDaniel, T. K., K. G. Jarvis, M. S. Donnenberg, and J. B. Kaper. 1995. A genetic locus of enterocyte effacement conserved among diverse enterobacterial pathogens. *Proceedings of the National Academy of Sciences USA* 92:1664.

Melton-Celsa, A. R. and A. D. O'Brien. 1998. The structure, biology, and relative toxicity for cells and animals of Shiga toxin family members. In *Escherichia coli* O157:H7 *and other Shiga toxin-producing E. coli strains*. J. B. Kaper and A. D. O'Brien, eds. ASM Press, Washington, D.C. In press.

Mikkelsen, N. D. and K. Gerdes. 1997. Sok antisense RNA from plasmid R1 is functionally inactivated by RNaseE and polyadenylated by poly(A) polymerase I. *Molecular Microbiology* 26:311.

Moxley, R. A. and D. H. Francis. 1998. Overview of Animal Models. In *Escherichia coli O157:H7 and other Shiga toxin-producing E. coli strains*. J. B. Kaper and A. D. O'Brien, eds. ASM Press, Washington, D.C. In press.

Muhldorfer, I., J. Hacker, G. T. Keusch, D. W. Acheson, H. Tschape, A. V. Kane, A. Ritter, T. Olschlager, and A. Donohue-Rolfe. 1996. Regulation of the Shiga-like toxin II operon in *Escherichia coli*. *Infection and Immunity* 64:495.

Nakayama, K., S. M. Kelley, and R. Curtiss III. 1988. Construction of an $Asd^+$ expression-cloning vector: stable maintenance and high level expression of cloned genes in a Salmonella vaccine strain. *Bio/Technology* 6:693.

Nelson, S., S. E. Richardson, C. A. Lingwood, M. Petric, and M. A. Karmali. 1994. Biological activity of verocytotoxin (VT)2c and VT1/VT2c chimeras in the rabbit model. In *Recent advances in verocytotoxin-producing Escherichia Coli infections*. M. A. Karmali and A. G. Goglio, eds. Elsevier Science, New York, p. 245.

Nordstrom, K. and S. J. Austin. 1989. Mechanisms that contribute to the stable segregation of plasmids. *Annual Reviews in Genetics* 23:37.

Norioka, S., G. Ramakrishnan, K. Ikenaka, and M. Inouye. 1986. Interaction of a transcriptional activator, OmpR, with reciprocally osmoregulated genes, ompF and ompC, of *Escherichia coli*. *Journal of Biological Chemistry* 261:17113.

Nyholm, P., G. Magnusson, Z. Zheng, R. Norel, B. Binnington-Boyd, and C. A. Lingwood. 1996. Two distinct binding sites for globotriaosyl ceramide on verotoxins: identification by molecular modelling and confirmation using deoxy analogues and a new glycolipid receptor for all verotoxins. *Chemistry and Biology* 3:263.

Nyholm, P., J. L. Brunton, and C. A. Lingwood. 1995. Modelling of the interaction of verotoxin-1 (VT1) with its glycolipid receptor, globotriaosylceramide ($Gb_3$). *International Journal of Biological Macromolecules* 17:199.

O'Brien, A. D. 1982. Innate resistance of mice to *Salmonella typhi* infection. *Infection and Immunity* 38:948.

O'Brien, A. D., V. L. Tesh, A. Donohue-Rolfe, M. P. Jackson, S. Olsnes, K. Sandvig, A. A. Lindberg, and G. T. Keusch. 1992. Shiga toxin: biochemistry, genetics, mode of action, and role in pathogenesis. *Current Topics in Microbiology and Immunology* 180:65.

Olitsky, P. K. and I. J. Kligler. 1920. Toxins and antitoxins of *Bacillus dysenteriae* Shiga. *Journal of Experimental Medicine* 31:19.

Orosz, A., I. Boros, and P. Venetianer. 1991. Analysis of the complex transcription termination region of the *Escherichia coli* rrnB gene. *European Journal of Biochemistry* 201:653.

Oxer, M. D., C. M. Bentley, J. G. Doyle, T. C. Peakman, I. G. Charles, and A. J. Makoff. 1991. High level heterologous expression in *E. coli* using the anaerobically-activated nirB promoter. *Nucleic Acids Research* 19:2889.

Pallen, M. J. and B. W. Wren. 1997. The HtrA family of serine proteases. *Molecular Microbiology* 26:209.

Pecota, D. C., C. S. Kim, K. Wu, K. Gerdes, and T. K. Wood. 1997. Combining the hok/sok, parDE, and pnd postsegregational killer loci to enhance plasmid stability. *Applied and Environmental Microbiology* 63:1917.

Perera, L. P., J. E. Samuel, R. K. Holmes, and A. D. O'Brien. 1991. Mapping the minimal contiguous gene segment that encodes functionally active Shiga-like toxin II. *Infection and Immunity* 59:829.

Perera, L. P., J. E. Samuel, R. K. Holmes, and A. D. O'Brien. 1991. Identification of three amino acid residues in the B subunit of Shiga toxin and Shiga-like toxin type II that are essential for holotoxin activity. *Journal of Bacteriology* 173:1151.

Pittard, A. J. 1996. Biosynthesis of the aromatic amino acids. In *Escherichia coli* and Salmonella: *Cellular and molecular biology.* 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 458.

Polisky, B. 1986. Replication control of the ColE1-type plasmids. In *Maximizing gene expression.* W. S. Reznikoff and L. Gold, eds. Butterworths, Boston, p. 143.

Porter, R. D., S. Black, S. Pannuri, and A. Carlson. 1990. Use of the *Escherichia coli* ssb gene to prevent bioreactor takeover by plasmidless cells. *Bio/Technology* 8:47.

Pratt, L. A., W. Hsing, K. E. Gibson, and T. J. Silhavy. 1996. From acids to osmZ: mutiple factors influence synthesis of the OmpF and OmpC porins in *Escherichia coli*. *Molecular Microbiology* 20:911.

Puente, J. L., V. Alvarez-Scherer, G. Gosset, and E. Calva. 1989. Comparative analysis of the *Salmonella typhi* and *Escherichia coli* ompC genes. *Gene* 83:197.

Richardson, S. E., T. A. Rotman, V. Jay, C. R. Smith, L. E. Becker, M. Petric, N. F. Olivieri, and M. A. Karmali. 1992. Experimental verocytotoxemia in rabbits. *Infection and Immunity* 60:4154.

Ringquist, S., S. Shinedling, D. Barrick, L. Green, J. Binkley, G. D. Stormo, and L. Gold. 1992. Translation initiation in *Escherichia coli:* sequences within the ribosome-binding site. *Molecular Microbiology* 6:1219.

Roberts, M., S. Chatfield, and G. Dougan. 1994. Salmonella as carriers of heterologous antigens. In *Novel delivery systems for oral vaccines.* D. T. O'Hagan, ed. CRC Press, Ann Arbor, p. 27.

Rupp, W. D. 1996. DNA repair mechanisms. In *Escherichia coli and Salmonella: Cellular and molecular biology.* 2nd ed. F. C. Neidhardt, R. Curtiss III, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 2277.

Selzer, G., T. Som, T. Itoh, and J. Tomizawa. 1983. The origin of replication of plasmid p15A and comparative studies on the nucleotide sequences around the origin of related plasmids. *Cell* 32:119.

Siegler, R. L. 1995. The hemolytic uremic syndrome. *Pediatric Nephrology* 42:1505.

Siegler, R. L., A. T. Pavia, R. D. Christofferson, and M. K. Milligan. 1994. A 20-year population-based study of postdiarrheal hemolytic uremic syndrome in Utah. *Pediatrics* 94:35.

Sixma, T. K., P. E. Stein, W. G. Hol, and R. J. Read. 1993. Comparison of the B-pentamers of heat-labile enterotoxin and verotoxin-1: two structures with remarkable similarity and dissimilarity. *Biochemistry* 32:191.

Srinivasan, J., S. A. Tinge, R. Wright, J. C. Herr, and R. Curtiss III. 1995. Oral immunization with attenuated Salmonella expressing human sperm antigen induces antibodies in serum and the reproductive tract. *Biology of Reproduction* 53:462.

Stein, P. E., A. Boodhoo, G. J. Tyrrell, J. L. Brunton, and R. J. Read. 1992. Crystal structure of the cell-binding B oligomer of verotoxin-1 from *E. coli. Nature* 355:748.

Streatfield, S. J., M. Sandkvist, T. K. Sixma, M. Bagdasarian, W. G. Hol, and T. R. Hirst. 1992. Intermolecular interactions between the A and B subunits of heat-labile enterotoxin from *Escherichia coli* promote holotoxin assembly and stability in vivo. *Proceedings of the National Academy of Sciences USA* 89:12140.

Strockbine, N. A., L. R. M. Marques, J. W. Newland, H. W. Smith, R. K. Holmes, and A. D. O'Brien. 1986. Two toxin-converting phages from *Escherichia coli* O157:H7 strain 933 encode antigenically distinct toxins with similar biologic activities. *Infection and Immunity* 53:135.

Strockbine, N. A., M. P. Jackson, L. M. Sung, R. K. Holmes, and A. D. O'Brien. 1988. Cloning and sequencing of the genes for Shiga toxin from *Shigella dysenteriae* Type 1. *Journal of Bacteriology* 170:1116.

Summers, D. K. and D. J. Sherratt. 1984. Multimerization of high copy number plasmids causes instability: ColE1 encodes a determinant essential for plasmid monomerization and stability. *Cell* 36:1097.

Tacket, C. O., D. M. Hone, R. Curtiss III, S. M. Kelly, G. Losonsky, L. Guers, A. M. Harris, R. Edelman, and M. M. Levine. 1992. Comparison of the safety and immunogenicity of $\Delta$aroC$\Delta$aroD and $\Delta$cya$\Delta$crp *Salmonella typhi* strains in adult volunteers. *Infection and Immunity* 60:536.

Tacket, C. O., M. Sztein, G. Losonsky, S. S. Wasserman, J. P. Nataro, R. Edelman, D. Pickard, G. Dougan, S. Chatfield, and M. M. Levine. 1997. Safety of live oral *Salmonella typhi* vaccine strains with deletions in htrA and aroC aroD and immune responses in humans. *Infection and Immunity* 65:452.

Tacket, C. O., S. M. Kelley, F. Schodel, G. Losonsky, J. P. Nataro, R. Edelman, M.

M. Levine, and R. Curtiss III. 1997. Safety and immunogenicity in humans of an attenuated *Salmonella typhi* vaccine vector strain expressing plasmid-encoded hepatitis B antigens stabilized by the Asd-balanced lethal vector system. *Infection and Immunity* 65:3381.

Takeda, Y. 1995. Shiga and Siga-like (Vero) toxins. In *Bacterial toxins and virulence factors in disease.* J. Moss, B. Iglewski, M. Vaughan and A. Tu, eds. Marcel Dekker, Inc. New York, p. 313.

Tauxe, R. V. 1998. Public health perspective on immunoprophylactic strategies for *Escherichia coli* O157:H7: who or what would we immunize? In *Escherichia coli O157:H7 and other Shiga toxin-producing E. coli strains.* J. B. Kaper and A. D. O'Brien, eds. ASM Press, Washington, D.C. In press.

Tesh, V. L., J. A. Burris, J. W. Owens, V. M. Gordon, E. A. Wadolkowski, A. D. O'Brien, and J. E. Samuel. 1993. Comparison of the relative toxicities of Shiga-like toxins type I and type II for mice. *Infection and Immunity* 61:3392.

Thisted, T., A. K. Nielsen, and K. Gerdes. 1994. Mechanism of post-segregational killing: translation of Hok,SrnB and Pnd mRNAs of plasmids R1, F and R483 is activated by 3'-end processing. *EMBO Journal* 13:1950.

Thisted, T., N. S. Sorensen, and K. Gerdes. 1995. Mechanism of post-segregational killing: secondary structure analysis of the entire Hok mRNA from plasmid R1 suggests a fold-back structure that prevents translation and antisense RNA binding. *Journal of Molecular Biology* 247:859.

Thisted, T., N. S. Sorensen, E. G. Wagner, and K. Gerdes. 1994. Mechanism of post-segregational killing: Sok antisense RNA interacts with Hok mRNA via its 5'-end single-stranded leader and competes with the 3'-end of Hok mRNA for binding to the mok translational initiation region. *EMBO Journal* 13:1960.

Tinge, S. A. and R. Curtiss III. 1990. Conservation of *Salmonella typhimurium* virulence plasmid maintenance regions among Salmonella serovars as a basis for plasmid curing. *Infection and Immunity* 58:3084.

Tinge, S. A. and R. Curtiss III. 1990. Isolation of the replication and partitioning regions of the *Salmonella typhimurium* virulence plasmid and stabilization of heterologous replicons. *Journal of Bacteriology* 172:5266.

Umbarger, H. E. 1978. Amino acid biosynthesis and its regulation. *Annual Reviews in Biochemistry* 47:533.

Valdivia, R. H. and S. Falkow. 1997. Fluorescence-based isolation of bacterial genes expressed within host cells. *Science* 277:2007.

Valdivia, R. H., A. E. Hromockyj, D. Monack, L. Ramakrishnan, and S. Falkow. 1996. Applications for green fluorescent protein (GFP) in the study of host-pathogen interactions. *Gene* 173:47.

Vicari, G., A. J. Olitzki, and Z. Olitzki. 1960. The action of the thermolabile toxin of *Shigella dysenteriae* on cells cultivated in vitro. *British Journal of Experimental Pathology* 41:179.

Wada, K., Y. Wada, F. Ishibashi, T. Gojobori, and T. Ikemura. 1992. Codon usage tabulated from the GenBank genetic sequence data. *Nucleic Acids Research* 20:2111.

Wadolkowski, E. A., L. M. Sung, J. A. Burris, J. E. Samuel, and A. D. O'Brien. 1990. Acute renal tubular necrosis and death of mice orally infected with *Escherichia coli* strains that produce Shiga-like toxin type II. *Infection and Immunity* 58:3959.

Wang, S. and T. Hazelrigg. 1994. Implications for bcd mRNA localization from spatial distribution of exu protein in Drosophila oogenesis. *Nature* 369:400.

Wang, Y., Z. Zhang, S. Yang, and R. Wu. 1992. Cloning of par region and the effect of par region on the stability of pUC9. *Chinese Journal of Biotechnology* 8: 107.

Williams, K. R., J. B. Murphy, and J. W. Chase. 1984. Characterization of the structural and functional defect in the *Escherichia coli* single-stranded DNA binding protein encoded by the ssb-1 mutant gene. *Journal of Biological Chemistry* 259:11804.

Yamasaki, S., M. Furutani, K. Ito, K. Igarashi, M. Nishibuchi, and Y. Takeda. 1991. Importance of arginine at postion 170 of the A subunit of Vero toxin 1 produced by enterohemorrhagic *Escherichia coli* for toxin activity. *Microbial Pathogenesis* 11:1.

Yu, J. and J. B. Kaper. 1992. Cloning and characterization of the eae gene of enterohaemorrhagic *Escherichia coli*. *Molecular Microbiology* 6:411.

Zalkin, H. and P. Nygaard. 1996. Biosynthesis of purine nucleotides. In *Escherichia coli and Salmonella: Cellular and molecular biology*. 2nd ed. F. C. Neidhardt, J. L. Ingraham, E. C. C. Lin, K. B. Low, B. Magasanik, W. S. Reznikoff, M. Riley, M. Schaechter and H. E. Umbarger, eds. ASM Press, Washington, D.C. p. 561.

Zhang, X., Y. Lou, M. Koopman, T. Doggett, K. S. K. Tung, and R. Curtiss III. 1997. Antibody responses and infertility in mice following oral immunization with attenuated *Salmonella typhimurium* expressing recombinant murine ZP3. *Biology of Reproduction* 56:33.

Zoja, C., D. Corna, C. Farina, G. Sacchi, C. A. Lingwood, M. P. Doyle, V. V. Padhye, M. Abbate, and G. Remuzzi. 1992. Verotoxin glycolipid receptors determine the localization of microangiopathic process in rabbits given verotoxin-1. *Journal of Laboratory and Clinical Medicine* 120:229.

Zurita, M., F. Bolivar, and X. Soberon. 1984. Construction and characterization of new cloning vehicles. VII. Construction of plasmid pBR327par, a completely sequenced, stable derivative of pBR327 containing the par locus of pSC101. *Gene* 28:119.

---

What is claimed is:

1. An expression plasmid comprising:

a restricted-copy-number origin of replication, wherein the expression plasmid is limited to a copy number from about 2 to 75 copies per cell and wherein the origin of replication has transcriptional terminators at the 5' and 3' end of said origin of replication such that said origin of replication is isolated from transcription beginning outside of the origin of replication;

a selection marker;

a post-segregational killing system; and an inducible promoter linked to a heterologous antigen coding sequence, wherein the inducible promoter is an ompC promoter (SEQ ID NO: 1, from 7 to 464).

2. The expression plasmid of claim 1, wherein the origin of replication is selected from the group consisting oriE1 (SEQ ID NO: 1 (from 1251 to 1932)), ori15A (SEQ ID NO: 2 (from 1251 to 1899)), or ori101 (SEQ ID NO: 3 (from 1251 to 3196)).

3. The expression plasmid of claim 1, wherein the transcriptional terminator comprises SEQ ID NO:1 (from 1954 to 2374).

4. The expression plasmid of claim 1, wherein the transcriptional terminator comprises SEQ ID NO:1 (from 1215 to 1251).

5. The expression plasmid of claim 1, wherein the selection marker is the tetA resistance gene (SEQ ID NO:1 from 3591 to 2403).

6. The expression plasmid of claim 1, wherein the post-segregational killing system consists of hok-sok (SEQ ID NO:1 (from 3612 to 4196)).

7. The expression plasmid of claim 1, wherein the plasmid comprises SEQ ID NO: 1.

8. The expression plasmid of claim 1, wherein the heterologous antigen coding sequence encodes a detoxified Shiga toxin comprising a mutated segment of amino acids comprising SEQ ID NO: 4.

9. The expression plasmid of claim 1, wherein the heterologous antigen coding sequence encodes a detoxified Shiga toxin comprising a mutated segment of amino acids comprising SEQ ID NO: 5.

10. The expression plasmid of claim 1, wherein the heterologous antigen coding sequence encodes a detoxified Shiga toxin comprising a mutated segment of amino acids comprising SEQ ID NO: 6.

11. The expression plasmid of claim 1, wherein the heterologous antigen coding sequence encodes a detoxified Shiga toxin comprising a mutated segment of amino acids comprising SEQ ID NO: 7.

12. The expression plasmid of claim 1, further comprising a partitioning system.

13. The expression plasmid of claim 1, wherein the partitioning system comprises par (SEQ ID NO: 3 (from 2824 to 3196).

* * * * *